(12) United States Patent
Yun et al.

(10) Patent No.: US 11,527,727 B2
(45) Date of Patent: Dec. 13, 2022

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Bu Yong Yun, Cheonan-si (KR); Hyung Dong Lee, Cheonan-si (KR); Ki Ho So, Cheonan-si (KR); Sun-Hee Lee, Cheonan-si (KR); Yun Suk Lee, Cheonan-si (KR); Zhaoyang Zhong, Cheonan-si (KR)

(73) Assignee: DUK SAN NEOLUX CO., LTD., Cheonan-si (KR)

(*) Notice: Subject to any disclaimer, the term of this patent is extended or adjusted under 35 U.S.C. 154(b) by 0 days.

(21) Appl. No.: 17/810,355

(22) Filed: Jul. 1, 2022

(65) Prior Publication Data
US 2022/0352475 A1 Nov. 3, 2022

Related U.S. Application Data

(63) Continuation-in-part of application No. 17/212,886, filed on Mar. 25, 2021, which is a continuation of (Continued)

(30) Foreign Application Priority Data

Oct. 26, 2020 (KR) ............ 10-2020-0139441

(51) Int. Cl.
*C07D 251/24* (2006.01)
*C09K 11/06* (2006.01)
(Continued)

(52) U.S. Cl.
CPC ........ *H01L 51/0073* (2013.01); *C07D 251/24* (2013.01); *C09K 11/06* (2013.01); *H01L 51/0058* (2013.01); *H01L 51/0059* (2013.01); *H01L 51/0065* (2013.01); *H01L 51/0067* (2013.01); *H01L 51/0072* (2013.01); *H01L 51/0074* (2013.01); *C07B 2200/05* (2013.01);
(Continued)

(58) Field of Classification Search
CPC .................................. C07D 251/24
See application file for complete search history.

(56) References Cited

U.S. PATENT DOCUMENTS

2018/0072695 A1 3/2018 Byun et al.
2018/0123048 A1 5/2018 So et al.
(Continued)

FOREIGN PATENT DOCUMENTS

WO 2019/124902 A1 6/2019
WO WO-2020/032424 A1 * 2/2020 ............ H01L 51/00

OTHER PUBLICATIONS

STN Search (Apr. 7, 2021).
SciFinder Search (Apr. 7, 2021).

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound capable of improving the luminous efficiency, stability and lifespan of a device employing the same, an organic electronic element employing the same, and an electronic device thereof.

17 Claims, 2 Drawing Sheets

Related U.S. Application Data application No. 17/096,790, filed on Nov. 12, 2020, now Pat. No. 11,063,226.

(51) Int. Cl.
*H01L 51/00* (2006.01)
*H01L 51/50* (2006.01)

(52) U.S. Cl.
CPC .. *C09K 2211/1018* (2013.01); *H01L 51/5016* (2013.01); *H01L 51/5056* (2013.01); *H01L 51/5072* (2013.01); *H01L 51/5096* (2013.01); *H01L 2251/5384* (2013.01)

(56) References Cited

U.S. PATENT DOCUMENTS

| | | |
|---|---|---|
| 2018/0151806 A2 | 5/2018 | Park et al. |
| 2018/0261774 A1 | 9/2018 | Park et al. |

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

In other words, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic device has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound, an organic electronic element using the same, and an electronic device thereof.

Technical Solution

The present invention provides a compound represented by Formula 1-1.

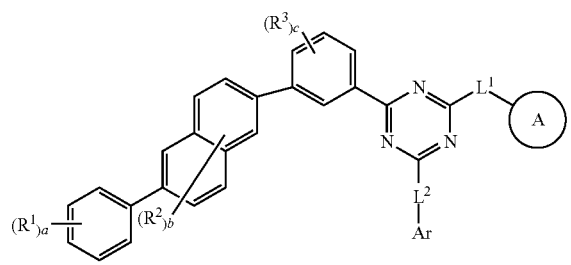

Formula 1-1

In another aspect, the present invention provides an organic electronic element comprising the compound represented by Formula 1-1 and an electronic device thereof.

Effects of the Invention

By using the compound according to the present invention, high luminous efficiency, low driving voltage and high heat resistance of the device can be achieved, and color purity and lifespan of the device can be greatly improved.

Figure 1:
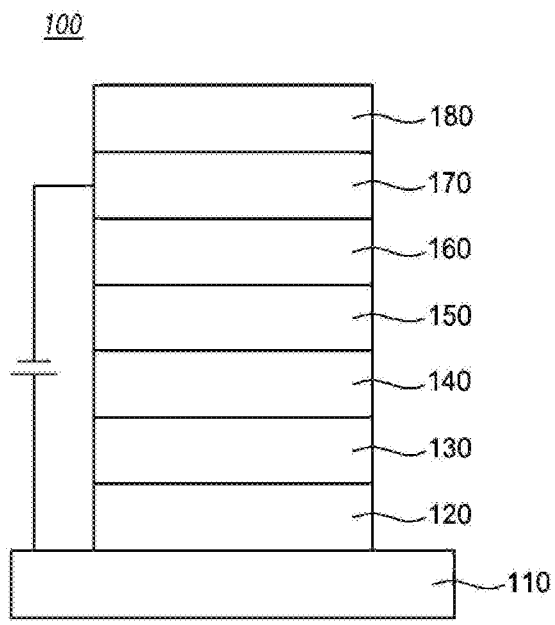
FIG. 1 to FIG. 3 are each an exemplary view of an organic electroluminescent device according to the present invention.

The numbers used in each of the drawings refer to the following:
100, 200, 300: organic electronic element
110: the first electrode
120: hole injection layer
130: hole transport layer
140: emitting layer
150: electron transport layer
160: electron injection layer
170: second electrode
180: light efficiency enhancing Layer
210: buffer layer
220: emitting auxiliary layer
320: first hole injection layer
330: first hole transport layer
340: first emitting layer
350: first electron transport layer
360: first charge generation layer
361: second charge generation layer
420: second hole injection layer
430: second hole transport layer
440: second emitting layer
450: second electron transport layer
CGL: charge generation layer
ST1: first stack
ST2: second stack

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

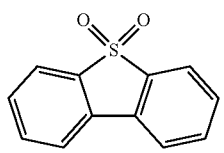 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

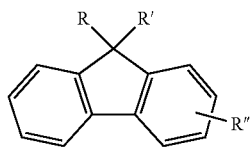

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro' and 'tri-spiro', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

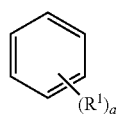

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

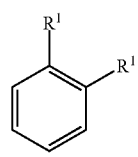

(a = 2)

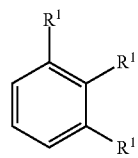

(a = 3)

Hereinafter, a compound according to an aspect of the present invention and an organic electronic element including the same will be described.

The present invention provides a compound represented by Formula 1-1.

Formula 1-1

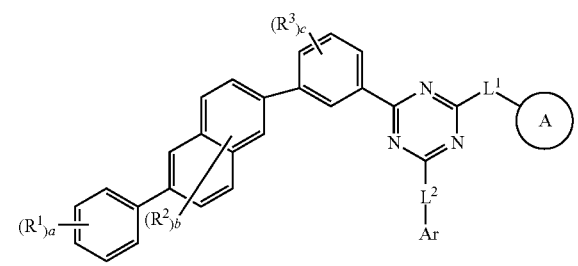

In Formula 1-1, each symbol may be defined as follows.

1) $L^1$ is a substituent represented by any one of Formulas L-1 to L-4,

<Formula L-1> <Formula L-2> <Formula L-3> <Formula L-4>

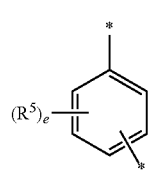

<Formula L-1>

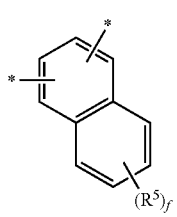

<Formula L-2>

<Formula L-3>

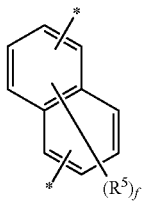

<Formula L-4>

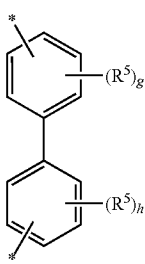

2) $L^2$ is a single bond; or a $C_6$-$C_{60}$ arylene group;

3) Ar is a $C_6$-$C_{60}$ aryl group, preferably a $C_6$-$C_{30}$ aryl group, more preferably a $C_6$-$C_{24}$ aryl group, such as phenylene, biphenyl, naphthalene, terphenyl, etc.

4) Ring A is a substituent represented by Formula a; or Formula b;

<Formula a>

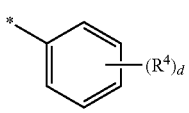

<Formula b>

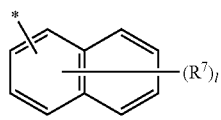

5) $R^1$, $R^2$, $R^3$, $R^4$, $R^5$ and $R^6$ are the same or different from each other and are each independently hydrogen; or deuterium;

6) $R^7$ is selected from the group consisting of hydrogen; deuterium; a $C_6$-$C_{60}$ aryl group; and a $C_6$-$C_{60}$ aryl group substituted with deuterium;

7) a and d are independently of each other an integer of 0 to 5, b and f are independently of each other an integer of 0 to 6, c, e, g and h are each independently an integer from 0 to 4, i is an integer from 0 to 7, 8) * means the position to be bonded, 9) Here, the aryl group and the arylene group may be further substituted with one or more substituents selected from the group consisting of deuterium; a $C_6$-$C_{20}$ aryl group; and a $C_6$-$C_{20}$ aryl group substituted with deuterium; respectively.

$L^2$ may be represented by any one of Formulas a-1 to a-20.

<Formula a-1> <Formula a-2> <Formula a-3> <Formula a-4> <Formula a-5>

<Formula a-1>

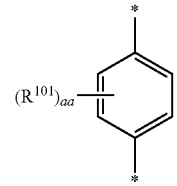

<Formula a-2>

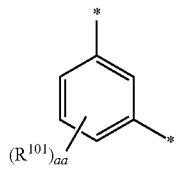

<Formula a-3>

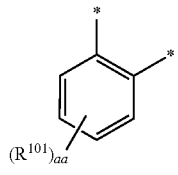

<Formula a-4>

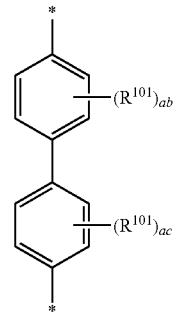

<Formula a-5>

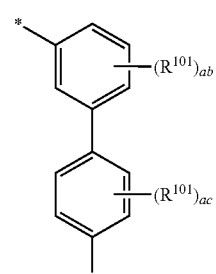

<Formula a-6> <Formula a-7> <Formula a-8> <Formula a-9> <Formula a-10>

<Formula a-6>

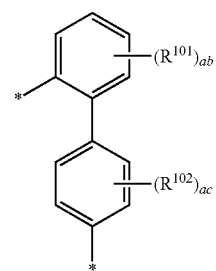

-continued
<Formula a-7>
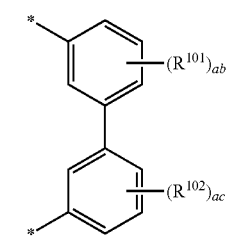
<Formula a-8>
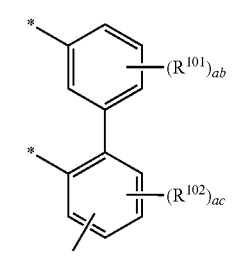
<Formula a-9>
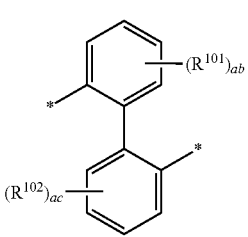
<Formula a-10>
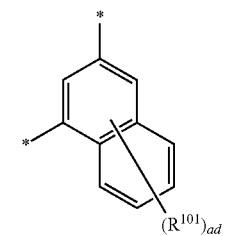
<Formula a-11> <Formula a-12> <Formula a-13> <Formula a-14> <Formula a-15>
<Formula a-11>
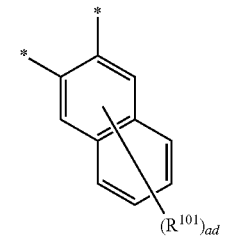
<Formula a-12>
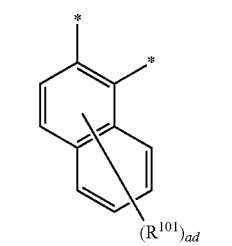
<Formula a-13>
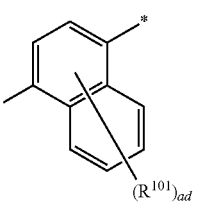
<Formula a-14>
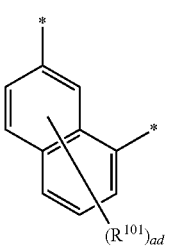
<Formula a-15>
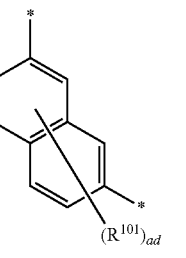
<Formula a-16> <Formula a-17> <Formula a-18> <Formula a-19> <Formula a-20>
<Formula a-16>
<Formula a-17>
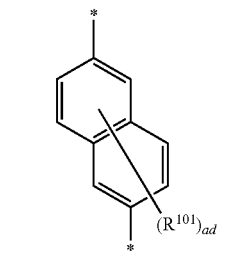
<Formula a-18>
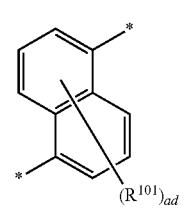

<Formula a-19>

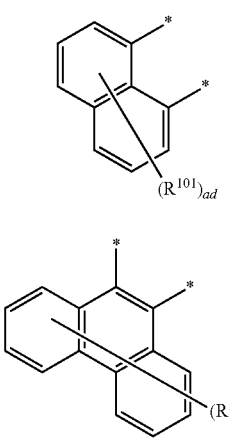

<Formula a-20>

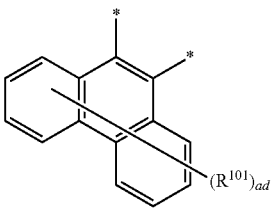

In Formulas a-1 to a-20, each symbol may be defined as follows.

1) $R^{101}$ and $R^{102}$ are each the same or different, and each independently hydrogen; deuterium; a $C_6$-$C_{20}$ aryl group; or a $C_6$-$C_{20}$ aryl group substituted with deuterium;

In case $R^{101}$ and $R^{102}$ are aryl groups, they may be phenylene, biphenyl, naphthalene, terphenyl, etc.;

2) aa, ab and ac are each independently an integer from 0 to 4, ad is an integer from 0 to 6, ae is an integer from 0 to 8, 3) * means a position at which triazine or Ar is bonded.

Ar may be represented by any one of Formulas b-1 to b-8.

<Formula b-1> <Formula b-2> <Formula b-3> <Formula b-4>

<Formula b-1>

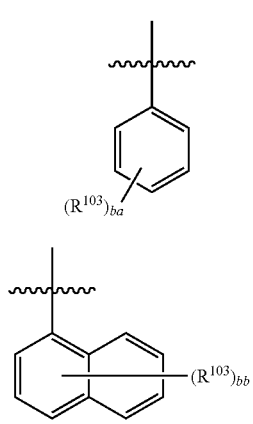

<Formula b-2>

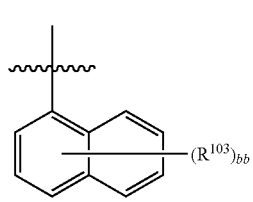

<Formula b-3>

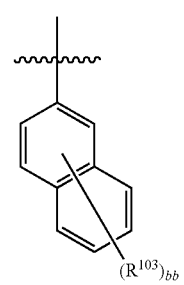

<Formula b-4>

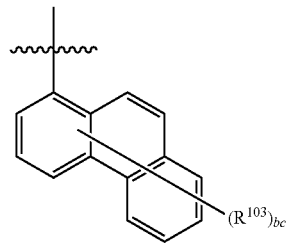

<Formula b-5> <Formula b-6> <Formula b-7> <Formula b-8>

<Formula b-5>

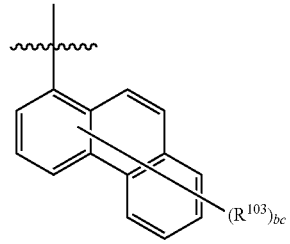

<Formula b-6>

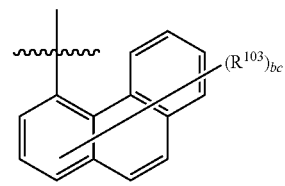

<Formula b-7>

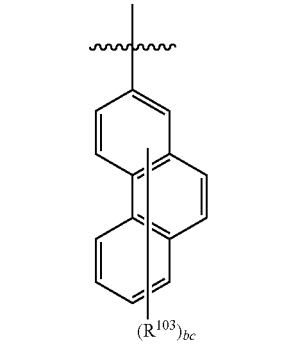

<Formula b-8>

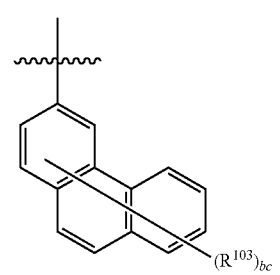

In Formulas b-1 to b-8, each symbol may be defined as follows.

1) $R^{103}$ is hydrogen; deuterium; a $C_6$-$C_{20}$ aryl group; or a $C_6$-$C_{20}$ aryl group substituted with deuterium;

In case $R^{103}$ is aryl group, it may be phenylene, biphenyl, naphthalene, terphenyl, etc.;

2) ba is an integer from 0 to 5, bb is an integer from 0 to 7, bc is an integer from 0 to 9, 3) ― means a position to be bonded to L.

Formula L-1 may be preferably represented by any one of Formulas L-1-1 to L-1-3.

<Formula L-1-1> <Formula L-1-2> <Formula L-1-3>

<Formula L-1-1>

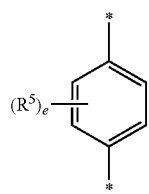

<Formula L-1-2>

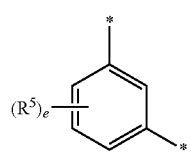

<Formula L-1-3>

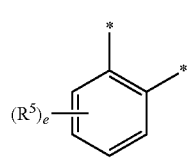

{In Formulas L-1-1 to L-1-3, $R^5$, e and * are as defined above.}

Formula L-2 may be preferably represented by any one of Formulas L-2-1 to L-2-4.

<Formula L-2-1>

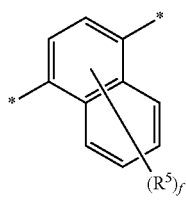

<Formula L-2-2>

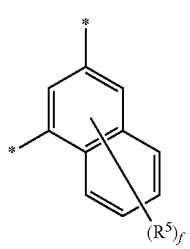

<Formula L-2-3>

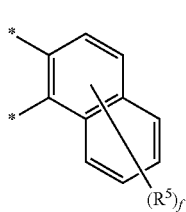

<Formula L-2-4>

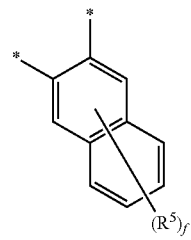

{In Formulas L-2-1 to L-2-4, $R^5$, f and * are as defined above.}

Formula L-3 may be preferably represented by any one of Formulas L-3-1 to L-3-8.

<Formula L-3-1>

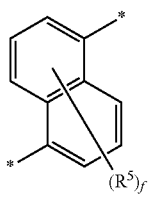

<Formula L-3-2>

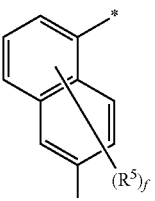

<Formula L-3-3>

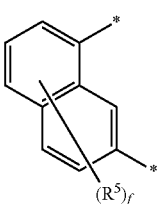

<Formula L-3-4>

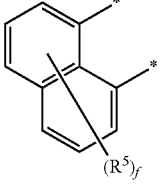

<Formula L-3-5>

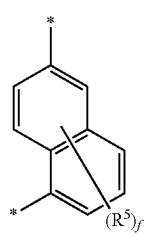

<Formula L-3-6>
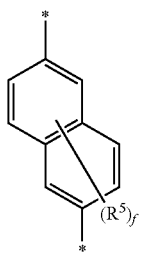
<Formula L-3-7>
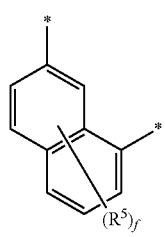
<Formula L-3-8>
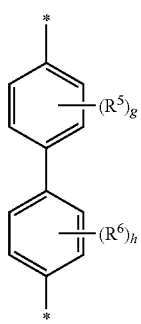
{In Formulas L-3-1 to L-3-8, $R^5$, f and * are as defined above.}
Formula L-4 may preferably be represented by any one of Formulas L-4-1 to L-4-6.
<Formula L-4-1> <Formula L-4-2> <Formula L-4-3>
<Formula L-4-1>
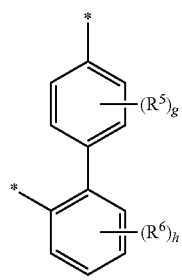
<Formula L-4-2>
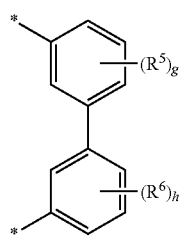
<Formula L-4-3>
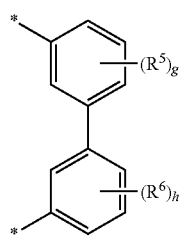
<Formula L-4-4> <Formula L-4-5> <Formula L-4-6>
<Formula L-4-4>
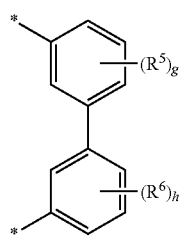
<Formula L-4-5>
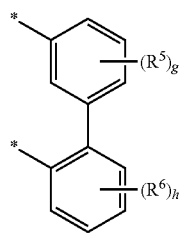
<Formula L-4-6>
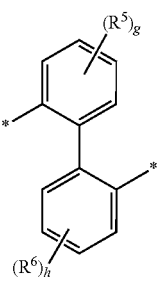

{In Formulas L-4-1 to L-4-6, $R^5$, $R^6$, g, h, and * are as defined above.}
Also, Formula 1-1 is represented by Formula 1-1-a or Formula 1-1-b.
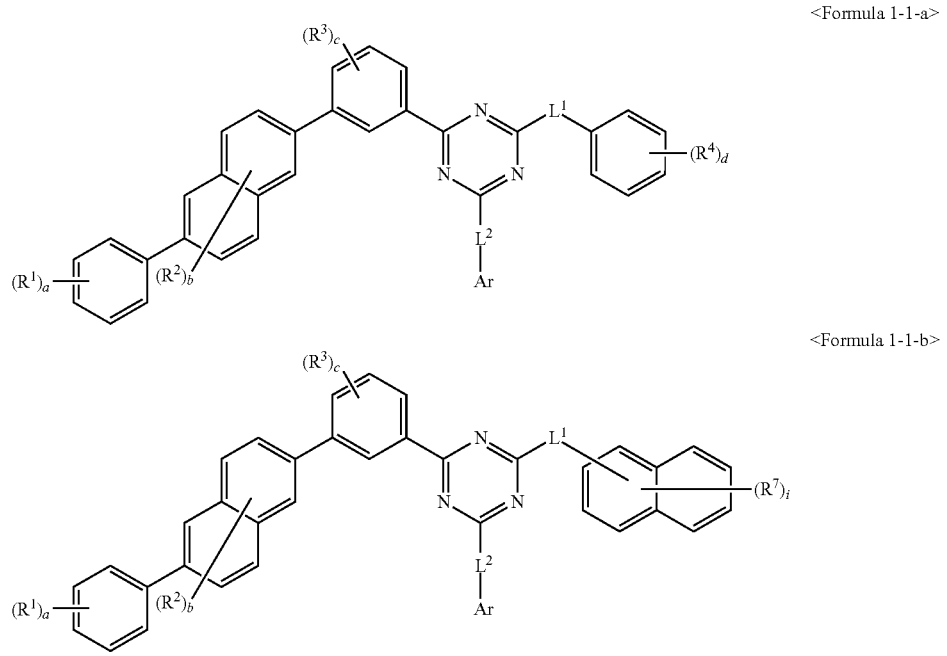
<Formula 1-1-a>
<Formula 1-1-b>
{In Formula 1-1-a or Formula 1-1-b, $R^1$, $R^2$, $R^3$, $R^4$, $R^7$, $L^1$, $L^2$, Ar, a, b, c, d and i are the same as defined above.}
Also, Formula 1-1 is represented by any one of Formulas 1-1-1 to 1-1-5.
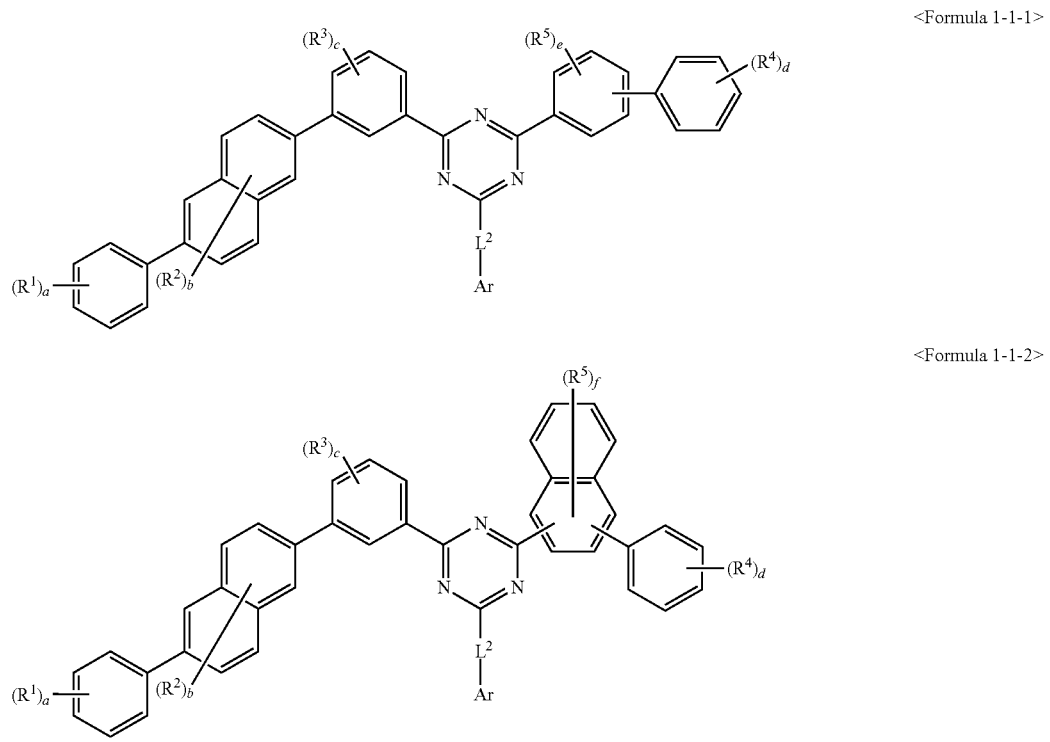
<Formula 1-1-1>
<Formula 1-1-2>

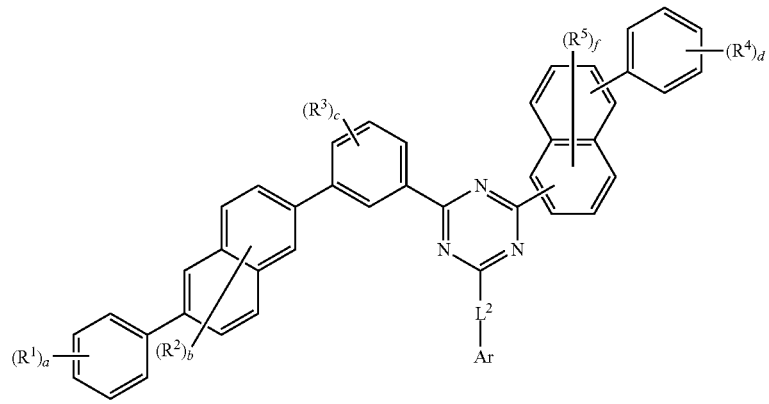
<Formula 1-1-3>
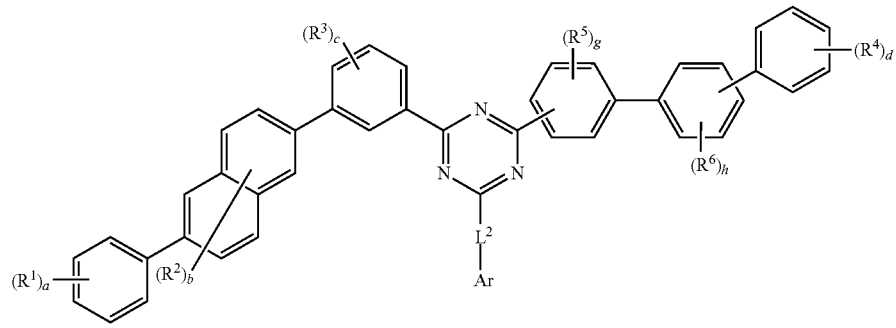
<Formula 1-1-4>
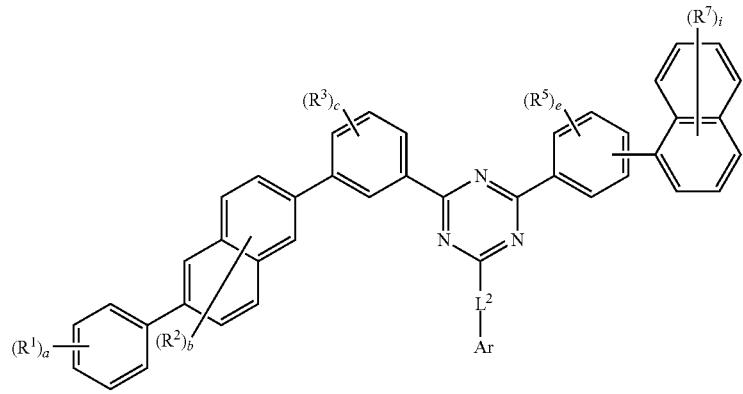
<Formula 1-1-5>

{In Formulas 1-1-1 to 1-1-5, $R^1$, $R^2$, $R^3$, $R^4$, $R^5$, $R^6$, $R^7$, $L^2$, Ar, a, b, c, d, e, f, g, h and i are the same as defined above.}
Also, Formula 1-1 is represented by any one of Formulas 1-1-1-a to 1-1-1-c.
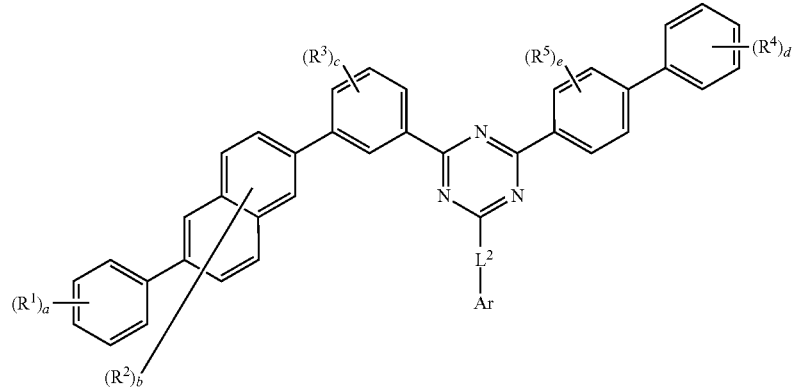
<Formula 1-1-1-a>
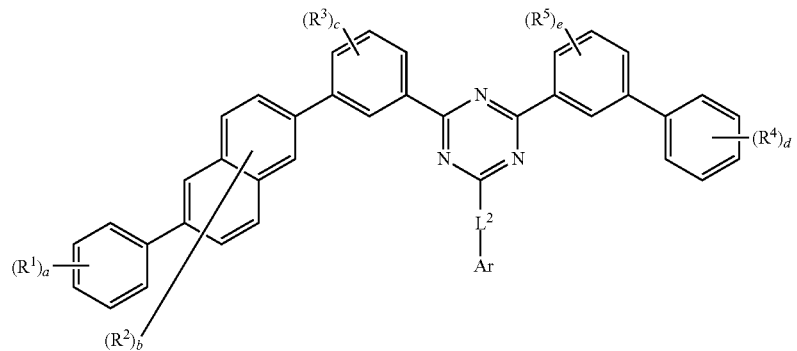
<Formula 1-1-1-b>
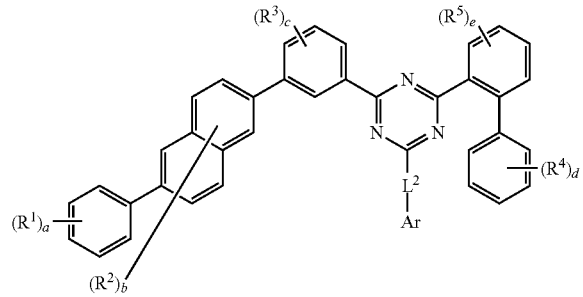
<Formula 1-1-1-c>

{In Formulas 1-1-1-a to 1-1-1-c, $R^1$, $R^2$, $R^3$, $R^4$, $R^5$, $L^2$, Ar, a, b, c, d and e are the same as defined above.}
Also, Formula 1-1 is represented by any one of Formulas 1-1-2-a to 1-1-2-c
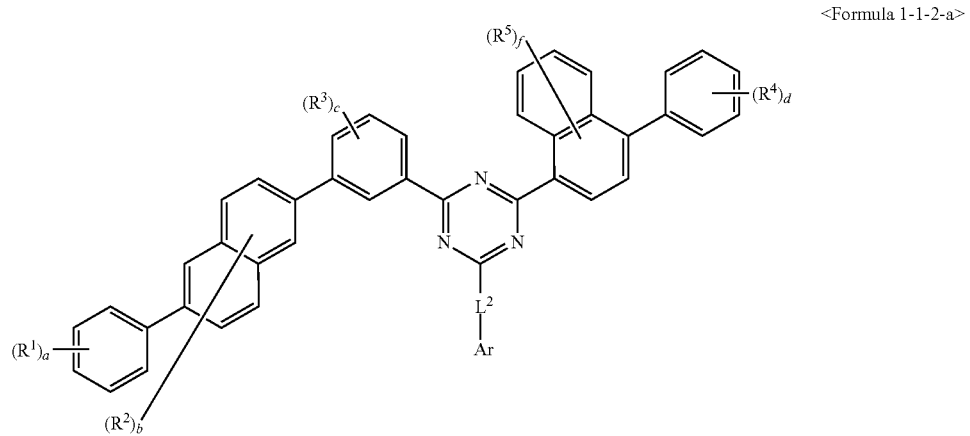
<Formula 1-1-2-a>
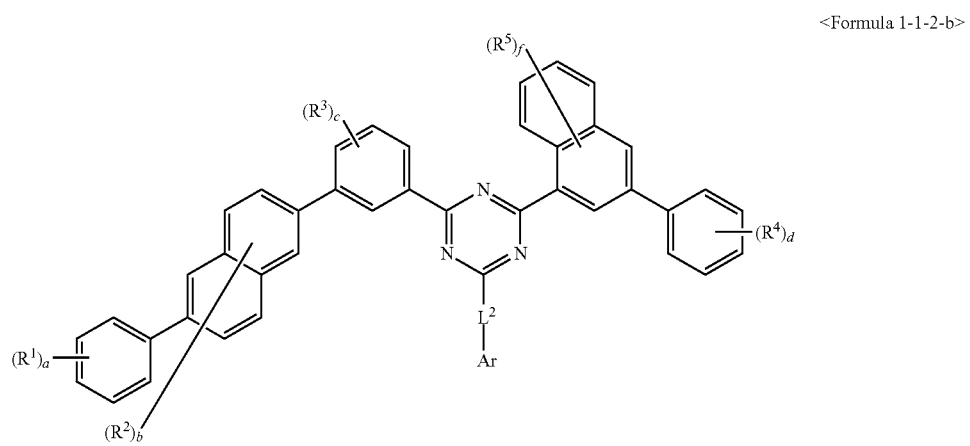
<Formula 1-1-2-b>
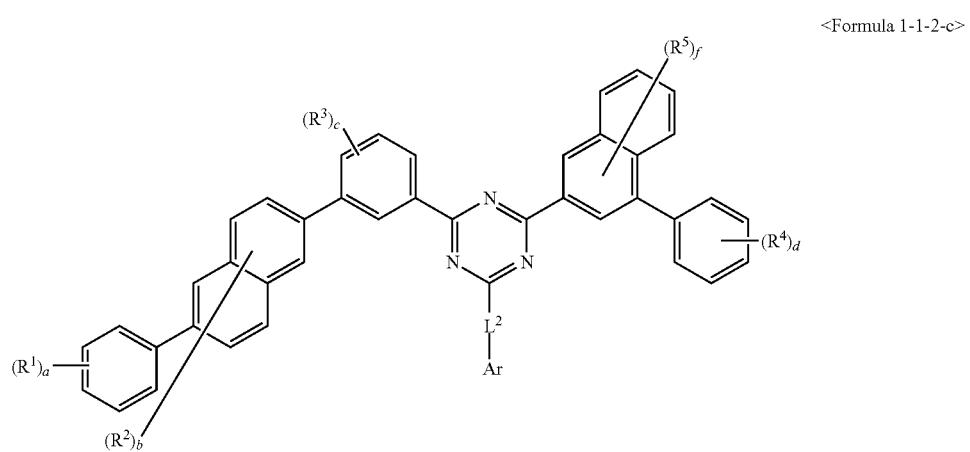
<Formula 1-1-2-c>

{In Formulas 1-1-2-a to 1-1-2-c, $R^1$, $R^2$, $R^3$, $R^4$, $R^5$, $L^2$, Ar, a, b, c, d and f are same as defined above.}
Also, Formula 1-1 is represented by Formula 1-1-3-a or Formula 1-1-3-b,
<Formula 1-1-3-a>
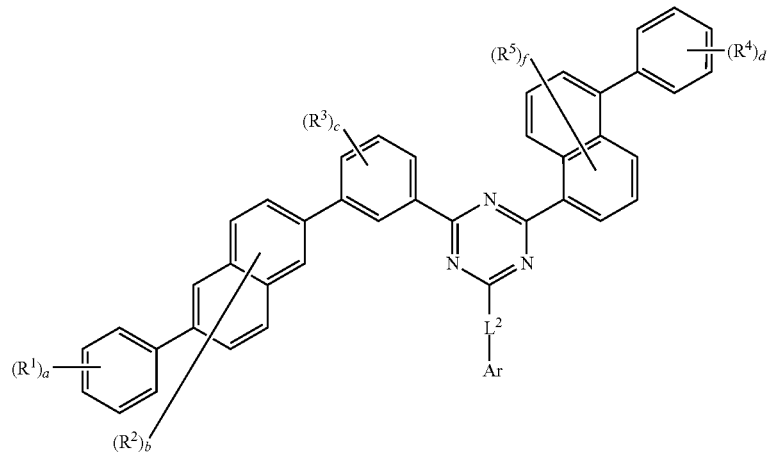
<Formula 1-1-3-b>
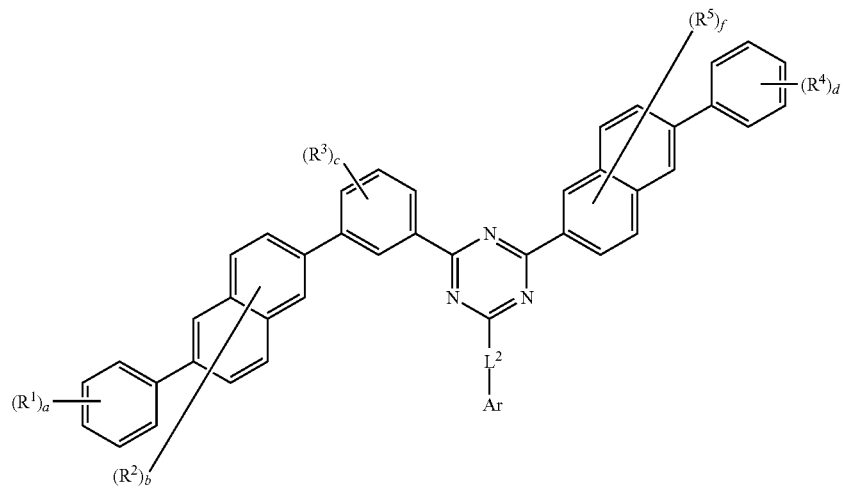
{In Formula 1-1-3-a or Formula 1-1-3-b, $R^1$, $R^2$, $R^3$, $R^4$, $R^5$, $L^2$, Ar, a, b, c, d and f are the same as defined above.}
Also, Formula 1-1 is represented by Formula 1-1-4-a.
<Formula 1-1-4-a>
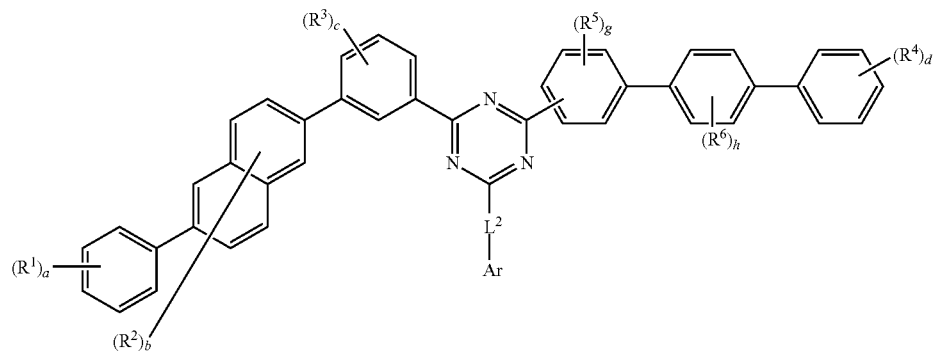

{In Formula 1-1-4-a, $R^1$, $R^2$, $R^3$, $R^4$, $R^5$, $R^6$, $L^2$, Ar, a, b, c, d, g, and h are as defined above.}
Also, Formula 1-1 is represented by Formula 1-1-4-b or Formula 1-1-4-c.
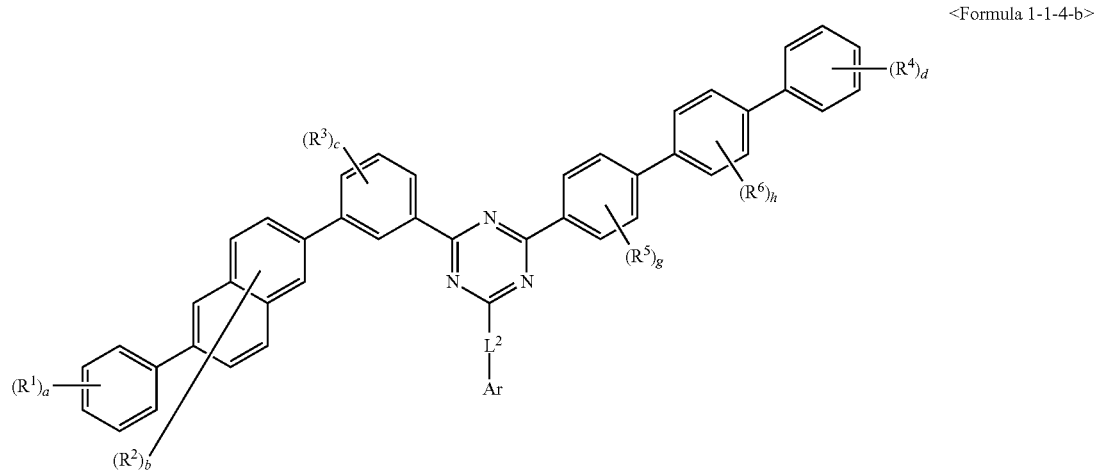
<Formula 1-1-4-b>
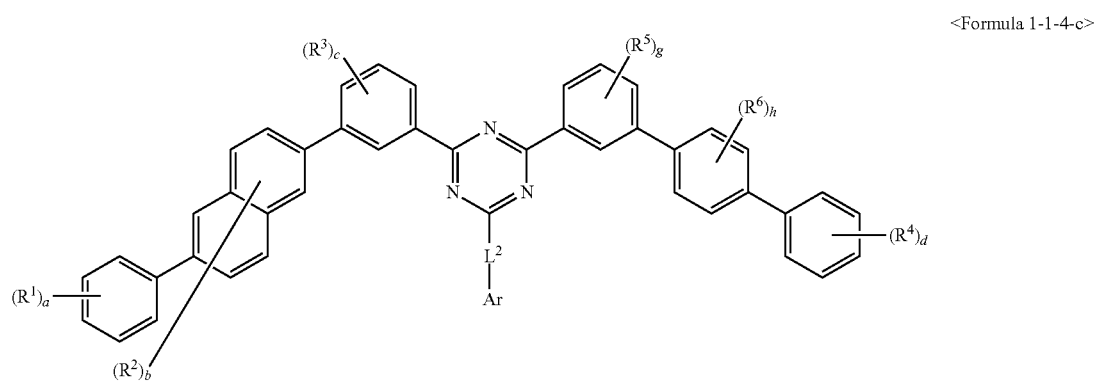
<Formula 1-1-4-c>
{In Formula 1-1-4-b or Formula 1-1-4-c, $R^1$, $R^2$, $R^3$, $R^4$, $R^5$, $R^6$, $L^2$, Ar, a, b, c, d, g and h are as the same as defined above.}
Also, Formula 1-1 is represented by any one of Formulas 1-1-5-a to 1-1-5-c.
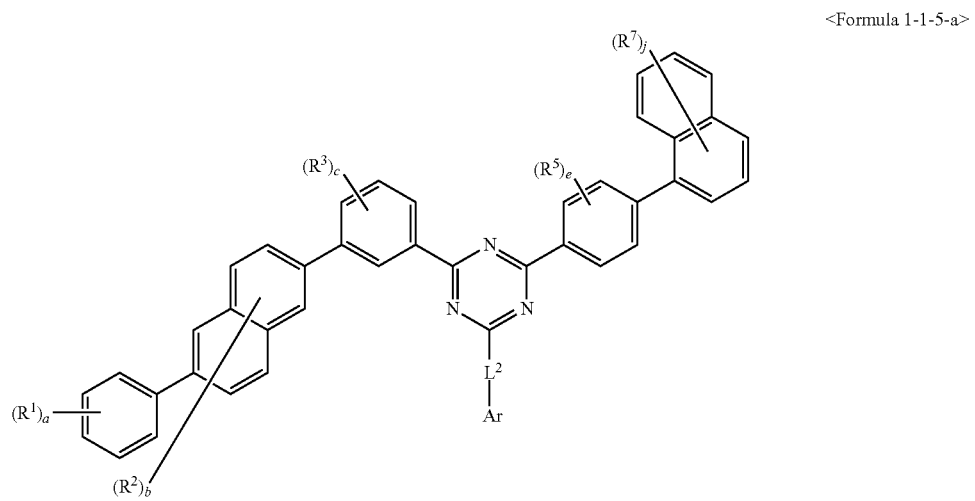
<Formula 1-1-5-a>

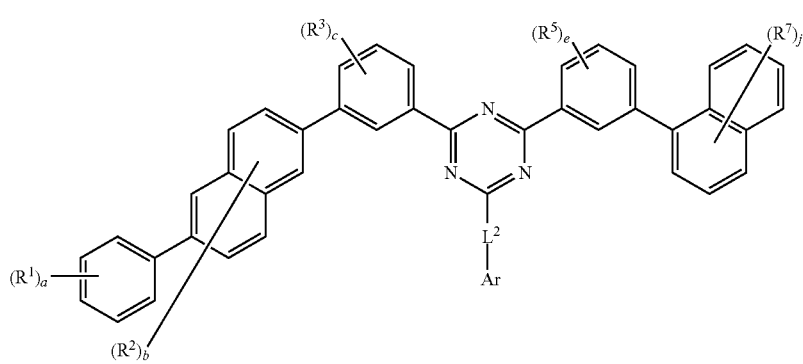
<Formula 1-1-5-b>
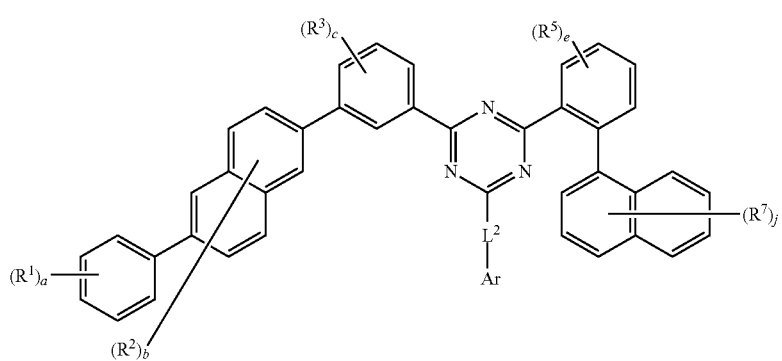
<Formula 1-1-5-c>
{In Formulas 1-1-5-a to 1-1-5-c, $R^1$, $R^2$, $R^3$, $R^5$, $R^7$, $L^2$, Ar, a, b, c, e and i are the same as defined above.}
Also, the compound represented by Formula 1-1 is represented by any one of the following compounds P-1 to P-44
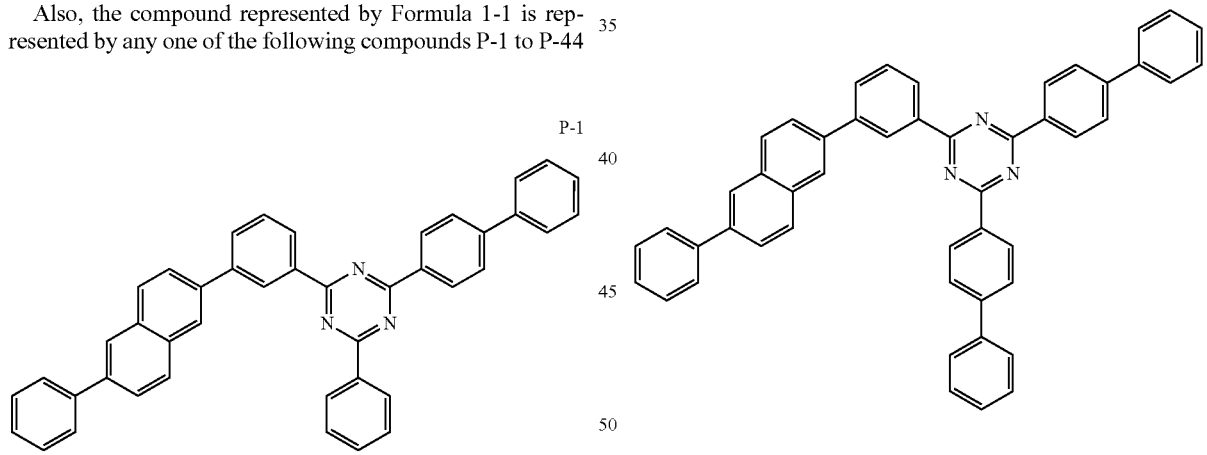
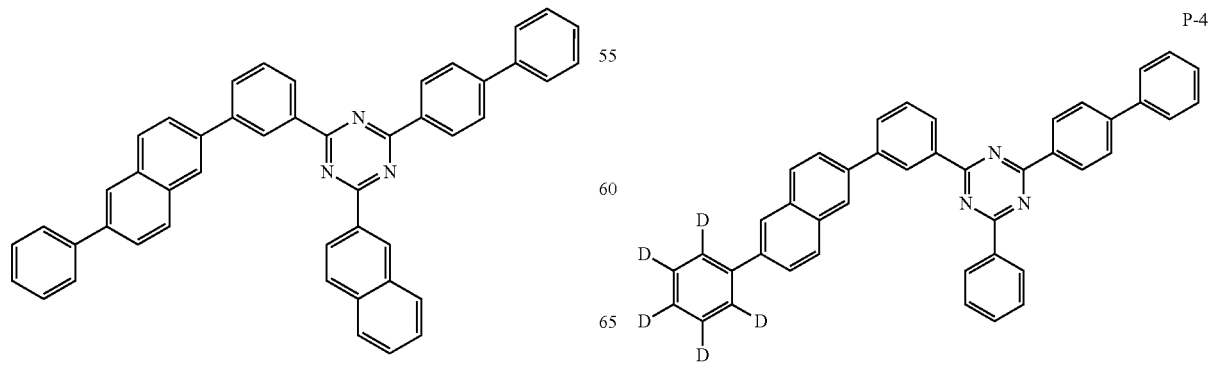

-continued
P-5
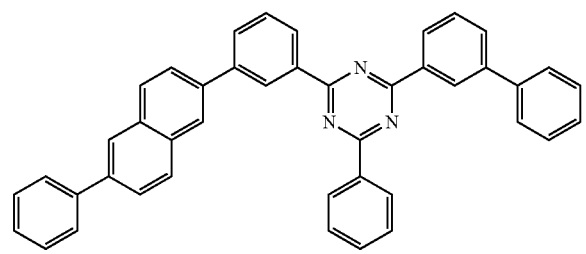
P-6
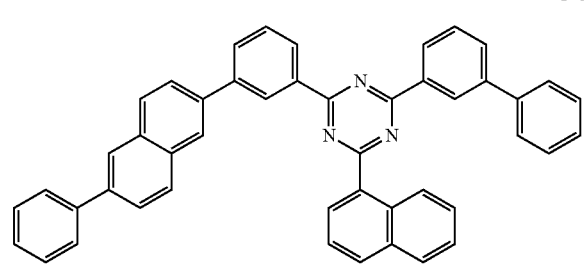
P-7
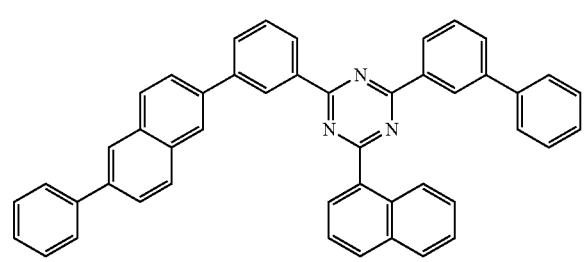
P-8
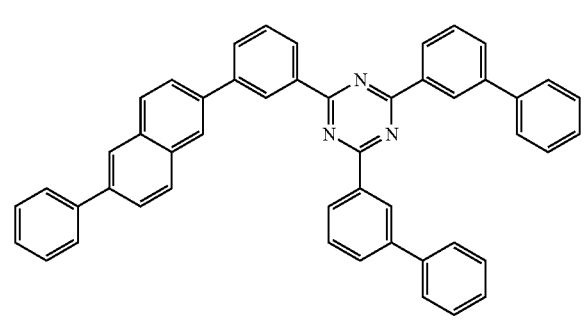
P-9
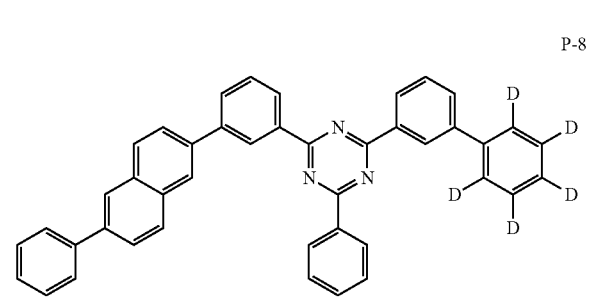
-continued
P-10
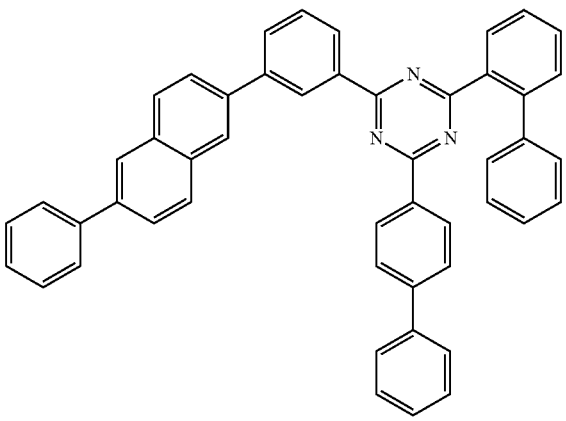
P-11
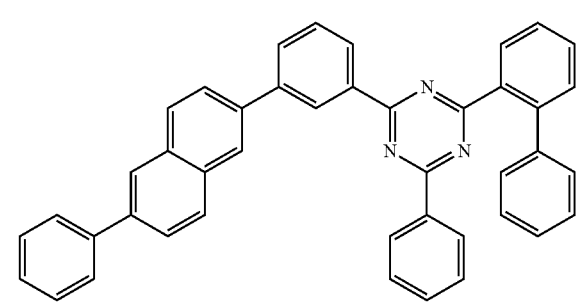
P-12
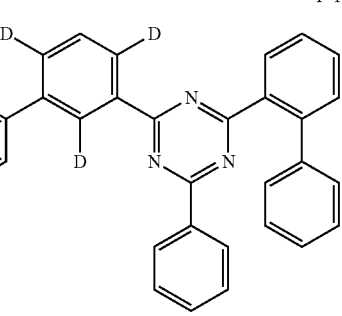
P-13
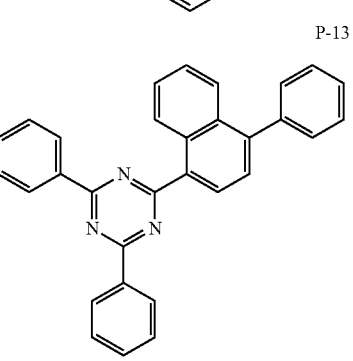

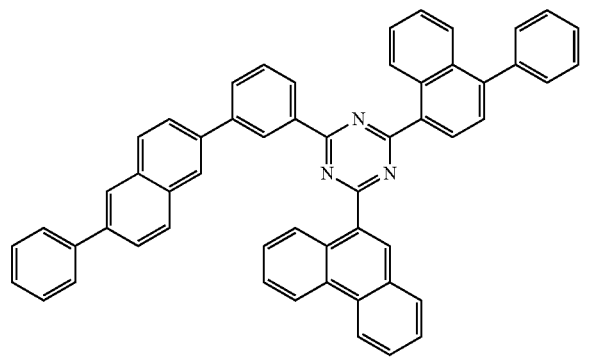
P-14
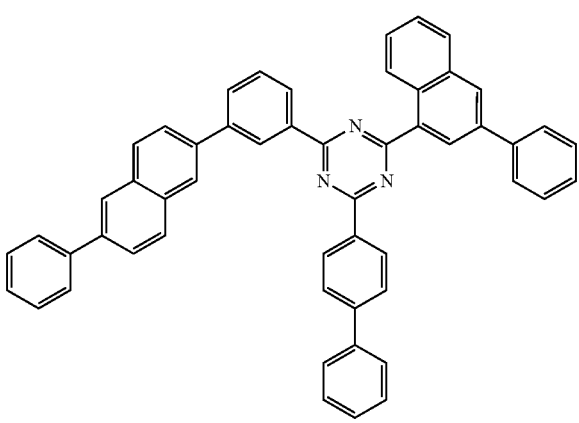
P-15, P-16
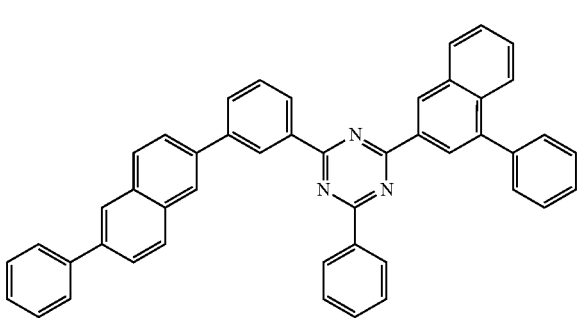
P-17
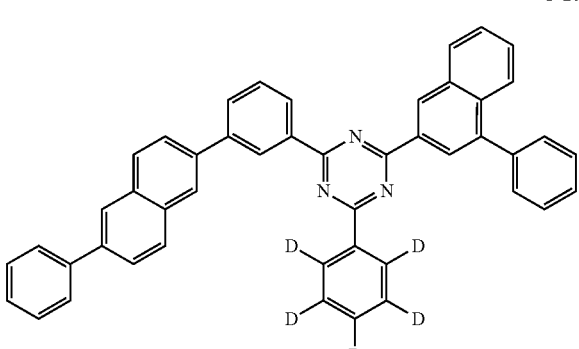
P-18
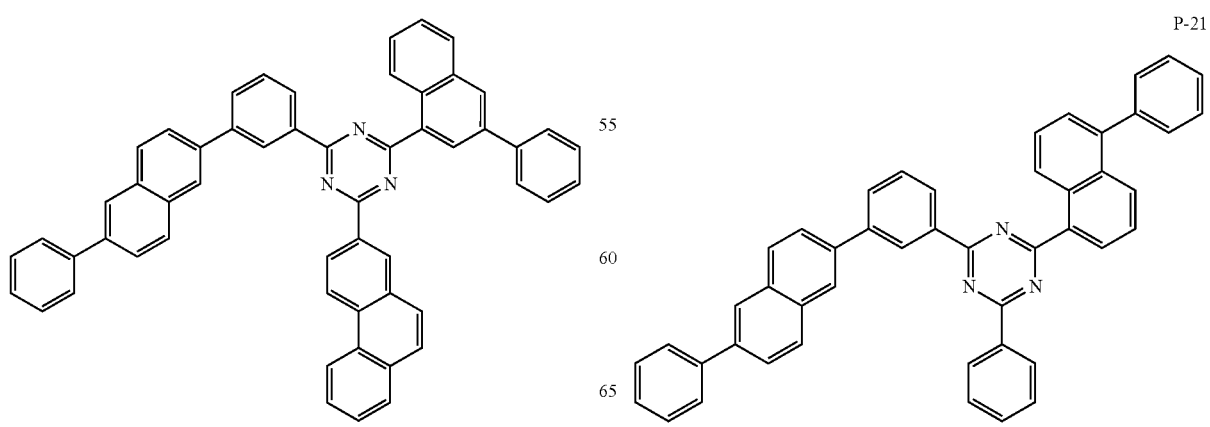
P-19, P-20, P-21

-continued

P-22

P-23

P-24

P-25

P-26

P-27

P-28
P-29
P-30
P-31
P-32
P-33
P-34
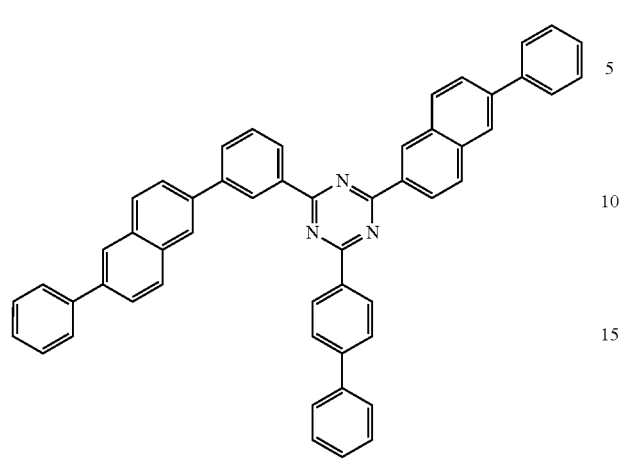
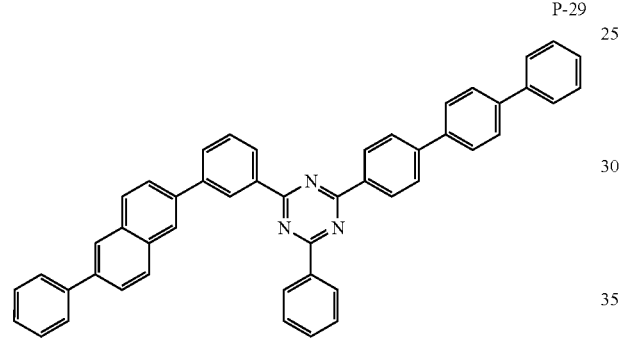
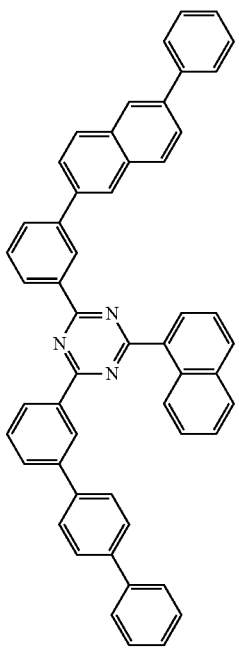
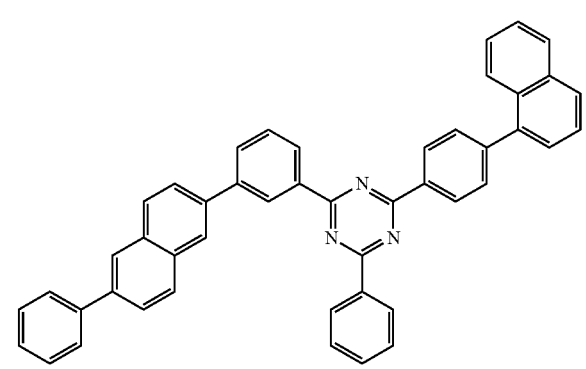
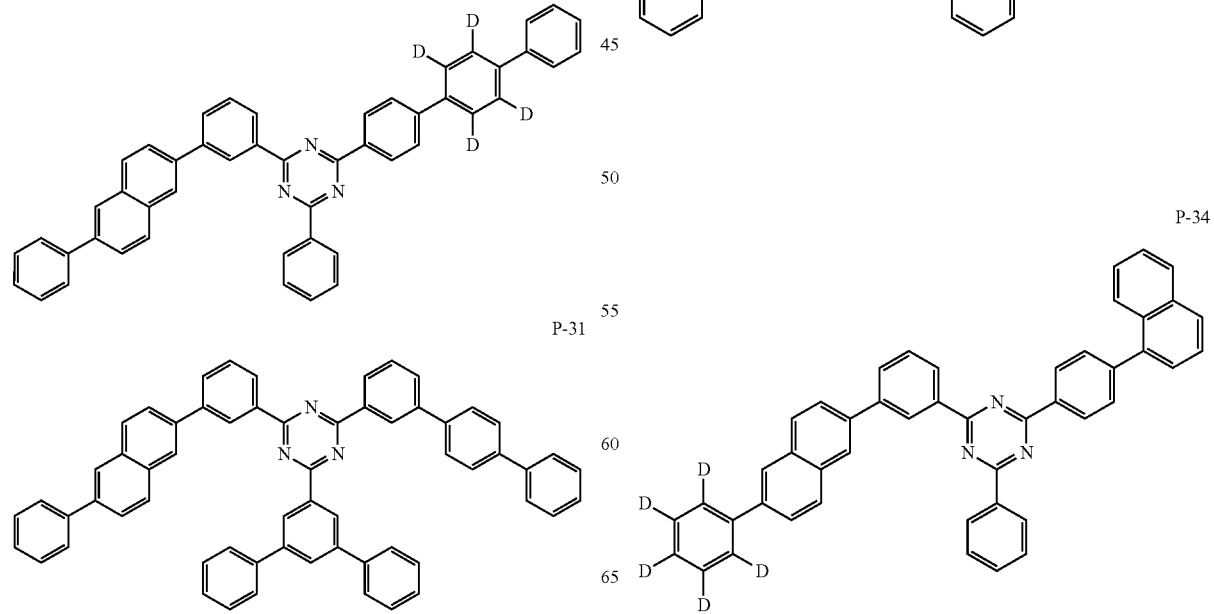

P-35
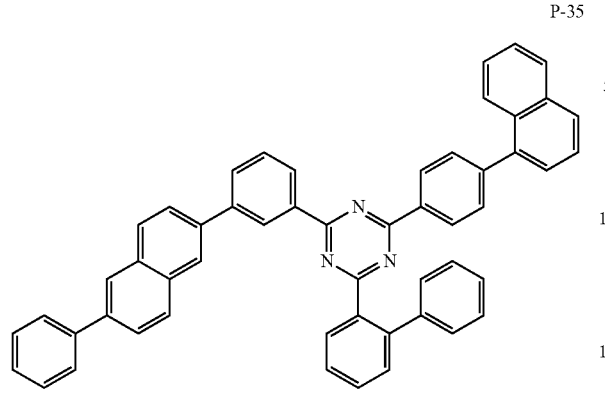
P-38
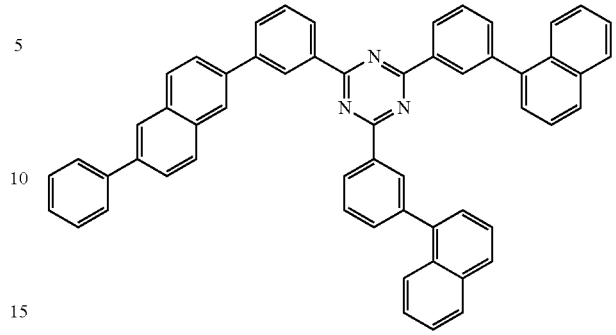
P-36
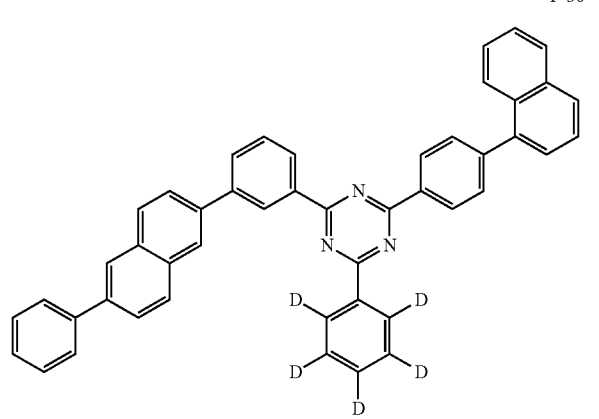
P-39
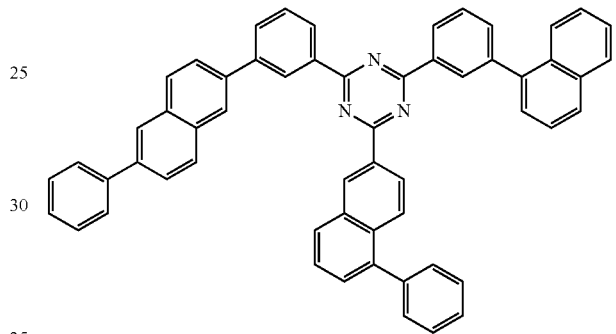
P-37
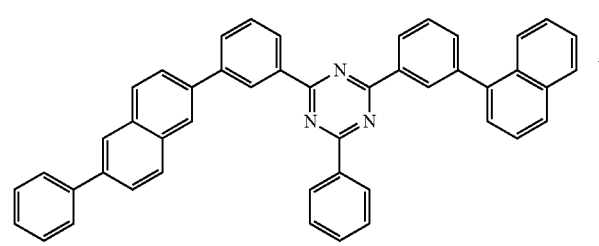
P-40
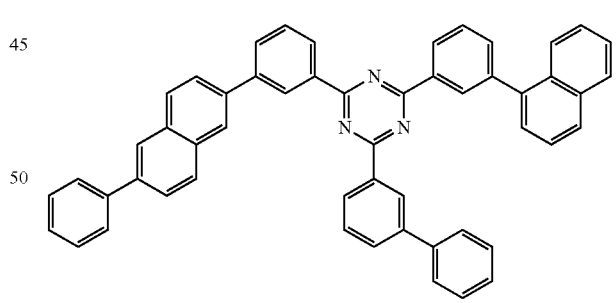
P-38
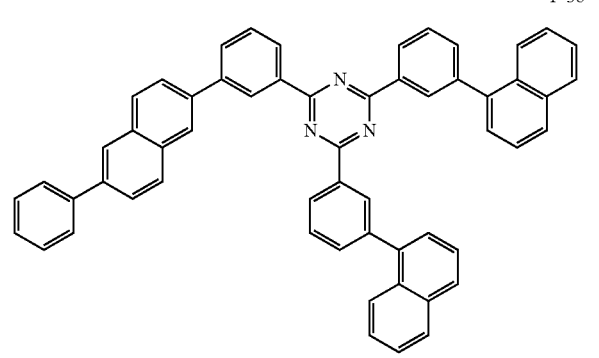
P-41
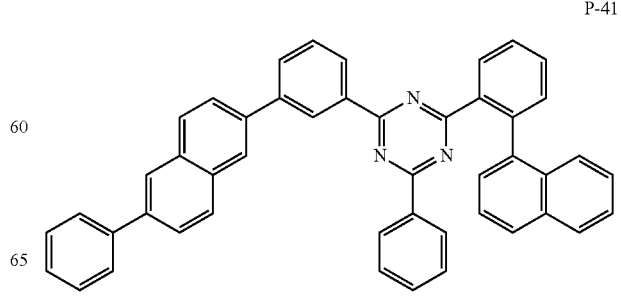

P-42

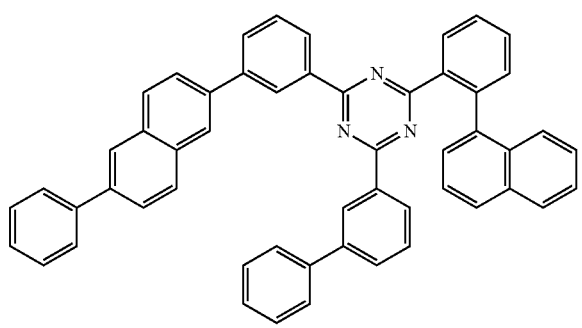

P-43

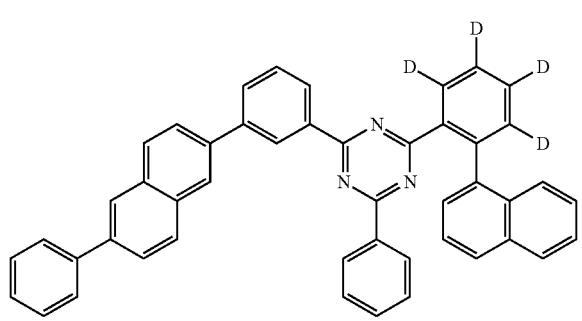

P-44

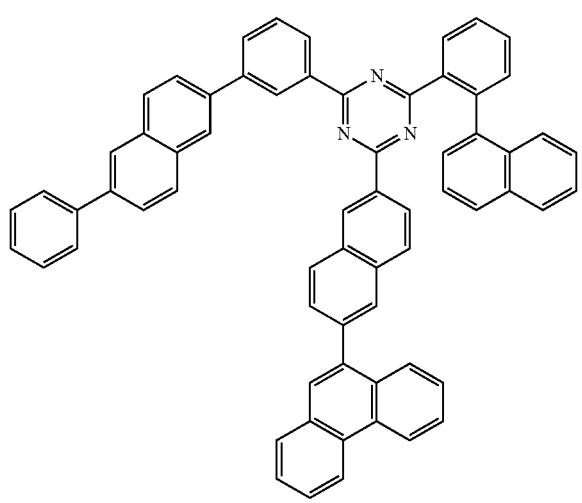

Referring to FIG. 1, the organic electronic element (100) according to the present invention includes a first electrode (110), a second electrode (170), and an organic material layer including a single compound or 2 or more compounds represented by Formula 1 between the first electrode (110) and the second electrode (170). In this case, the first electrode (110) may be an anode, and the second electrode (170) may be a cathode. In the case of an inverted type, the first electrode may be a cathode and the second electrode may be an anode.

Figure 2:
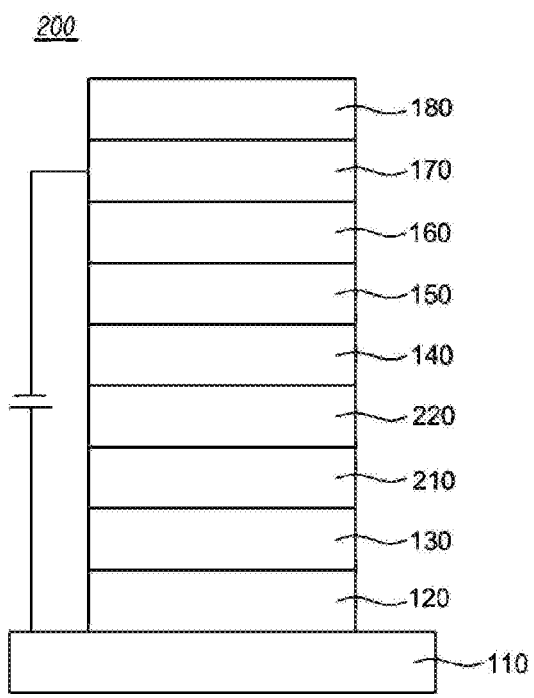

The organic material layer may sequentially include a hole injection layer (120), a hole transport layer (130), an emitting layer (140), an electron transport layer (150), and an electron injection layer (160) on the first electrode (110). In this case, the remaining layers except for the emitting layer (140) may not be formed. It may further include a hole blocking layer, an electron blocking layer, an emitting-auxiliary layer (220), a buffer layer (210), etc. and the electron transport layer (150) and the like may serve as a hole blocking layer. (See FIG. 2)

Also, the organic electronic element according to an embodiment of the present invention may further include a protective layer or a light efficiency enhancing layer (180). The light efficiency enhancing layer may be formed on one of both surfaces of the first electrode not in contact with the organic material layer or on one of both surfaces of the second electrode not in contact with the organic material layer. The compound according to an embodiment of the present invention applied to the organic material layer may be used as a host or dopant of the hole injection layer (120), the hole transport layer (130), the emitting-auxiliary layer (220), electron transport auxiliary layer, the electron transport layer (150), and an electron injection layer (160), the emitting layer (140) or as a material for the hole blocking layer or the light efficiency enhancing layer. Preferably, for example, the compound according to Formula (1) of the present invention may be used as a material for an emitting layer.

Figure 3:
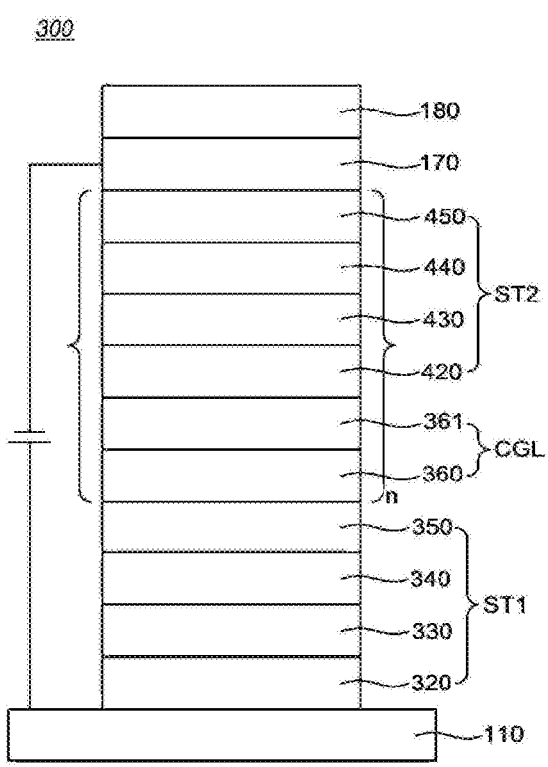

The organic material layer may comprise 2 or more stacks comprising a hole transport layer, an emitting layer and an electron transport layer sequentially formed on the anode, further include a charge generation layer formed between the 2 or more stacks (see FIG. 3).

Otherwise, even with the same core, the band gap, electrical characteristics, interface characteristics, etc. may vary depending on which position the substituent is bonded to, therefore the choice of core and the combination of sub-substituents bound thereto are also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electroluminescent device according to an embodiment of the present invention may be manufactured using a PVD (physical vapor deposition) method. For example, depositing a metal or a metal oxide having conductivity or an alloy thereof on a substrate to form an anode, and after forming an organic material layer including the hole injection layer (120), the hole transport layer (130), the emitting layer (140), the electron transport layer (150) and the electron injection layer (160) thereon, it can be prepared by depositing a material that can be used as a cathode thereon.

Also, in the present invention, the organic material layer is formed by any one of a spin coating process, a nozzle printing process, an inkjet printing process, a slot coating process, a dip coating process, and a roll-to-roll process, and the organic material layer provides an organic electronic element comprising the compound as an electron transport material.

As another specific example, the same or different compounds of the compound represented by Formula (1) are mixed and used in the organic material layer.

Also, the present invention provides a composition for an emitting layer comprising the compound represented by Formula (1), and provides an organic electronic element comprising the emitting layer.

Also, the present invention provides an electronic device comprising a display device including the organic electronic element; and a control unit for driving the display device;

In another aspect, the organic electronic element is at least one of an organic electroluminescent device, an organic solar cell, an organic photo conductor, an organic transistor, and a device for monochromatic or white lighting. At this time, the electronic device may be a current or future wired/wireless communication terminal, and covers all kinds of electronic devices including mobile communication terminals such as mobile phones, a personal digital assistant (PDA), an electronic dictionary, a point-to-multipoint (PMP), a remote controller, a navigation unit, a game player, various kinds of TVs, and various kinds of computers.

Hereinafter, a synthesis example of the compound represented by Formula (1) of the present invention and a manufacturing example of an organic electronic element of the present invention will be described in detail with reference to Examples, but the present invention is not limited to the following Examples.

Synthesis Example 1

The compound (final product) represented by Formula 1-1 according to the present invention is synthesized as shown in Reaction Scheme 1, but is not limited thereto.

<Reaction Scheme 1>

Sub1

Sub2

Final Products

I. Synthesis of Sub1

The compound belonging to Sub1 may be the following compounds, but is not limited thereto, and Table 1 below shows FD-MS (Field Desorption-Mass Spectrometry) values of the compounds belonging to Sub1.

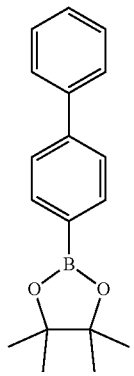

Sub 1-1

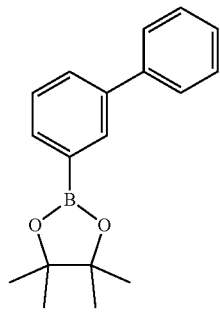

Sub 1-2

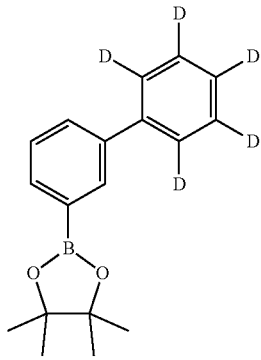

Sub 1-3

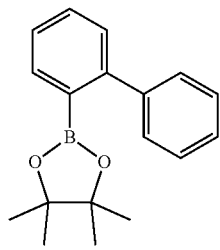

Sub 1-4

-continued
Sub 1-5
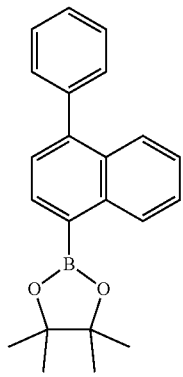
Sub 1-6
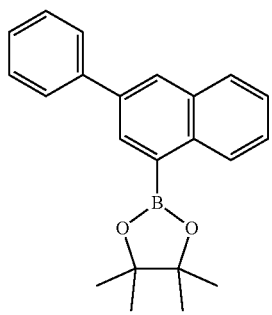
Sub 1-7
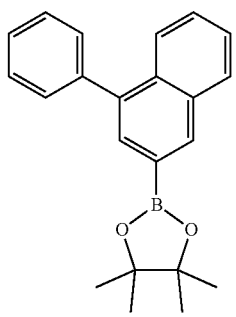
Sub 1-8
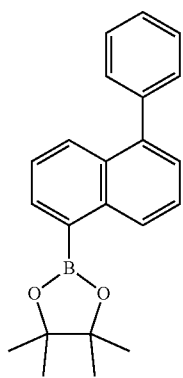
Sub 1-9
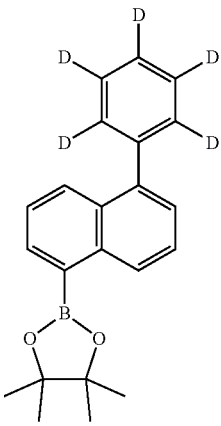
Sub 1-10
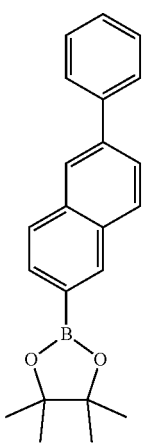
Sub 1-11
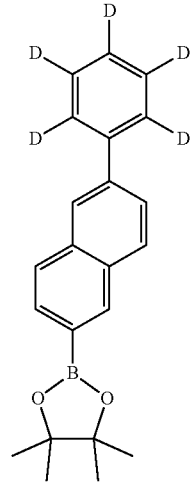

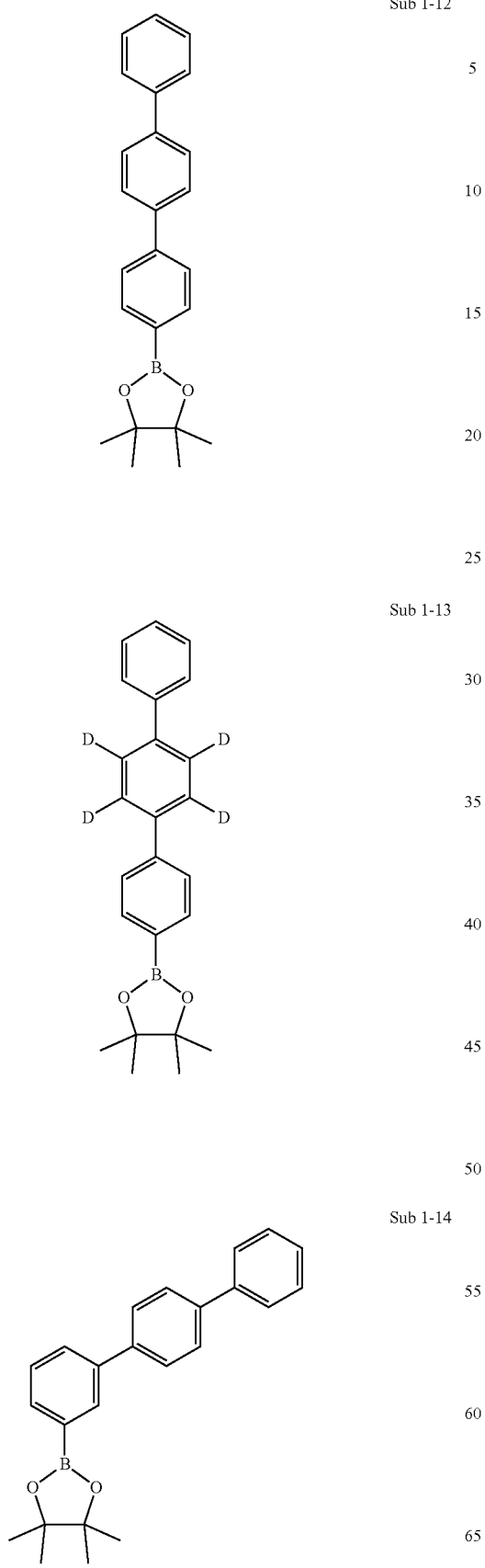
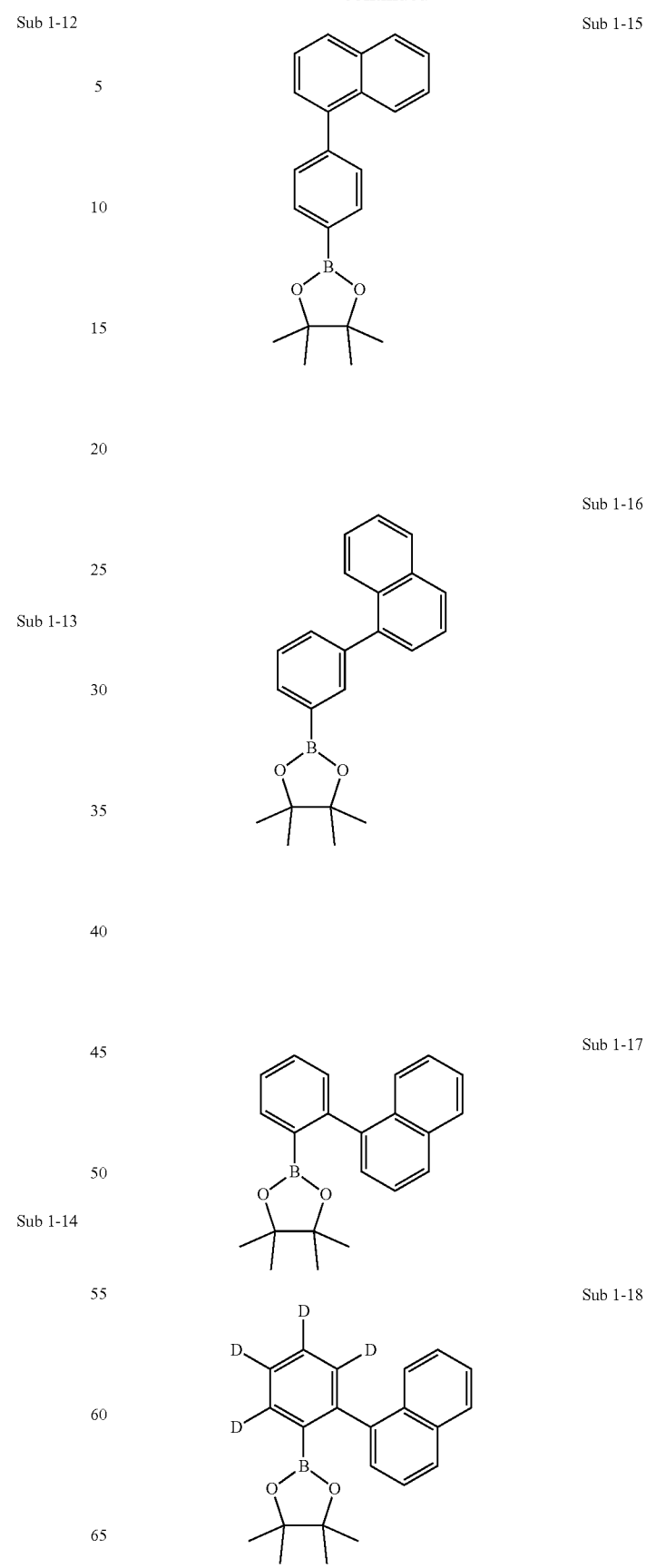

Sub 1-19
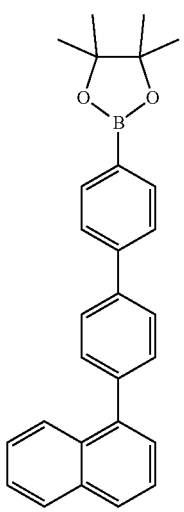
Sub 1-22
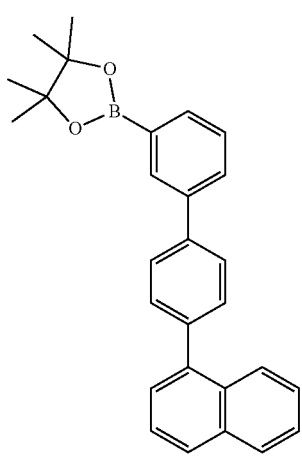
Sub 1-20
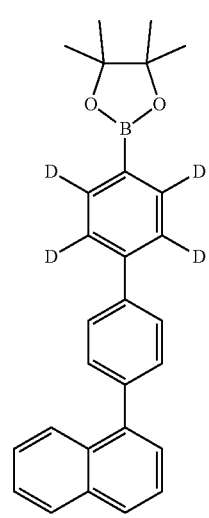
Sub 1-23
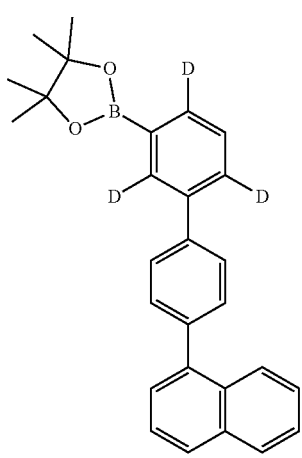
Sub 1-21
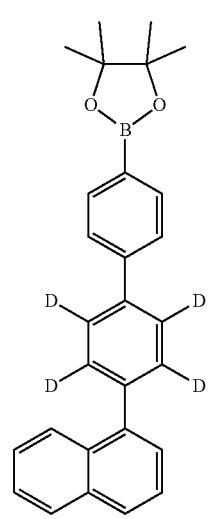
Sub 1-24
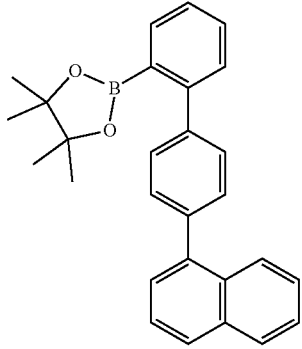

-continued

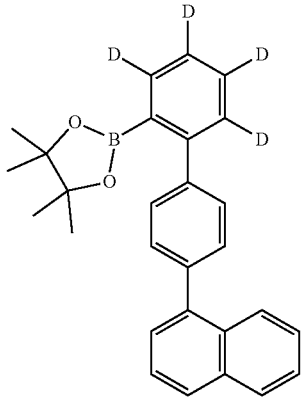
Sub 1-25

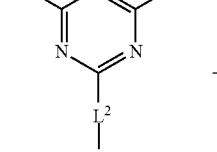
Sub2b

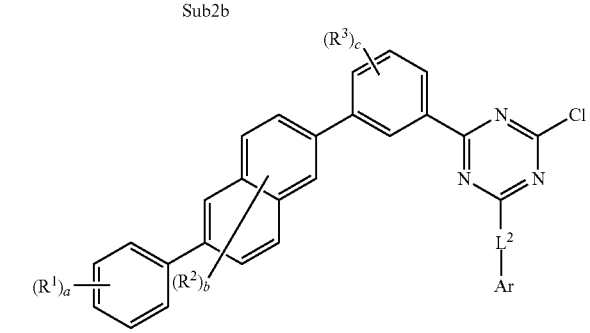
Sub2

1. Synthesis Example of Sub2-1

TABLE 1

| compound | FD-MS |
|---|---|
| Sub1-1 | m/z = 280.16($C_{18}H_{21}BO_2$ = 280.17) |
| Sub1-2 | m/z = 280.16($C_{18}H_{21}BO_2$ = 280.17) |
| Sub1-3 | m/z = 285.19($C_{18}H_{16}D_5BO_2$ = 285.2) |
| Sub1-4 | m/z = 280.16($C_{18}H_{21}BO_2$ = 280.17) |
| Sub1-5 | m/z = 330.18($C_{22}H_{23}BO_2$ = 330.23) |
| Sub1-6 | m/z = 330.18($C_{22}H_{23}BO_2$ = 330.23) |
| Sub1-7 | m/z = 330.18($C_{22}H_{23}BO_2$ = 330.23) |
| Sub1-8 | m/z = 330.18($C_{22}H_{23}BO_2$ = 330.23) |
| Sub1-9 | m/z = 335.21($C_{22}H_{18}D_5BO_2$ = 335.26) |
| Sub1-10 | m/z = 330.18($C_{22}H_{23}BO_2$ = 330.23) |
| Sub1-11 | m/z = 335.21($C_{22}H_{18}D_5BO_2$ = 335.26) |
| Sub1-12 | m/z = 356.19($C_{24}H_{25}BO_2$ = 356.27) |
| Sub1-13 | m/z = 360.22($C_{24}H_{21}D_4BO_2$ = 360.3) |
| Sub1-14 | m/z = 356.19($C_{24}H_{25}BO_2$ = 356.27) |
| Sub1-15 | m/z = 330.18($C_{22}H_{23}BO_2$ = 330.23) |
| Sub1-16 | m/z = 330.18($C_{22}H_{23}BO_2$ = 330.23) |
| Sub1-17 | m/z = 330.18($C_{22}H_{23}BO_2$ = 330.23) |
| Sub1-18 | m/z = 334.2($C_{22}H_{19}D_4BO_2$ = 334.26) |
| Sub1-19 | m/z = 406.21($C_{28}H_{27}BO_2$ = 406.33) |
| Sub1-20 | m/z = 410.24($C_{28}H_{23}D_4BO_2$ = 410.36) |
| Sub1-21 | m/z = 410.24($C_{28}H_{23}D_4BO_2$ = 410.36) |
| Sub1-22 | m/z = 406.21($C_{28}H_{27}BO_3$ = 406.33) |
| Sub1-23 | m/z = 409.23($C_{28}H_{24}D_3BO_2$ = 409.35) |
| Sub1-24 | m/z = 406.21($C_{28}H_{27}BO_2$ = 406.33) |
| Sub1-25 | m/z = 410.24($C_{28}H_{23}D_4BO_2$ = 410.36) |

II. Synthesis of Sub2

Sub2 of Reaction Scheme 1 is synthesized by the reaction route of Reaction Scheme 2, but is not limited thereto.

<Reaction Scheme 2>

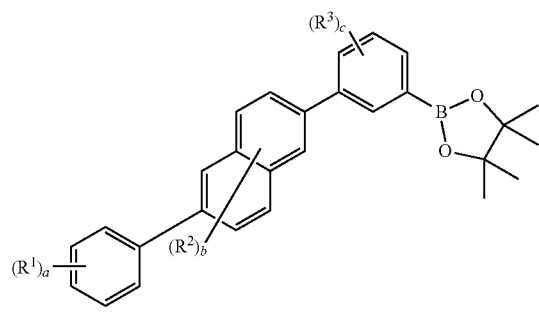
Sub2a

+

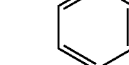
Sub2a-1

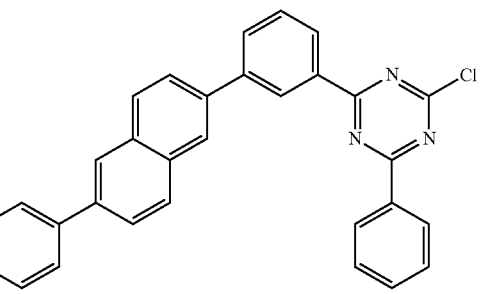
Sub2b-1

Sub2-1

After dissolving Sus2b-1 (13.9 g, 61.5 mmol) in THF (Tetrahydrofuran) (310 mL) in a round-bottom flask, Sub2a-1 (25.0 g, 61.5 mmol), NaOH (7.4 g, 184.6 mmol), Pd(PPh₃)₄ (4.27 g, 3.69 mmol) and Water (155 mL) were added and stirred at 80° C. When the reaction was completed, the mixture was extracted with CH₂Cl₂ and water, and the organic layer was dried over MgSO₄ and concentrated. The resulting compound was recrystallized by silicagel column to obtain 21.5 g (yield 74.5%) of the product.

2. Synthesis Example of Sub2-2

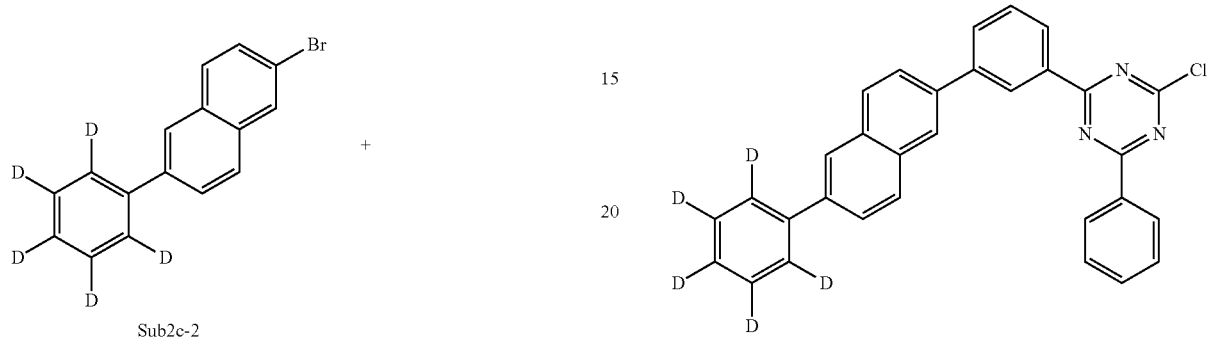

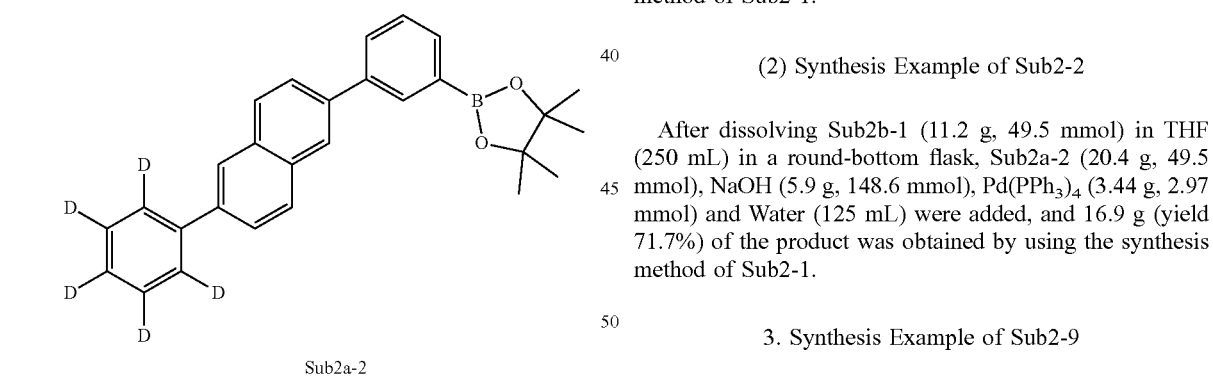

(1) Synthesis Example of Sub2a-2

After dissolving Sub2d-2 (22.9 g, 69.4 mmol) in THF (350 mL) in a round-bottom flask, Sub2c-1 (20.0 g, 69.4 mmol), NaOH (8.3 g, 208.2 mmol), Pd(PPh₃)₄ (4.81 g, 4.16 mmol) and Water (175 mL) were added, and 20.4 g (yield 71.4%) of the product was obtained by using the synthesis method of Sub2-1.

(2) Synthesis Example of Sub2-2

After dissolving Sub2b-1 (11.2 g, 49.5 mmol) in THF (250 mL) in a round-bottom flask, Sub2a-2 (20.4 g, 49.5 mmol), NaOH (5.9 g, 148.6 mmol), Pd(PPh₃)₄ (3.44 g, 2.97 mmol) and Water (125 mL) were added, and 16.9 g (yield 71.7%) of the product was obtained by using the synthesis method of Sub2-1.

3. Synthesis Example of Sub2-9

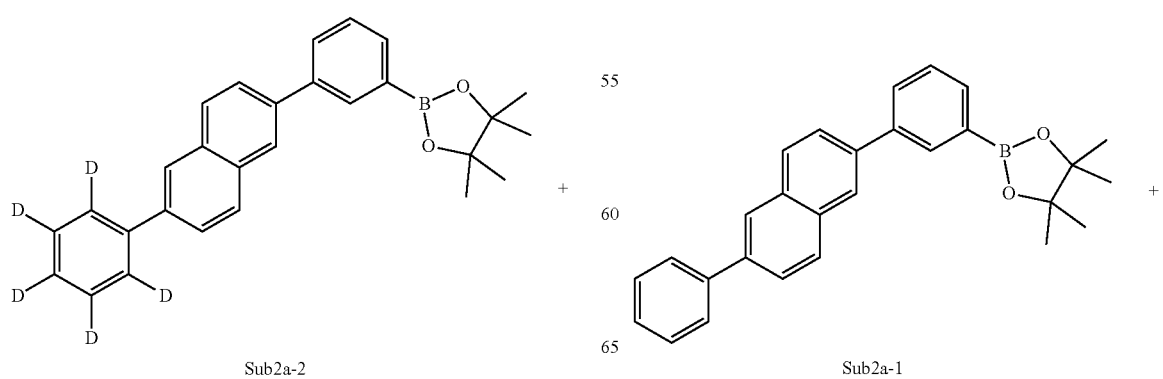

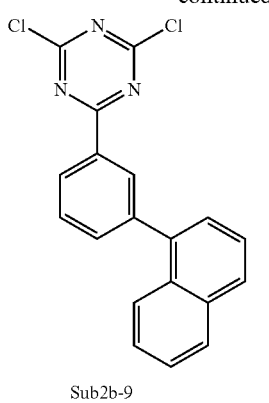

Sub2b-9

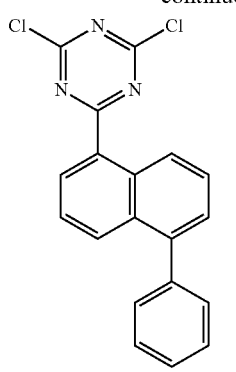

Sub2b-13

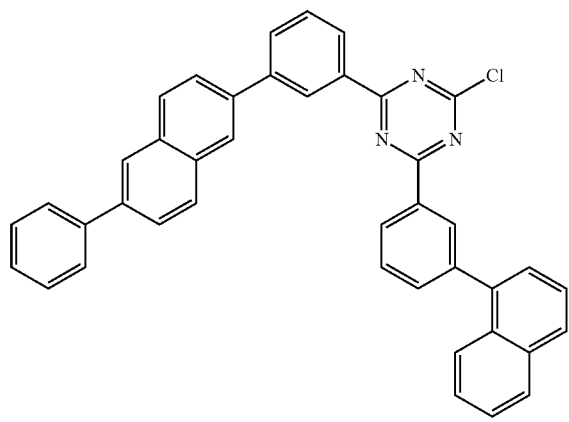

Sub2-9

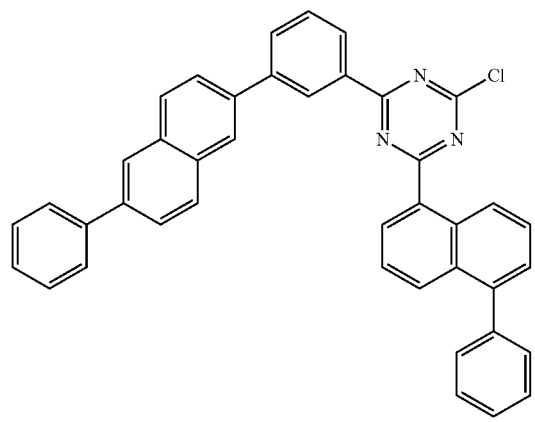

Sub2-13

After dissolving Sub2b-9 (13.0 g, 36.9 mmol) in THF (185 mL) in a round-bottom flask, Sub2a-1 (15.0 g, 36.9 mmol), NaOH (4.4 g, 110.7 mmol), Pd(PPh$_3$)$_4$ (2.56 g, 2.21 mmol) and Water (92 mL) were added, and 16.1 g (yield 73.3%) of the product was obtained by using the synthesis method of Sub2-1.

4. Synthesis Example of Sub2-13

After dissolving Sub2b-13 (13.0 g, 36.9 mmol) in THF (185 mL) in a round-bottom flask, Sub2a-1 (15.0 g, 36.9 mmol), NaOH (4.4 g, 110.7 mmol), Pd(PPh$_3$)$_4$ (2.56 g, 2.21 mmol) and Water (92 mL) were added, and 16.0 g (yield 72.7%) of the product was obtained by using the synthesis method of Sub2-1.

The compound belonging to Sub2 may be a compound as follows, but is not limited thereto, Table 2 below shows FD-MS (Field Desorption-Mass Spectrometry) values of some compounds belonging to Sub2.

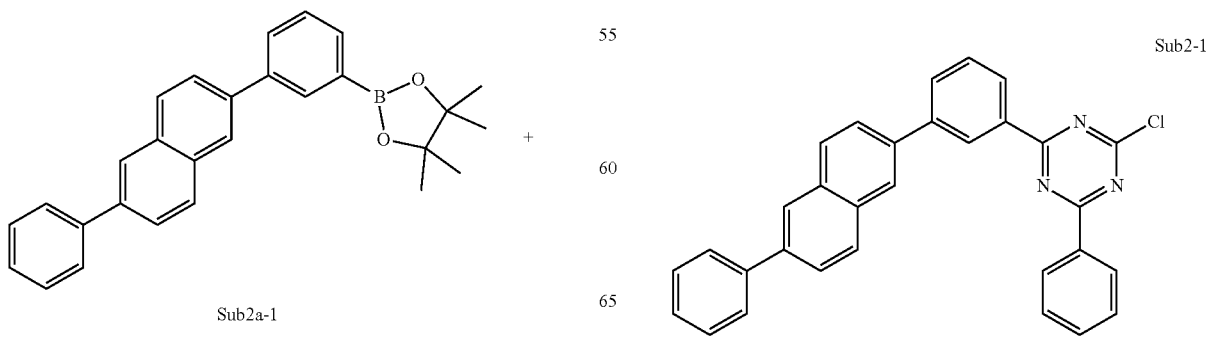

Sub2a-1

Sub2-1

Sub2-2
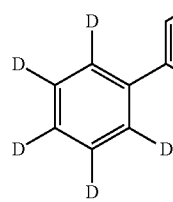
Sub2-6
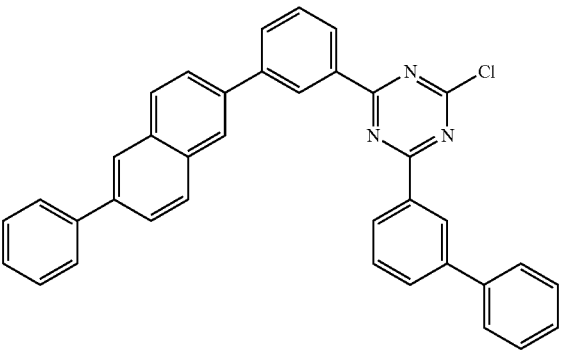
Sub2-3
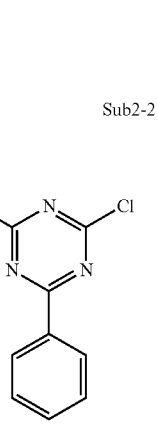
Sub2-7
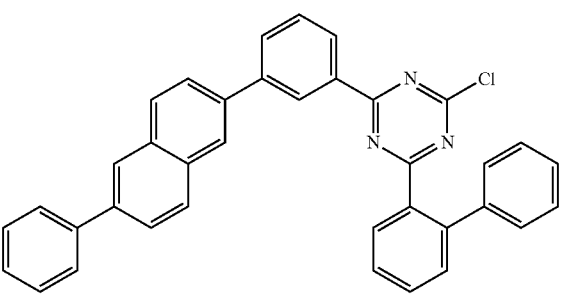
Sub2-4
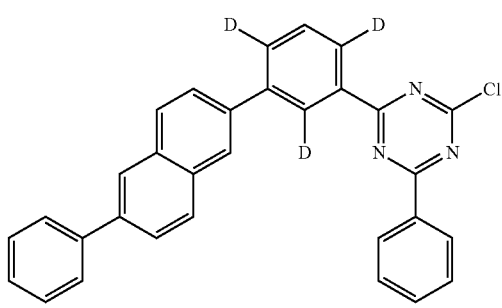
Sub2-8
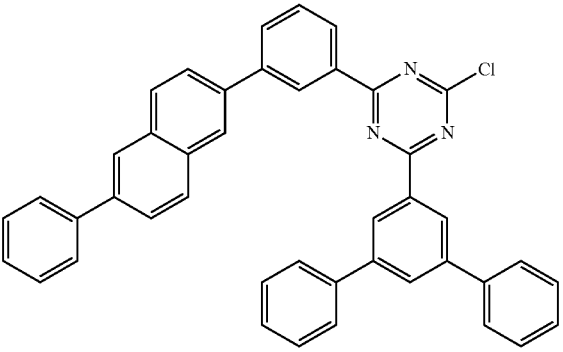
Sub2-5
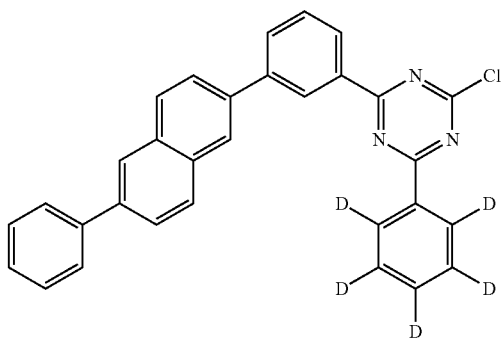
Sub2-9
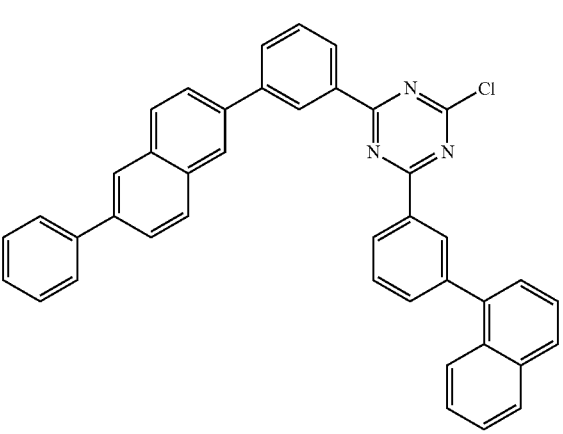
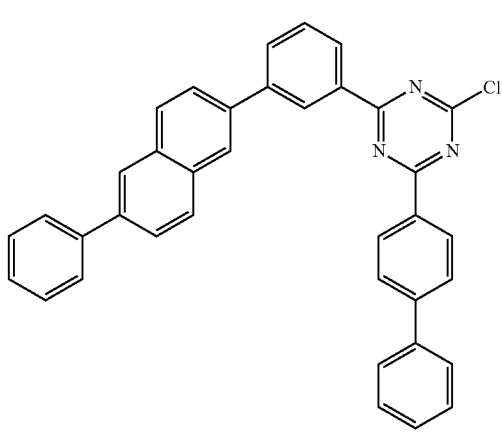

Sub2-10
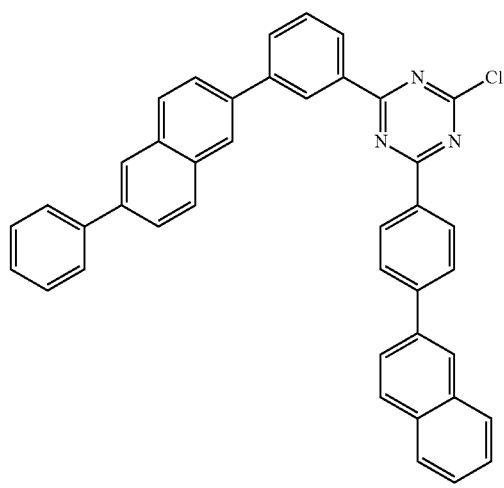
Sub2-11
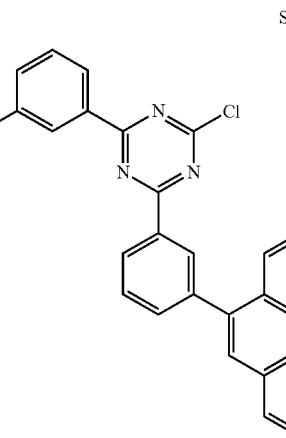
Sub2-12
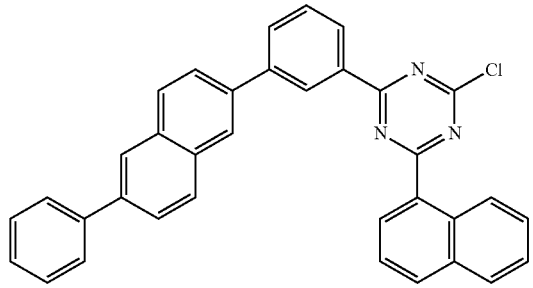
Sub2-13
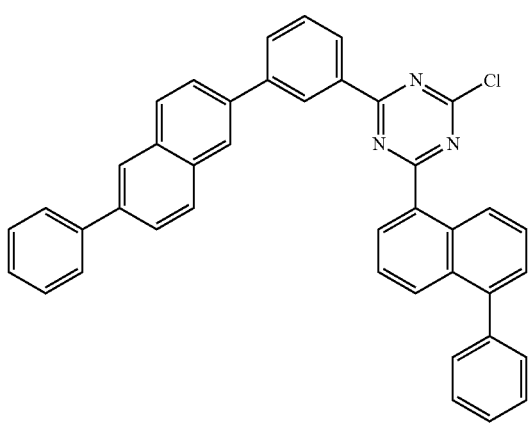
Sub2-14
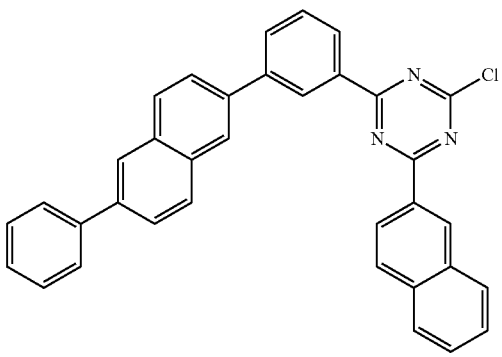
Sub2-15
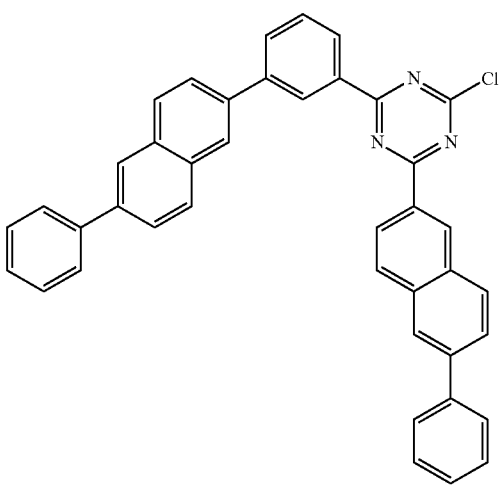

Sub2-16

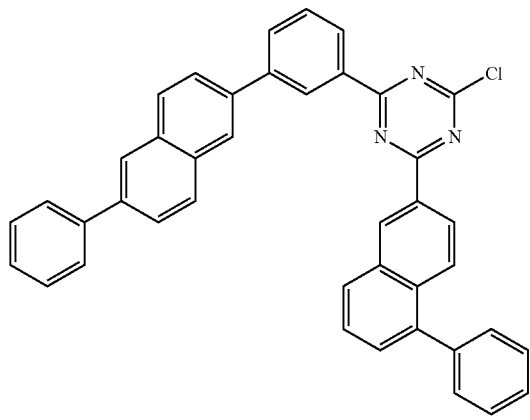

Sub2-17

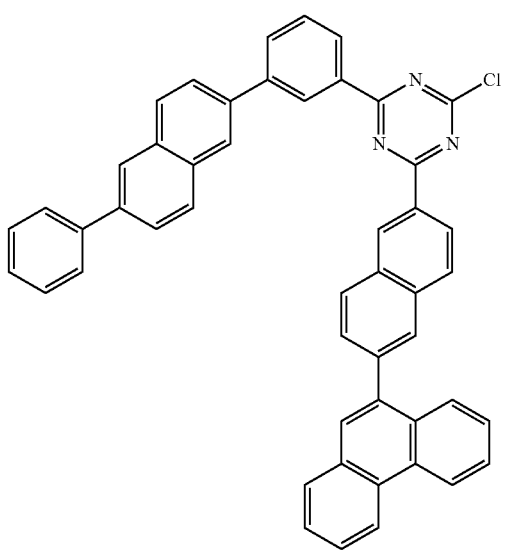

Sub2-18

Sub2-19

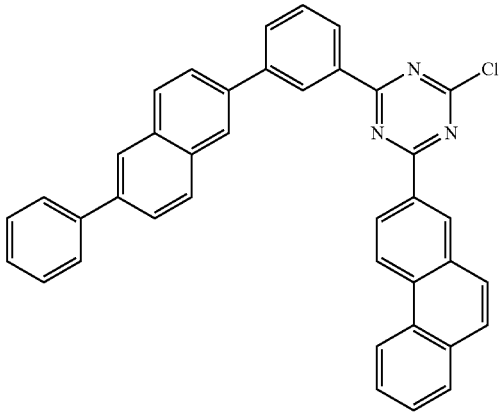

TABLE 2

| compound | FD-MS |
|---|---|
| Sub2-1 | m/z = 469.13($C_{31}H_{20}ClN_3$ = 469.97) |
| Sub2-2 | m/z = 474.17($C_{31}H_{15}D_5ClN_3$ = 475.00) |
| Sub2-3 | m/z = 472.15($C_{31}H_{17}D_3ClN_3$ = 472.99) |
| Sub2-4 | m/z = 474.17($C_{31}H_{15}D_5ClN_3$ = 475.00) |
| Sub2-5 | m/z = 545.17($C_{37}H_{24}ClN_3$ = 546.07) |
| Sub2-6 | m/z = 545.17($C_{37}H_{34}ClN_3$ = 546.07) |
| Sub2-7 | m/z = 545.17($C_{37}H_{24}ClN_3$ = 546.07) |
| Sub2-8 | m/z = 621.20($C_{43}H_{28}ClN_3$ = 622.17) |
| Sub2-9 | m/z = 595.18($C_{41}H_{26}ClN_3$ = 596.13) |
| Sub2-10 | m/z = 595.18($C_{41}H_{26}ClN_3$ = 596.13) |
| Sub2-11 | m/z = 645.20($C_{45}H_{28}ClN_3$ = 646.19) |
| Sub2-12 | m/z = 519.15($C_{35}H_{22}ClN_3$ = 520.03) |
| Sub2-13 | m/z = 595.18($C_{41}H_{26}ClN_3$ = 596.13) |
| Sub2-14 | m/z = 519.15($C_{35}H_{22}ClN_3$ = 520.03) |
| Sub2-15 | m/z = 595.18($C_{41}H_{26}ClN_3$ = 596.13) |
| Sub2-16 | m/z = 595.18($C_{41}H_{26}ClN_3$ = 596.13) |
| Sub2-17 | m/z = 695.21($C_{49}H_{30}ClN_3$ = 696.25) |
| Sub2-18 | m/z = 569.17($C_{39}H_{24}ClN_3$ = 570.09) |
| Sub2-19 | m/z = 569.17($C_{39}H_{24}ClN_3$ = 570.09) |

III. Synthesis of Final Product

1. Synthesis Example of P-1

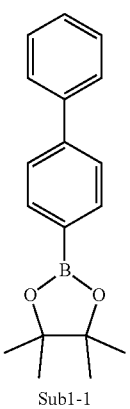

+

Sub1-1

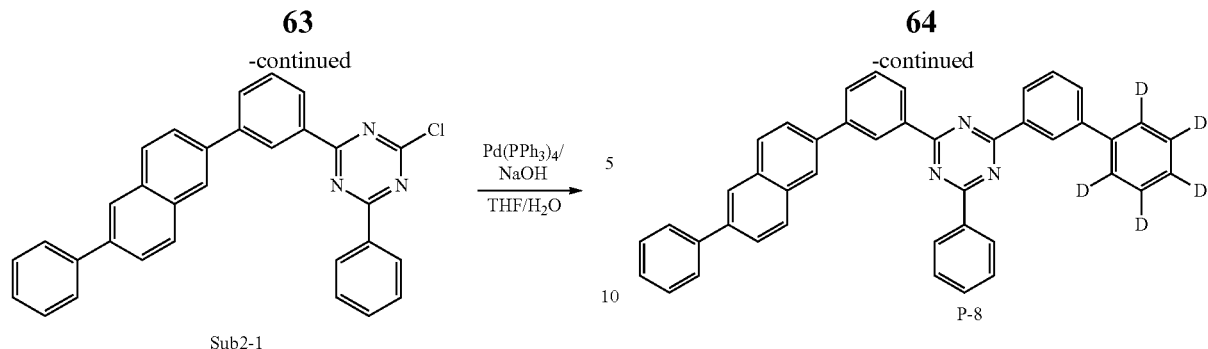

After dissolving Sus2-1 (5.0 g, 10.7 mmol) in THF (Tetrahydrofuran) (54 mL) in a round-bottom flask, Sub1-1 (3.0 g, 10.7 mmol), NaOH (1.3 g, 32.1 mmol), Pd(PPh$_3$)$_4$ (0.74 g, 0.64 mmol) and Water (27 mL) were added and stirred at 80° C. When the reaction was completed, the mixture was extracted with CH$_2$Cl$_2$ and water, and the organic layer was dried over MgSO$_4$ and concentrated. The resulting compound was recrystallized by silicagel column to obtain 4.8 g (yield 77%) of the product.

2. Synthesis Example of P-8

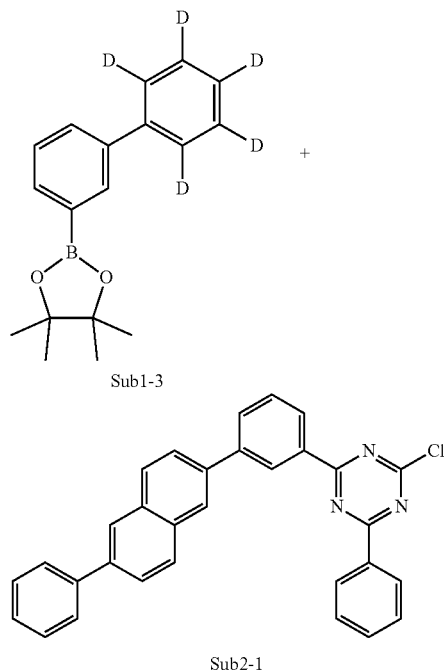

After dissolving Sus2-1 (4.9 g, 10.5 mmol) in THF (Tetrahydrofuran) (53 mL) in a round-bottom flask, Sub1-3 (3.0 g, 10.5 mmol), NaOH (1.3 g, 31.6 mmol), Pd(PPh$_3$)$_4$ (0.73 g, 0.63 mmol) and Water (26 mL) were added, and 4.6 g (yield 74%) of the product was obtained using the above synthesis method of P-1.

3. Synthesis Example of P-9

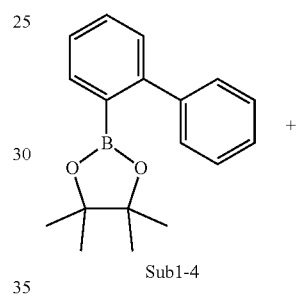

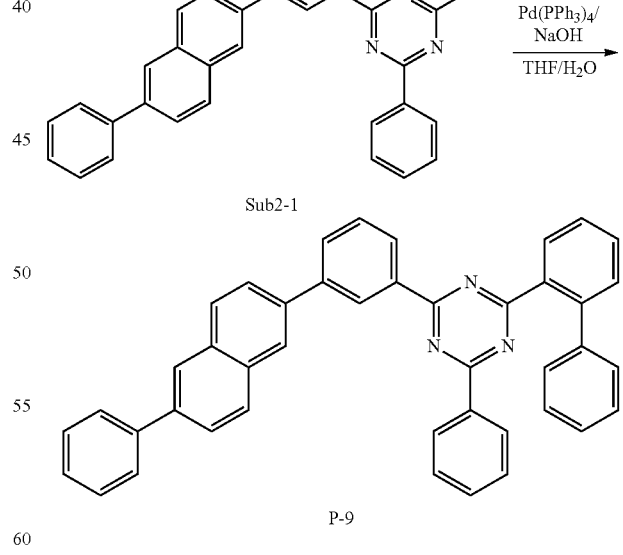

After dissolving Sus2-1 (5.0 g, 10.7 mmol) in THF (Tetrahydrofuran) (54 mL) in a round-bottom flask, Sub1-4 (3.0 g, 10.7 mmol), NaOH (1.3 g, 32.1 mmol), Pd(PPh$_3$)$_4$ (0.74 g, 0.64 mmol) and Water (27 mL) were added, and 4.5 g (yield 71%) of the product was obtained using the above synthesis method of P-1.

4. Synthesis Example of P-16

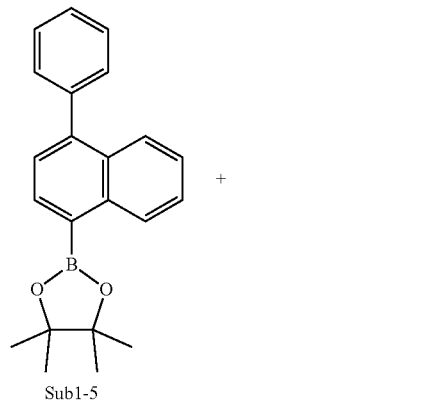

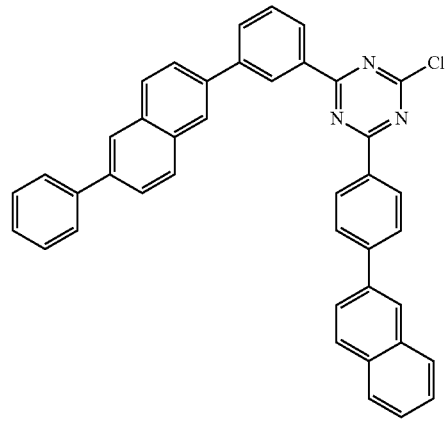

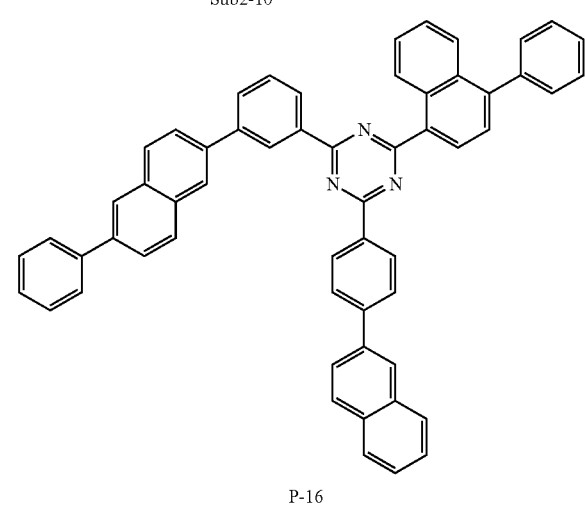

After dissolving Sus2-10 (5.4 g, 9.1 mmol) in THF (Tetrahydrofuran) (45 mL) in a round-bottom flask, Sub1-5 (3.0 g, 9.1 mmol), NaOH (1.1 g, 27.3 mmol), Pd(PPh$_3$)$_4$ (0.63 g, 0.55 mmol) and Water (23 mL) were added, and 5.0 g (yield 72%) of the product was obtained using the above synthesis method of P-1.

5. Synthesis Example of P-19

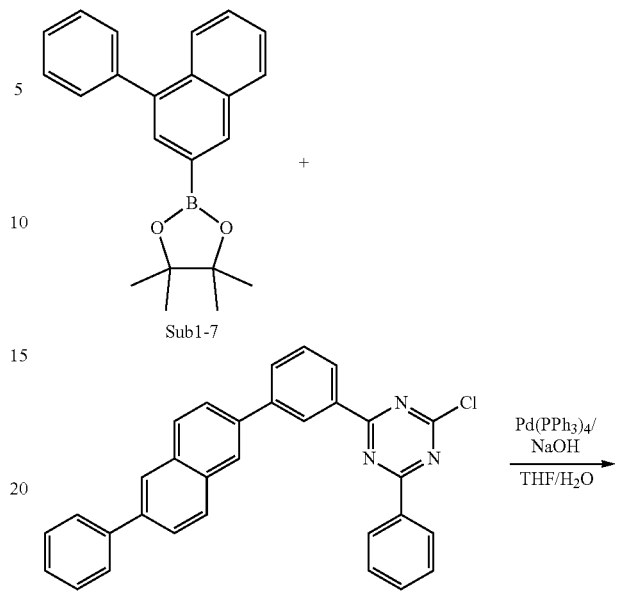

After dissolving Sus2-1 (4.3 g, 9.1 mmol) in THF (Tetrahydrofuran) (45 mL) in a round-bottom flask, Sub1-7 (3.0 g, 9.1 mmol), NaOH (1.1 g, 27.3 mmol), Pd(PPh$_3$)$_4$ (0.63 g, 0.55 mmol) and Water (23 mL) were added, and 4.3 g (yield 75%) of the product was obtained using the above synthesis method of P-1.

6. Synthesis Example of P-22

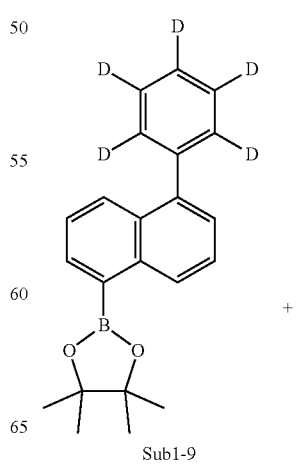

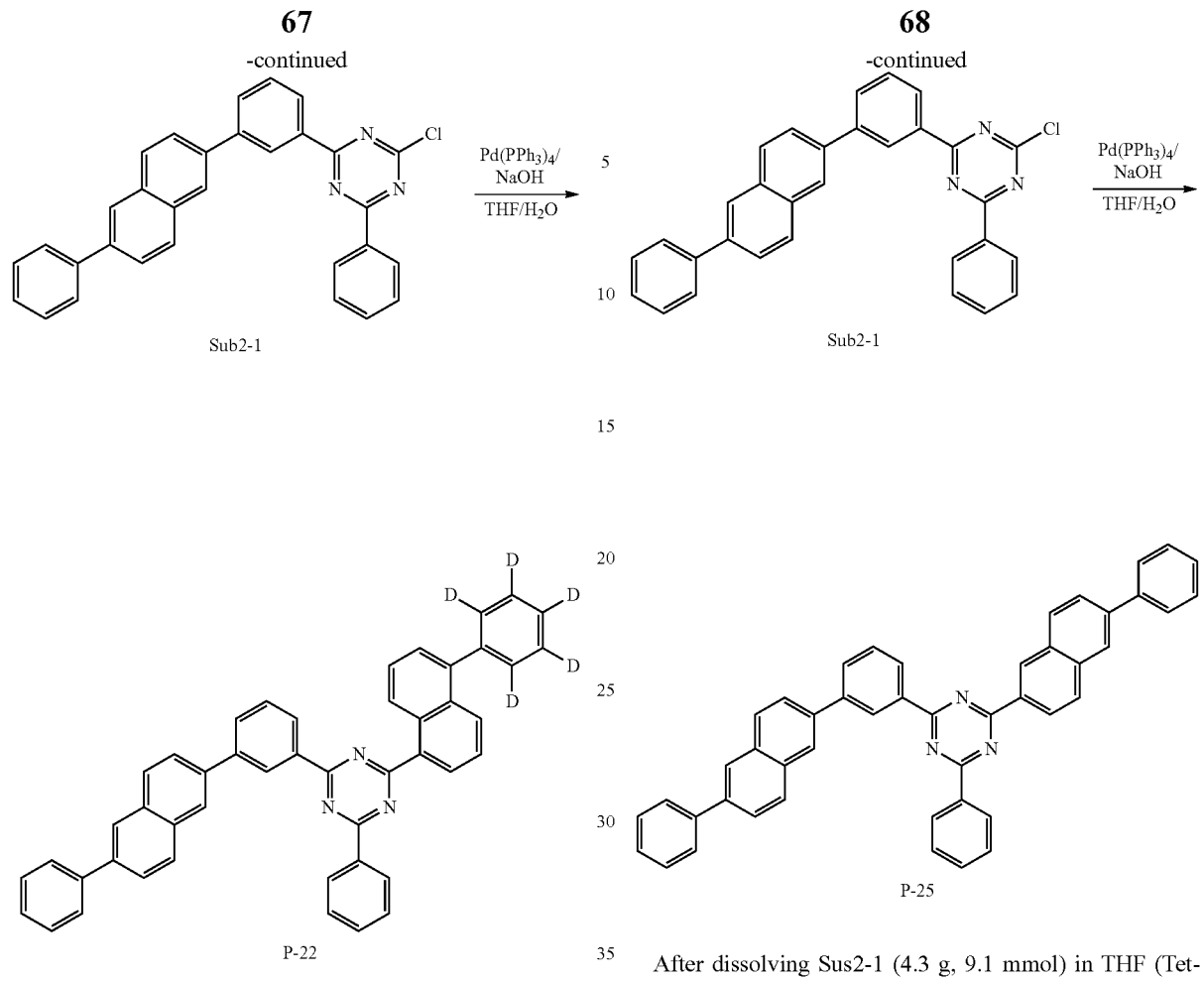

After dissolving Sus2-1 (4.2 g, 8.9 mmol) in THF (Tetrahydrofuran) (45 mL) in a round-bottom flask, Sub1-9 (3.0 g, 8.9 mmol), NaOH (1.1 g, 26.8 mmol), Pd(PPh$_3$)$_4$ (0.62 g, 0.54 mmol) and Water (22 mL) were added, and 4.2 g (yield 73%) of the product was obtained using the above synthesis method of P-1.

7. Synthesis Example of P-25

After dissolving Sus2-1 (4.3 g, 9.1 mmol) in THF (Tetrahydrofuran) (45 mL) in a round-bottom flask, Sub1-10 (3.0 g, 9.1 mmol), NaOH (1.1 g, 27.3 mmol), Pd(PPh$_3$)$_4$ (0.63 g, 0.55 mmol) and Water (23 mL) were added, and 4.5 g (yield 77%) of the product was obtained using the above synthesis method of P-1.

8. Synthesis Example of P-30

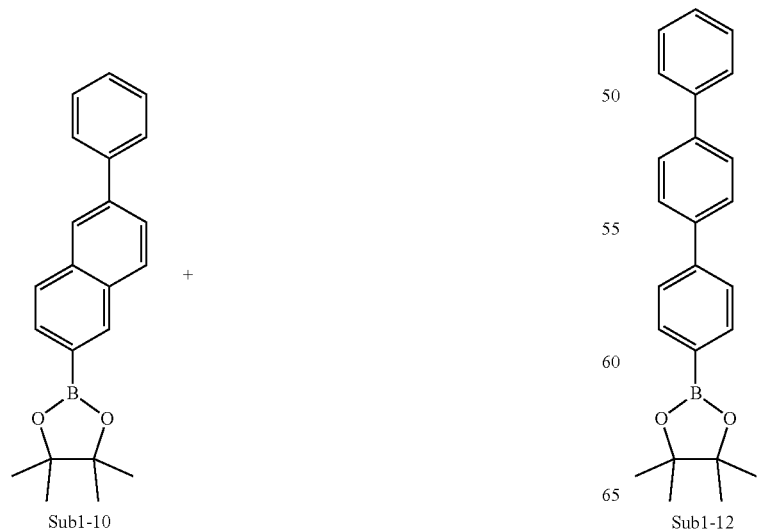

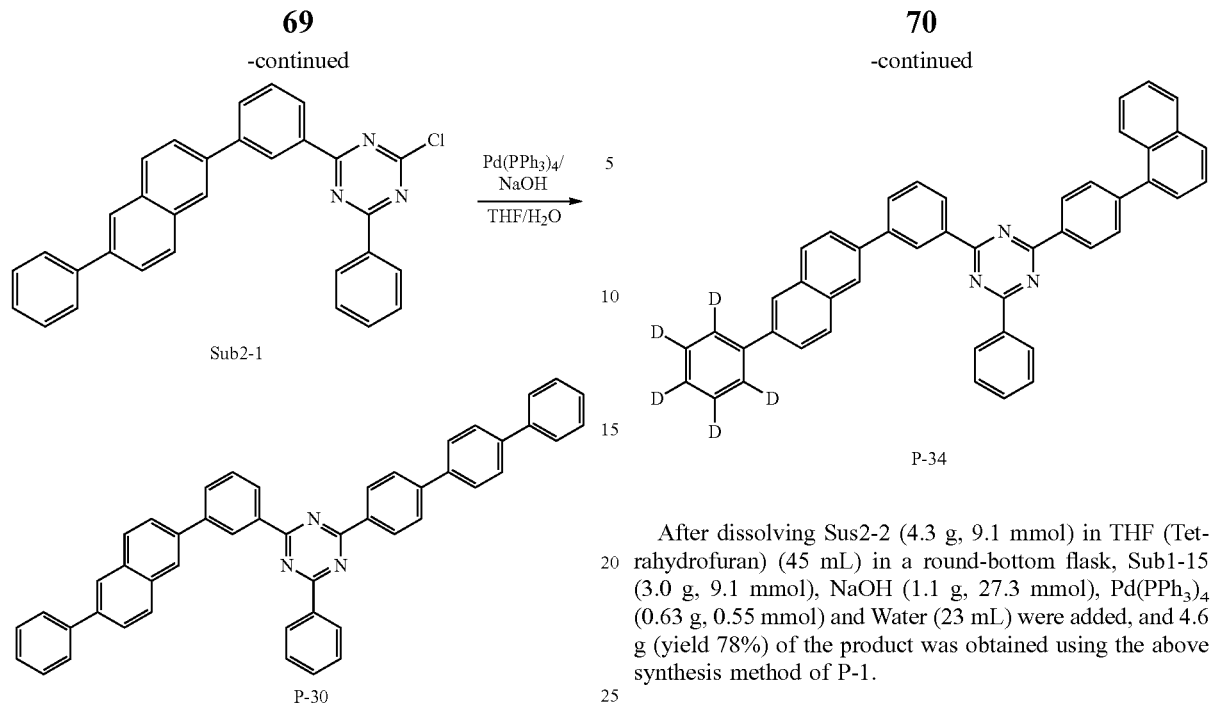

After dissolving Sus2-1 (4.0 g, 8.4 mmol) in THF (Tetrahydrofuran) (42 mL) in a round-bottom flask, Sub1-12 (3.0 g, 8.4 mmol), NaOH (1.0 g, 25.3 mmol), Pd(PPh$_3$)$_4$ (0.58 g, 0.51 mmol) and Water (21 mL) were added, and 4.1 g (yield 74%) of the product was obtained using the above synthesis method of P-1.

9. Synthesis Example of P-34

After dissolving Sus2-2 (4.3 g, 9.1 mmol) in THF (Tetrahydrofuran) (45 mL) in a round-bottom flask, Sub1-15 (3.0 g, 9.1 mmol), NaOH (1.1 g, 27.3 mmol), Pd(PPh$_3$)$_4$ (0.63 g, 0.55 mmol) and Water (23 mL) were added, and 4.6 g (yield 78%) of the product was obtained using the above synthesis method of P-1.

10. Synthesis Example of P-40

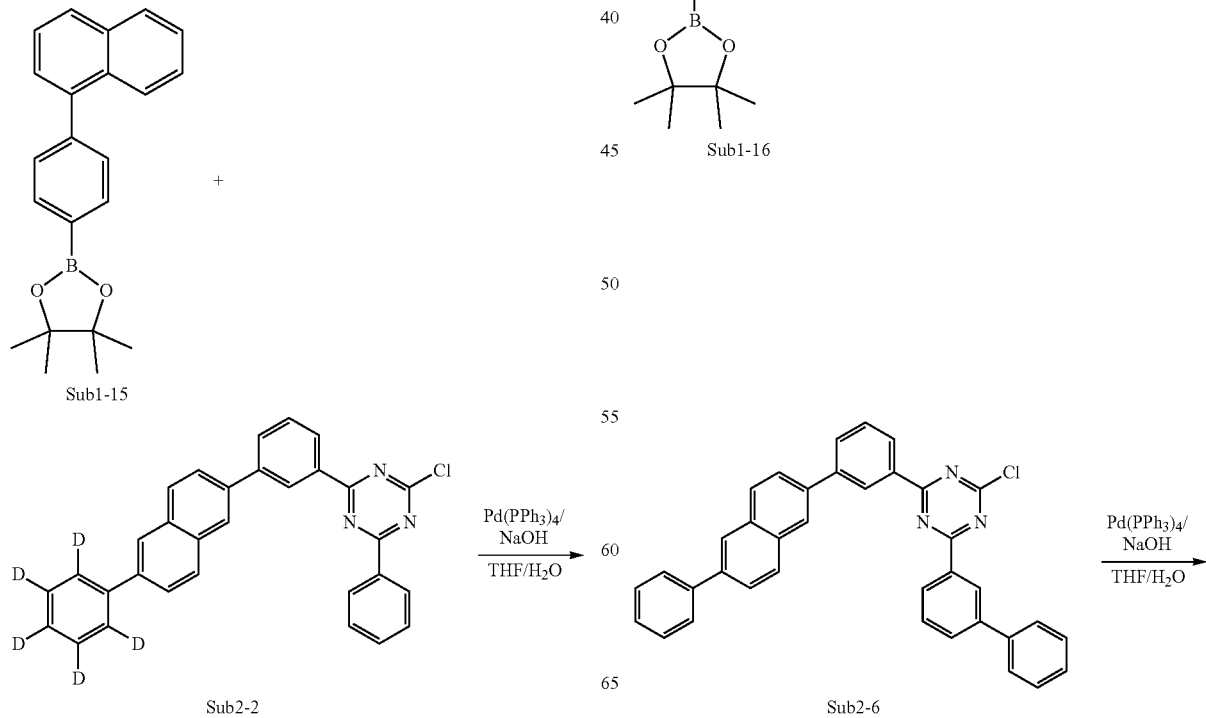

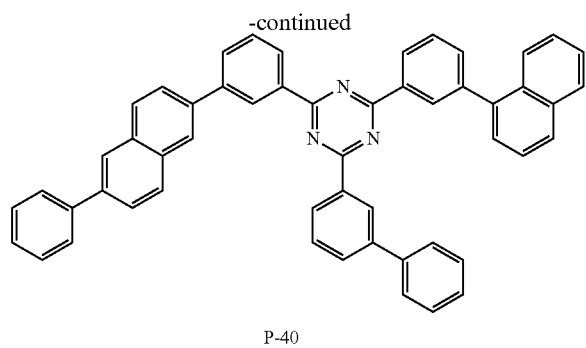

P-40

After dissolving Sus2-6 (5.0 g, 9.1 mmol) in THF (Tetrahydrofuran) (45 mL) in a round-bottom flask, Sub1-16 (3.0 g, 9.1 mmol), NaOH (1.1 g, 27.3 mmol), Pd(PPh$_3$)$_4$ (0.63 g, 0.55 mmol) and Water (23 mL) were added, and 5.0 g (yield 77%) of the product was obtained using the above synthesis method of P-1.

11. Synthesis Example of P-42

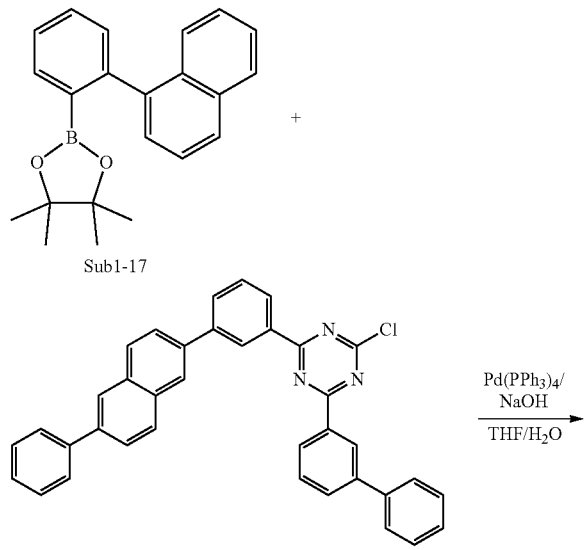

P-42

After dissolving Sus2-6 (5.0 g, 9.1 mmol) in THF (Tetrahydrofuran) (45 mL) in a round-bottom flask, Sub1-17 (3.0 g, 9.1 mmol), NaOH (1.1 g, 27.3 mmol), Pd(PPh$_3$)$_4$ (0.63 g, 0.55 mmol) and Water (23 mL) were added, and 4.5 g (yield 70%) of the product was obtained using the above synthesis method of P-1.

Meanwhile, FD-MS values of compounds P-1 to P-44 of the present invention prepared according to the above synthesis examples are shown in Table 3.

TABLE 3

| compound | FD-MS |
| --- | --- |
| P-1 | m/z = 587.24(C$_{43}$H$_{29}$N$_3$ = 587.73) |
| P-2 | m/z = 637.25(C$_{47}$H$_{31}$N$_3$ = 637.79) |
| P-3 | m/z = 663.27(C$_{49}$H$_{33}$N$_3$ = 663.82) |
| P-4 | m/z = 592.27(C$_{43}$H$_{24}$D$_5$N$_3$ = 592.76) |
| P-5 | m/z = 587.24(C$_{43}$H$_{29}$N$_3$ = 587.73) |
| P-6 | m/z = 587.24(C$_{43}$H$_{29}$N$_3$ = 587.73) |
| P-7 | m/z = 663.27(C$_{49}$H$_{33}$N$_3$ = 663.82) |
| P-8 | m/z = 663.27(C$_{49}$H$_{33}$N$_3$ = 663.82) |
| P-9 | m/z = 587.24(C$_{43}$H$_{29}$N$_3$ = 587.73) |
| P-10 | m/z = 663.27(C$_{49}$H$_{33}$N$_3$ = 663.82) |
| P-11 | m/z = 637.25(C$_{47}$H$_{31}$N$_3$ = 637.79) |
| P-12 | m/z = 590.25(C$_{43}$H$_{26}$D$_3$N$_3$ = 590.74) |
| P-13 | m/z = 637.25(C$_{47}$H$_{31}$N$_3$ = 637.79) |
| P-14 | m/z = 737.28(C$_{55}$H$_{35}$N$_3$ = 737.91) |
| P-15 | m/z = 687.27(C$_{51}$H$_{33}$N$_3$ = 687.85) |
| P-16 | m/z = 763.3(C$_{57}$H$_{37}$N$_3$ = 763.94) |
| P-17 | m/z = 737.28(C$_{55}$H$_{35}$N$_3$ = 737.91) |
| P-18 | m/z = 713.28(C$_{53}$H$_{35}$N$_3$ = 713.88) |
| P-19 | m/z = 637.25(C$_{47}$H$_{31}$N=3 = 637.79) |
| P-20 | m/z = 642.28(C$_{47}$H$_{26}$D$_5$N$_3$ = 642.82) |
| P-21 | m/z = 637.25(C$_{47}$H$_{31}$N$_3$ = 637.79) |
| P-22 | m/z = 642.28(C$_{47}$H$_{26}$D$_5$N$_3$ = 642.82) |
| P-23 | m/z = 813.31(C$_{61}$H$_{39}$N$_3$ = 814) |
| P-24 | m/z = 763.3(C$_{57}$H$_{37}$N$_3$ = 763.94) |
| P-25 | m/z = 637.25(C$_{47}$H$_{31}$N$_3$ = 637.79) |
| P-26 | m/z = 642.28(C$_{47}$H$_{26}$D$_5$N$_3$ = 642.82) |
| P-27 | m/z = 763.3(C$_{57}$H$_{37}$N$_3$ = 763.94) |
| P-28 | m/z = 713.28(C$_{53}$H$_{35}$N$_3$ = 713.88) |
| P-29 | m/z = 663.27(C$_{49}$H$_{33}$N$_3$ = 663.82) |
| P-30 | m/z = 667.29(C$_{49}$H$_{29}$D$_4$N$_3$ = 667.85) |
| P-31 | m/z = 815.33(C$_{61}$H$_{41}$N$_3$ = 816.02) |
| P-32 | m/z = 713.28(C$_{53}$H$_{35}$N$_3$ = 713.88) |
| P-33 | m/z = 637.25(C$_{47}$H$_{31}$N$_3$ = 637.79) |
| P-34 | m/z = 642.28(C$_{47}$H$_{26}$D$_5$N$_3$ = 642.82) |
| P-35 | m/z = 713.28(C$_{53}$H$_{35}$N$_3$ = 713.88) |
| P-36 | m/z = 642.28(C$_{47}$H$_{26}$D$_5$N$_3$ = 642.82) |
| P-37 | m/z = 637.25(C$_{47}$H$_{31}$N$_3$ = 637.79) |
| P-38 | m/z = 763.3(C$_{57}$H$_{37}$N$_3$ = 763.94) |
| P-39 | m/z = 763.3(C$_{57}$H$_{37}$N$_3$ = 763.94) |
| P-40 | m/z = 713.28(C$_{53}$H$_{35}$N$_3$ = 713.88) |
| P-41 | m/z = 637.25(C$_{47}$H$_{31}$N$_3$ = 637.79) |
| P-42 | m/z = 713.28(C$_{53}$H$_{35}$N$_3$ = 713.88) |
| P-43 | m/z = 641.28(C$_{47}$H$_{27}$D$_4$N$_3$ = 641.81) |
| P-44 | m/z = 863.33(C$_{65}$H$_{41}$N$_3$ = 864.06) |

Evaluation of Manufacture of Organic Electronic Element

[Example 1] Red Organic Light Emitting Diode (Phosphorescent Host)

An organic electroluminescent device was manufactured according to a conventional method by using the compound obtained through synthesis as a emitting host material of the emitting layer. First, on an ITO layer (anode) formed on a glass substrate, N1-(naphthalen-2-yl)-N4,N4-bis(4-(naphthalen-2-yl(phenyl)amino)phenyl)-N1-phenylbenzene-1,4-diamine (Hereinafter, abbreviated as 2-TNATA) film as a hole injection layer was vacuum-deposited to form a thickness of 60 nm. 4,4-bis[N-(1-naphthyl)-N-phenylamino]biphenyl (hereinafter—NPD) as a hole transport compound on the hole injection layer was vacuum-deposited to a thickness of 50 nm to form a hole transport layer.

An emitting auxiliary layer was formed by vacuum-depositing Tris(4-(9H-carbazol-9-yl)phenyl)amine (hereinafter, TCTA) to a thickness of 10 nm as an emitting auxiliary layer material on the hole transport layer. After forming the emitting auxiliary layer, as a host on the emitting auxiliary layer, the compound P-1 of the present invention represented by Formula 1-1 and the compound C-1 were used in a weight ratio (5:5), and an emitting layer was deposited to a thickness of 30 nm by doping (piq)₂Ir(acac) as a dopant material in a 95:5 weight ratio. Then (1,1'-bisphenyl)-4-oleato)bis(2-methyl-8-quinolineoleato)aluminum (hereinafter abbreviated as BAlq) as a hole blocking layer was vacuum-deposited to a thickness of 10 nm, as an electron transport layer, bis(10-hydroxybenzo[h]quinolinato)beryllium (hereinafter, abbreviated as Alq3) was deposited to a thickness of 25 nm. Thereafter, LiF, which is an alkali metal halide, was deposited as an electron injection layer to a thickness of 0.2 nm, and then Al was deposited to a thickness of 150 nm and used as a cathode to prepare an organic electroluminescent device.

[Example 2] to [Example 22]

An organic electroluminescent device was manufactured in the same manner as in Example 1, except that the compounds of the present invention described in Table 4 were used instead of the compounds P-1 and C-1 of the present invention as host materials for the emitting layer.

[Comparative Example 1] to [Comparative Example 3]

An organic electroluminescent device was manufactured in the same manner as in Example 1, except that the compound shown in Table 4 was used instead of the compound P-1 of the present invention as the host material of the emitting layer.

[Comparative compound A]

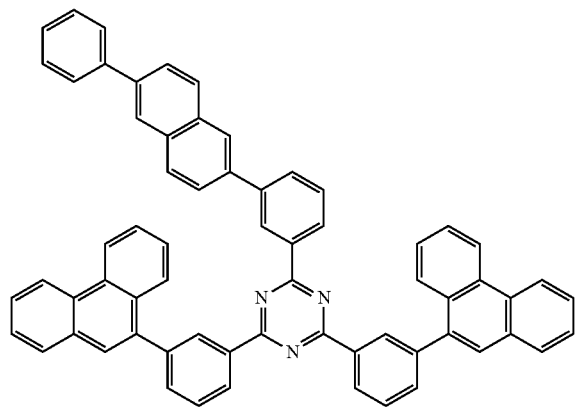

[Comparative compound B]

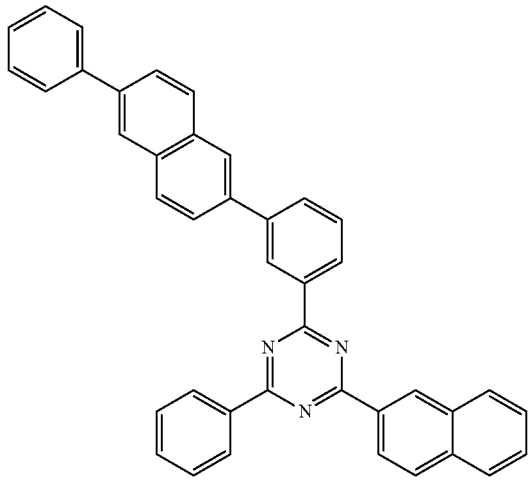

[comparative compound C]

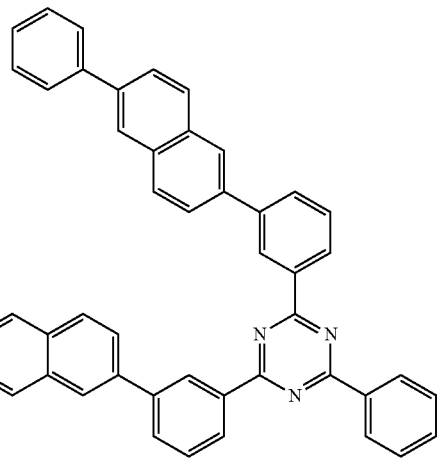

<compound C-1>

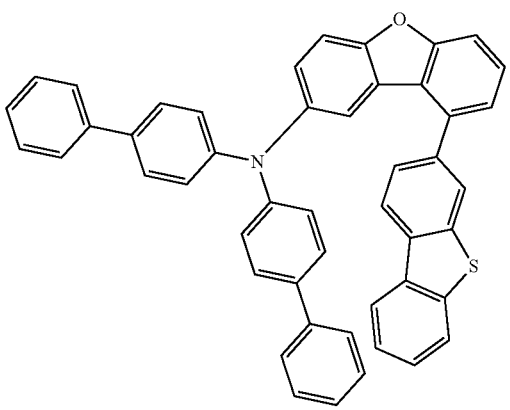

<compound C-2>

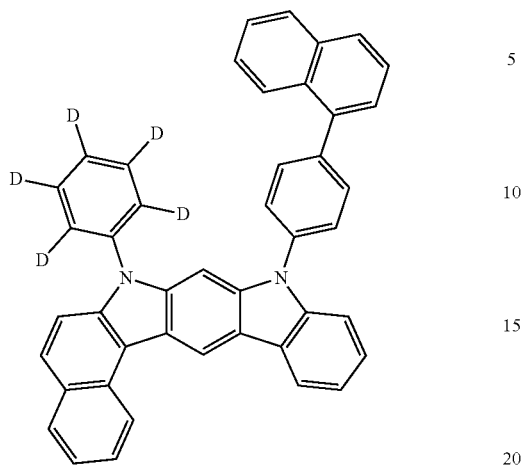

By applying a forward bias DC voltage to the organic electronic elements prepared in Examples 1 to 22 and Comparative Examples 1 to 3 prepared in this way, Electroluminescence (EL) characteristics were measured with PR-650 from Photoresearch, and as a result of the measurement, the T95 lifetime was measured using a lifetime measuring device manufactured by McScience at 2500 cd/m² standard luminance. Table 4 shows the device fabrication and evaluation results.

TABLE 4

| | First compound | Second compound | Voltage | Current Density (mA/cm²) | Brightness (cd/m²) | Efficiency (cd/A) | T(95) |
|---|---|---|---|---|---|---|---|
| comparative example 1 | comparative compound A | compound (C-1) | 5.7 | 14.5 | 2500 | 17.3 | 96.5 |
| comparative example 2 | comparative compound B | compound (C-1) | 5.6 | 14.0 | 2500 | 17.9 | 102.6 |
| comparative example 3 | comparative compound C | compound (C-1) | 5.8 | 14.8 | 2500 | 16.9 | 97.7 |
| example 1 | Compound (P-1) | compound (C-1) | 5.0 | 8.1 | 2500 | 30.9 | 130.6 |
| example 2 | Compound (P-1) | compound (C-2) | 4.9 | 7.9 | 2500 | 31.7 | 126.2 |
| example 3 | Compound (P-4) | compound (C-1) | 4.9 | 8.1 | 2500 | 30.8 | 130.6 |
| example 4 | Compound (P-4) | compound (C-2) | 4.9 | 7.9 | 2500 | 31.7 | 126.2 |
| example 5 | Compound (P-5) | compound (C-1) | 5.0 | 10.0 | 2500 | 24.9 | 129.3 |
| example 6 | Compound (P-5) | compound (C-2) | 5.0 | 9.8 | 2500 | 25.6 | 125.0 |
| example 7 | Compound (P-9) | compound (C-1) | 5.1 | 10.5 | 2500 | 23.8 | 126.8 |
| example 8 | Compound (P-9) | compound (C-2) | 5.0 | 10.2 | 2500 | 24.4 | 122.6 |
| example 9 | Compound (P-13) | compound (C-1) | 4.9 | 9.8 | 2500 | 25.4 | 135.7 |
| example 10 | Compound (P-13) | compound (C-2) | 4.9 | 9.6 | 2500 | 26.1 | 131.1 |
| example 11 | Compound (P-18) | compound (C-1) | 5.0 | 10.1 | 2500 | 24.7 | 131.8 |
| example 12 | Compound (P-18) | compound (C-2) | 4.9 | 9.8 | 2500 | 25.4 | 127.4 |
| example 13 | Compound (P-22) | compound (C-1) | 4.9 | 9.7 | 2500 | 25.9 | 133.1 |
| example 14 | Compound (P-22) | compound (C-2) | 4.9 | 9.4 | 2500 | 26.6 | 128.6 |

TABLE 4-continued

| | First compound | Second compound | Voltage | Current Density (mA/cm$^2$) | Brightness (cd/m$^2$) | Efficiency (cd/A) | T(95) |
|---|---|---|---|---|---|---|---|
| example 15 | Compound (P-25) | compound (C-1) | 4.9 | 8.0 | 2500 | 31.3 | 140.6 |
| example 16 | Compound (P-25) | compound (C-2) | 4.9 | 7.8 | 2500 | 32.2 | 136.0 |
| example 17 | Compound (P-32) | compound (C-1) | 4.9 | 9.3 | 2500 | 26.8 | 128.0 |
| example 18 | Compound (P-32) | compound (C-2) | 4.9 | 9.1 | 2500 | 27.6 | 123.7 |
| example 19 | Compound (P-34) | compound (C-1) | 4.9 | 8.5 | 2500 | 29.5 | 138.2 |
| example 20 | Compound (P-34) | compound (C-2) | 4.9 | 8.3 | 2500 | 30.3 | 133.5 |
| example 21 | Compound (P-40) | compound (C-1) | 4.9 | 9.1 | 2500 | 27.5 | 135.6 |
| example 22 | Compound (P-40) | compound (C-2) | 4.9 | 8.8 | 2500 | 28.3 | 131.2 |

As can be seen from the results in Table 4, when the compound of the present invention is used as a host material for the emitting layer, it can be seen that the device performance is greatly improved compared to Comparative Examples 1 to 3. When the compound of the present invention represented by Formula 1-1 is compared with Comparative Compounds A to C, the types of substituents bonded to triazines are different, and mobility varies depending on the types of substituents. In other words, the driving, efficiency, and lifespan are determined according to the degree of ease of injection of holes and electrons into the dopant, therefore when the hole and electron ratio (charge balance) is properly maintained, it is judged that the efficiency and lifespan are dramatically increased, which is expected to affect the charge balance according to the respective mobility levels of the first compound and the second compound.

As for the overall characteristics, in the case of the compounds of the present invention represented by Formula 1-1, the electron stability is high, and thus the electrical stability is high in comparison with the comparative compound, and thus a long lifespan characteristic. Comparing the compounds of the present invention, it can be seen that the device performance is determined according to the constituents of the compounds. In terms of driving voltage, it is highly dependent on the overall EOD and HOD, and it can be seen that this mobility is determined by the type of substituents the compound has, and that the efficiency aspect is determined by the electron hole balance of the heterogeneous compound. As a result, the performance of the device is greatly affected depending on the type and bonding position of the substituents substituted within the same backbone.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula 1-1:

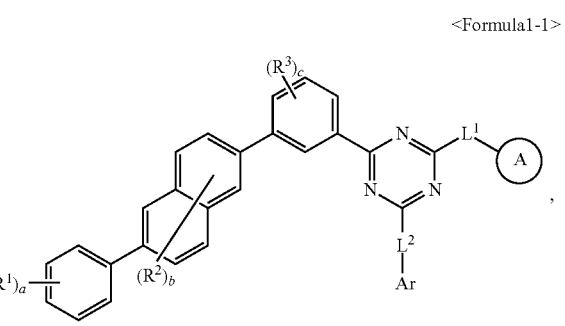

<Formula1-1> wherein:

1) $L^1$ is a substituent represented by any one of Formulas L-1 to L-4:

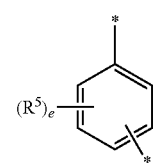

<Formula L-1>

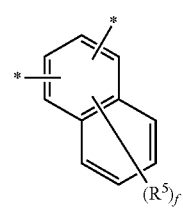

<Formula L-2>

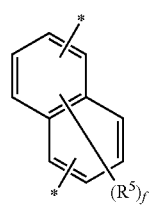

<Formula L-3>

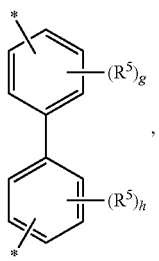
<Formula L-4>

2) L² is a single bond or a C₆~C₆₀ arylene group,
3) Ar is a C₆~C₆₀ aryl group,
4) Ring A is a substituent represented by Formula a, or Formula b:

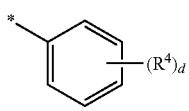
<Formula a>

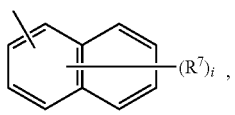
<Formula b>

5) $R^1$, $R^2$, $R^3$, $R^4$, $R^5$ and $R^6$ are the same or different from each other and are each independently hydrogen or deuterium,
6) $R^7$ is selected from the group consisting of hydrogen; deuterium; a $C_6$~$C_{60}$ aryl group; and a $C_6$~$C_{60}$ aryl group substituted with deuterium,
7) A and d are each an integer of 0 to 5; b and f are each an integer of 0 to 6; c, e, g and h are each an integer of 0 to 4; and i is an integer of 0 to 7,
8) * refers to the position to be bonded,
9) Wherein the aryl group and the arylene group may be further substituted with one or more substituents selected from the group consisting of deuterium; a $C_6$~$C_{20}$ aryl group; and a $C_6$~$C_{20}$ aryl group substituted with deuterium.

2. The compound of claim 1, wherein Formula 1-1 is represented by any one of Formulas 1-1-1 to 1-1-5:

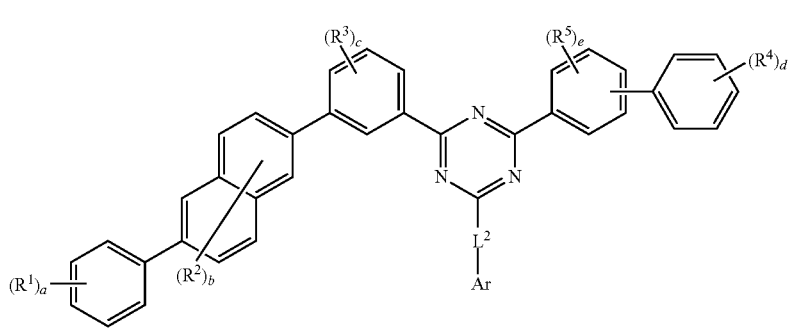
<Formula 1-1-1>

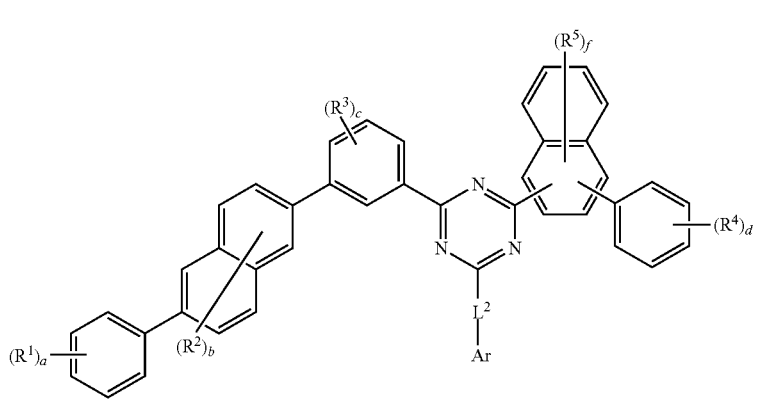
<Formula 1-1-2>

<Formula 1-1-3>
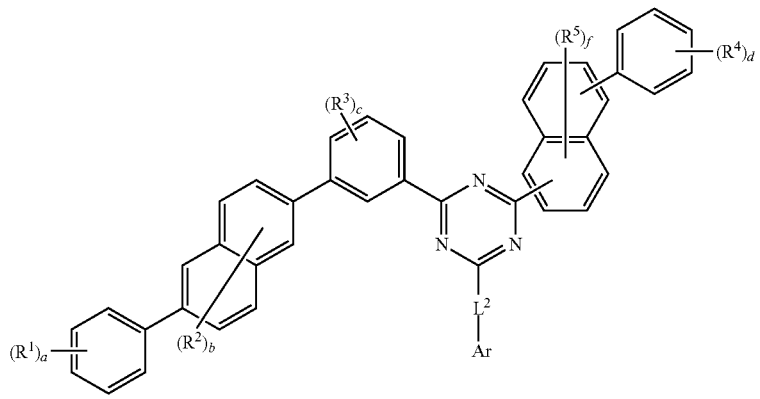
<Formula 1-1-4>
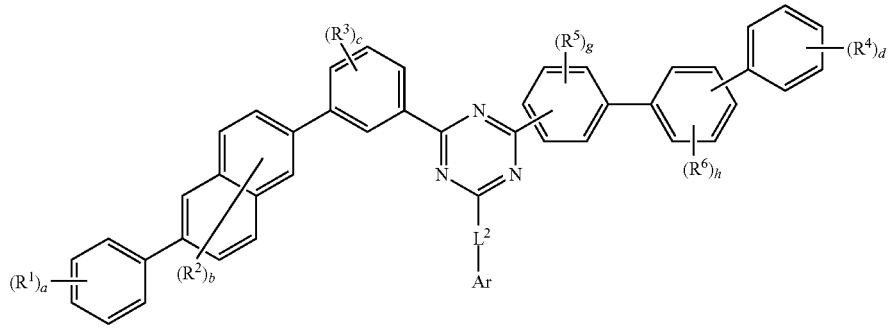
<Formula 1-1-5>
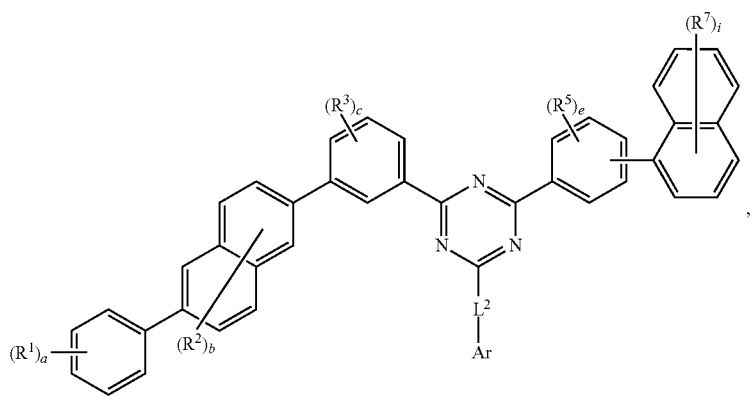
wherein $R^1$, $R^2$, $R^3$, $R^4$, $R^5$, $R^6$, $R^7$, $L^2$, Ar, a, b, c, d, e, f, g, h and i are the same as defined in claim 1.
3. The compound of claim 1, wherein Formula 1-1 is represented by any one of Formulas 1-1-1-a to 1-1-1-c:
<Formula 1-1-1-a>
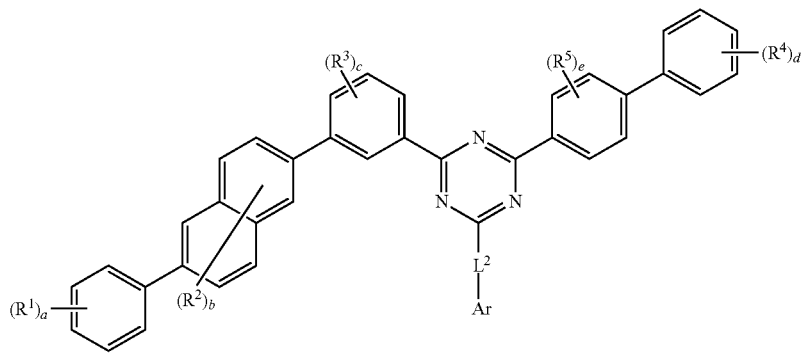

<Formula 1-1-1-b>
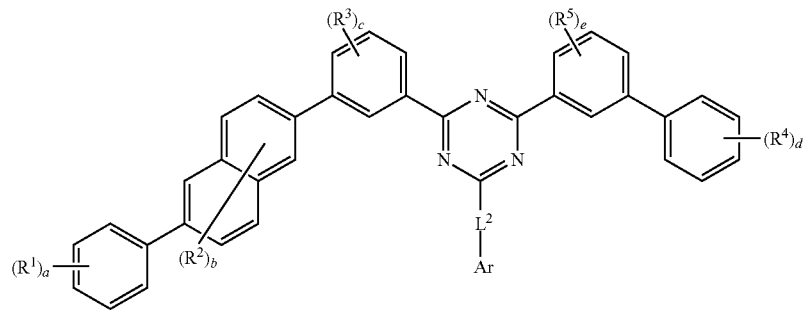
<Formula 1-1-1-c>
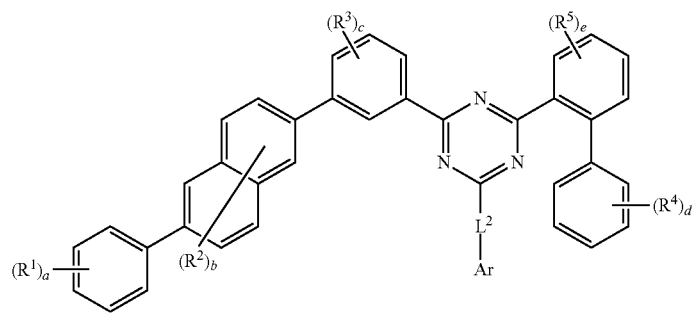
wherein $R^1$, $R^2$, $R^3$, $R^4$, $R^5$, $L^2$, Ar, a, b, c, d and e are the same as defined in claim 1.
4. The compound of claim 1, wherein Formula 1-1 is represented by any one of Formulas 1-1-2-a to 1-1-2-c:
<Formula 1-1-2-a>
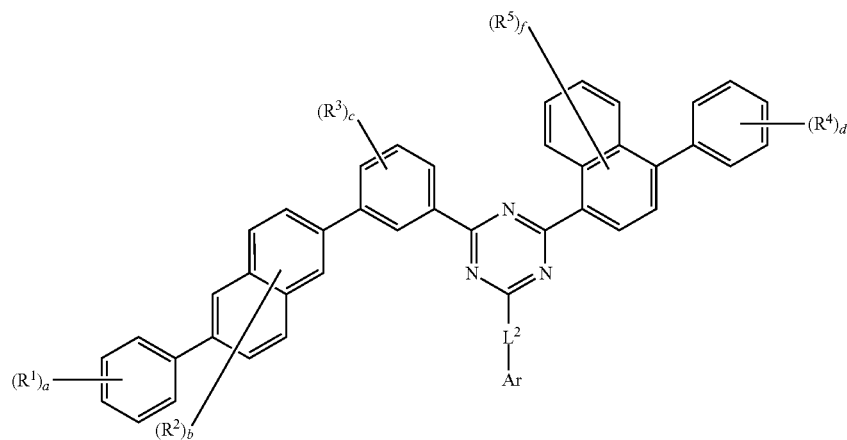

-continued
<Formula 1-1-2-b>
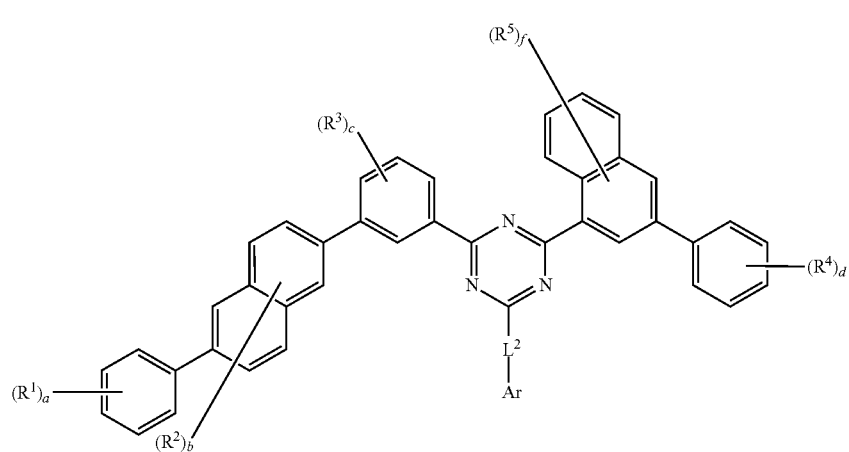
<Formula 1-1-2-c>
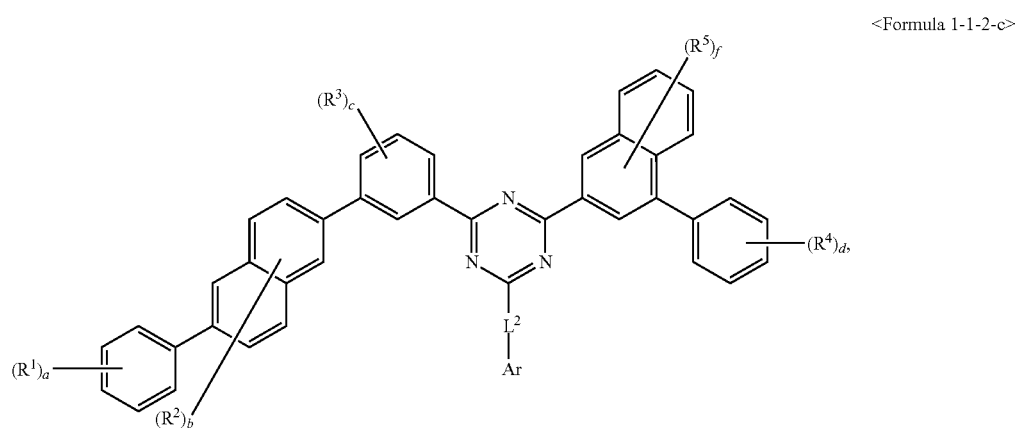
wherein $R^1$, $R^2$, $R^3$, $R^4$, $R^5$, $L^2$, Ar, a, b, c, d and f are same as defined in claim 1.
5. The compound of claim 1, wherein Formula 1-1 is represented by Formula 1-1-3-a or Formula 1-1-3-b:
<Forula 1-1-3-a
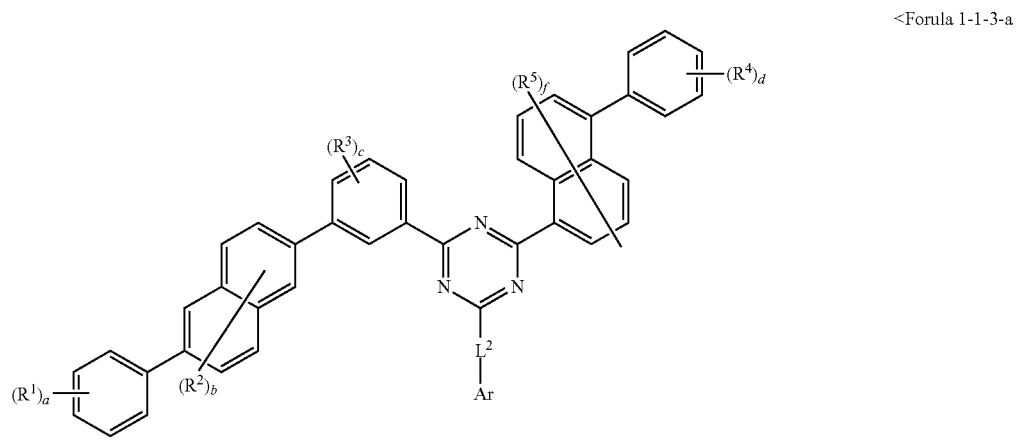

-continued
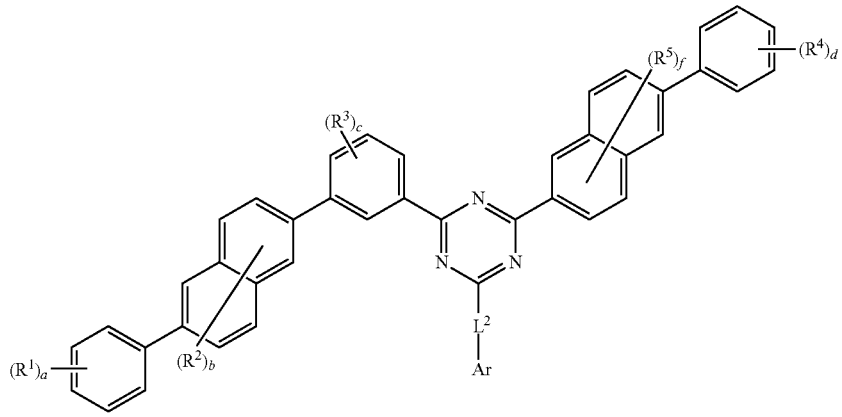
<Formula 1-1-3-b>
wherein $R^1$, $R^2$, $R^3$, $R^4$, $R^5$, $L^2$, Ar, a, b, c, d and f are the same as defined in claim 1.
6. The compound of claim 1, wherein Formula 1-1 is represented by Formula 1-1-4-a:
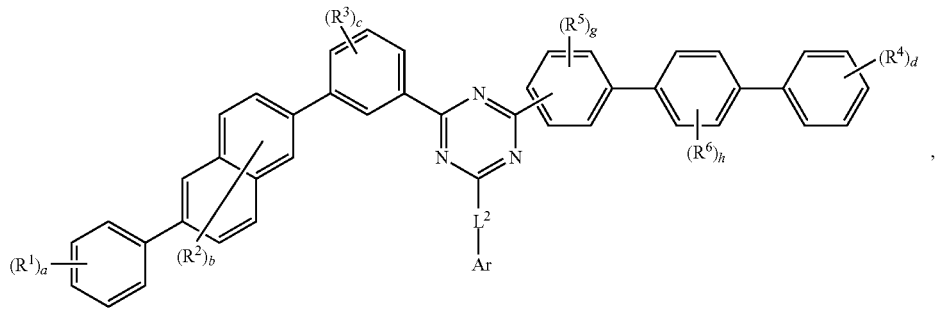
<Formula 1-1-4-a>
wherein $R^1$, $R^2$, $R^3$, $R^4$, $R^5$, $R^6$, $L^2$, Ar, a, b, c, d, g, and h are the same as defined in claim 1.
7. The compound of claim 1, wherein Formula 1-1 is represented by Formula 1-1-4-b or Formula 1-1-4-c:
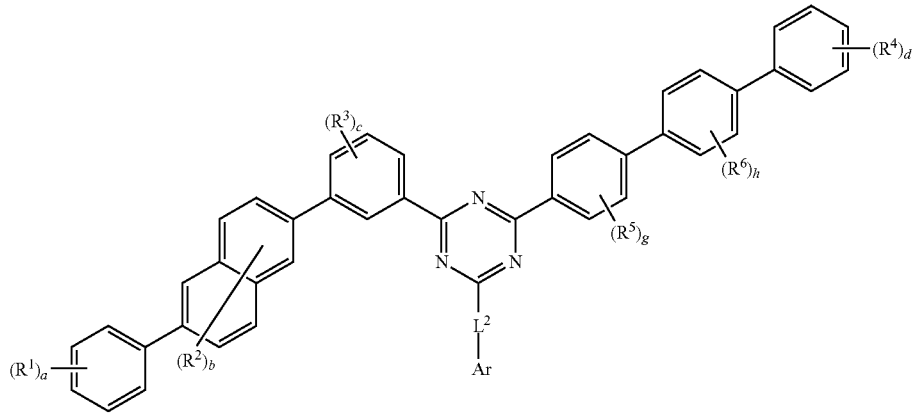
<Formula 1-1-4-b>

-continued
<Formula 1-1-4-c>
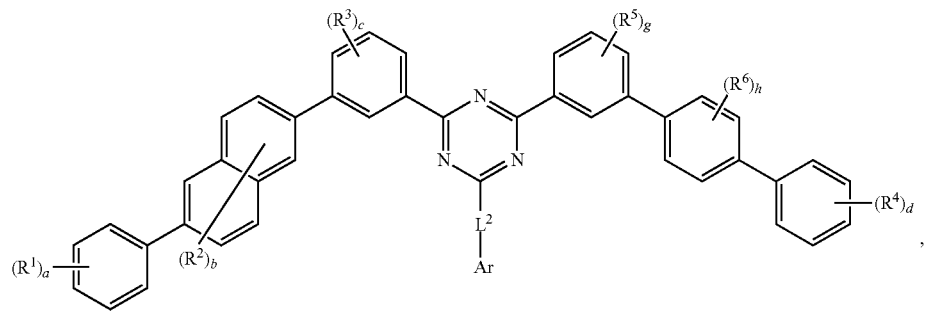
wherein R¹, R², R³, R⁴, R⁵, R⁶, L², Ar, a, b, c, d, g and h are as the same as defined in claim 1.
8. The compound of claim 1, wherein Formula 1-1 is represented by any one of Formulas 1-1-5-a to 1-1-5-c:
<Formula 1-1-5-a>
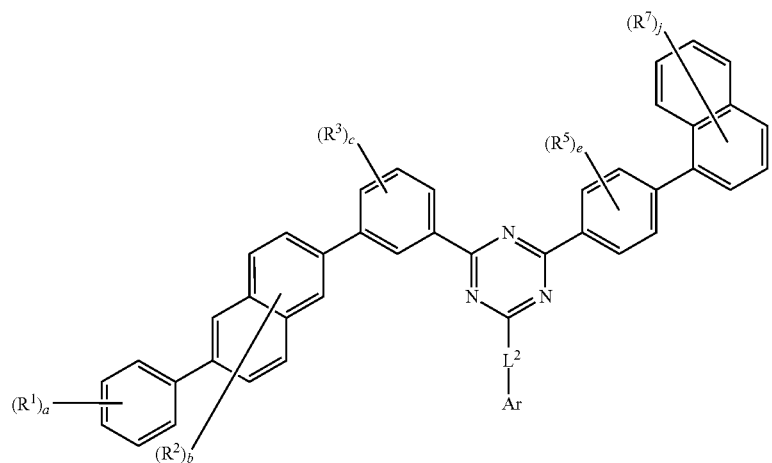
<Formula 1-1-5-b>
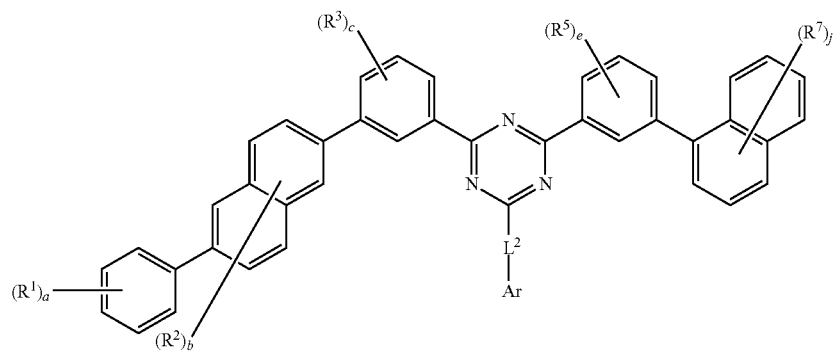
<Formula 1-1-5-c>
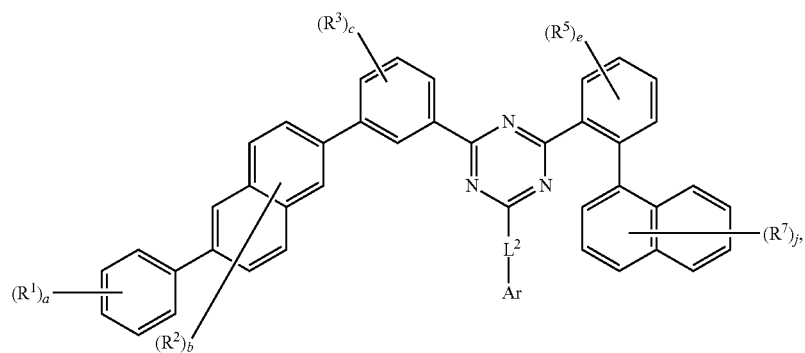

wherein $R^1$, $R^2$, $R^3$, $R^5$, $R^7$, $L^2$, Ar, a, b, c, e and i are the same as defined in claim 1.
9. The compound of claim 1, wherein the compound represented by Formula 1-1 is represented by any one of the following compounds P-1 to P-44:
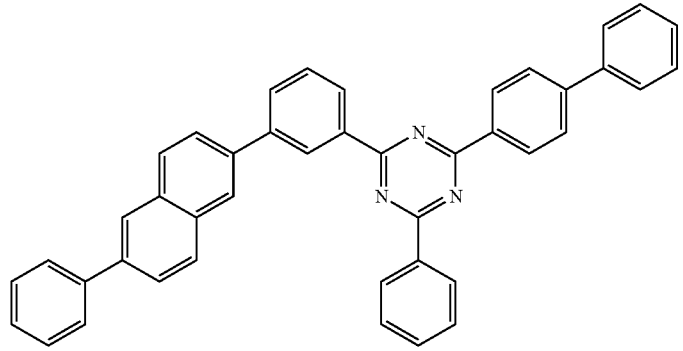
P-1
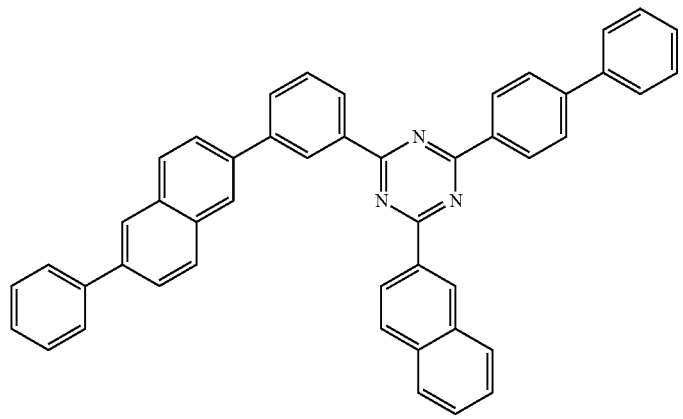
P-2
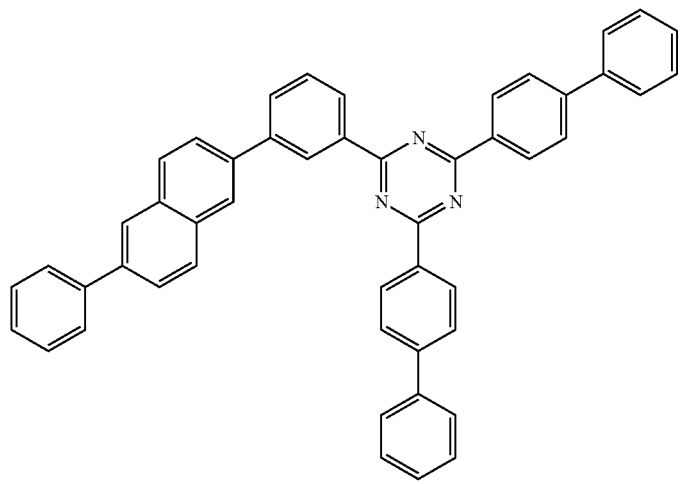
P-3

P-4
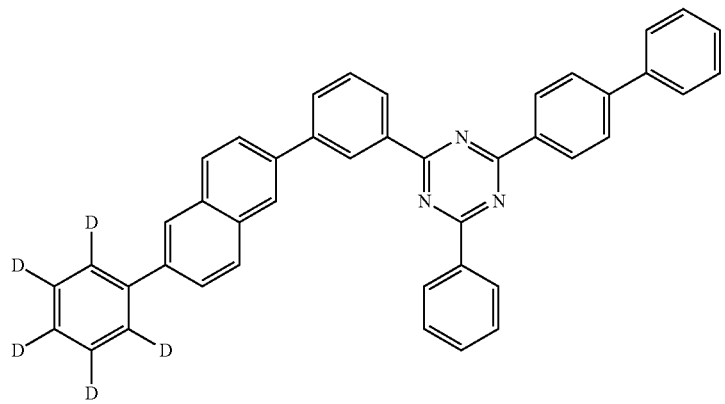
P-5
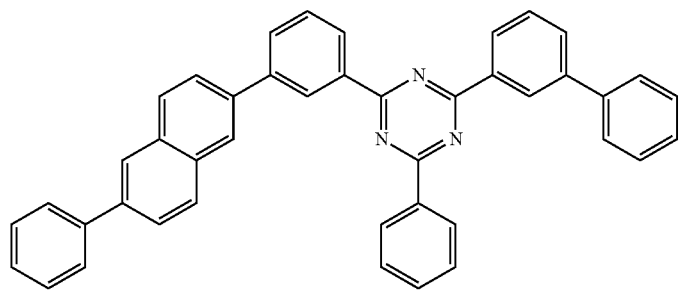
P-6
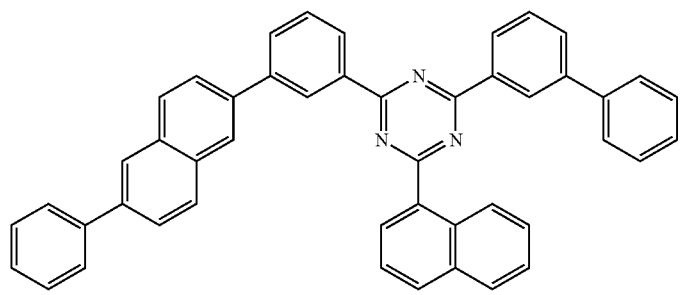
P-7
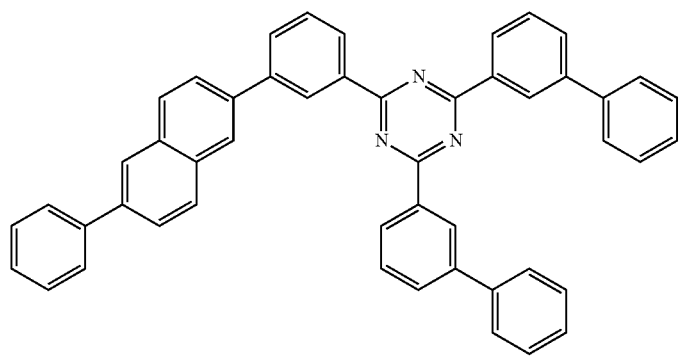
P-8
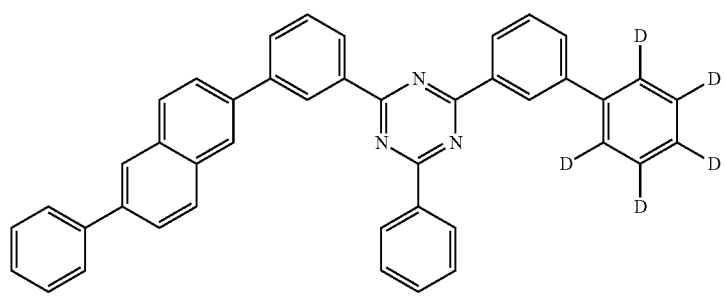

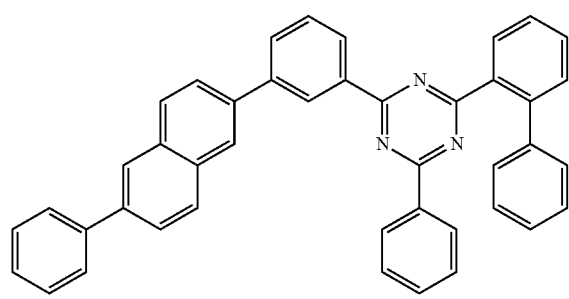
P-9
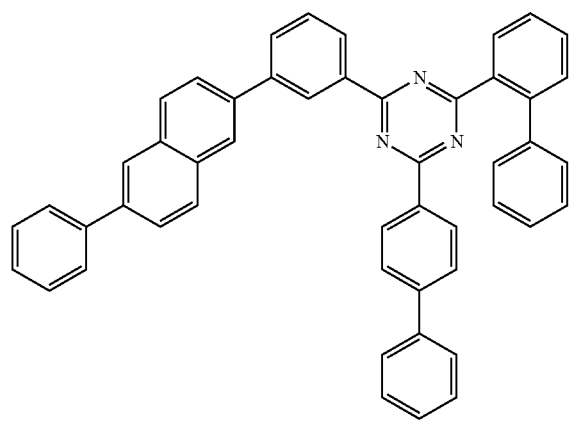
P-10
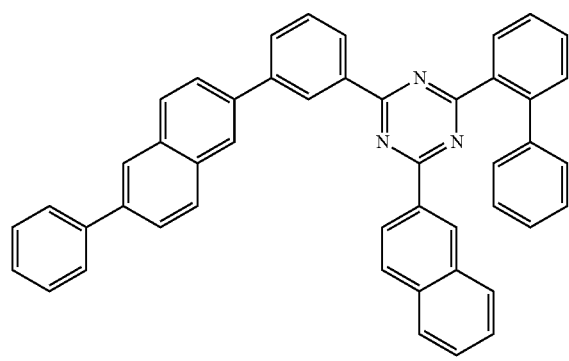
P-11
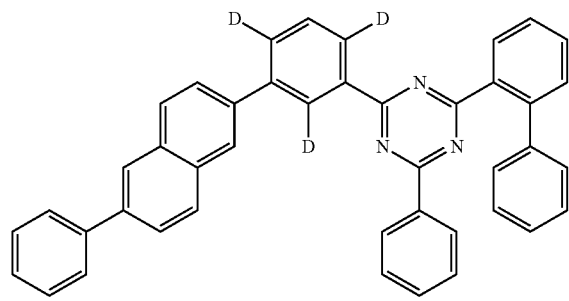
P-12

-continued
P-13
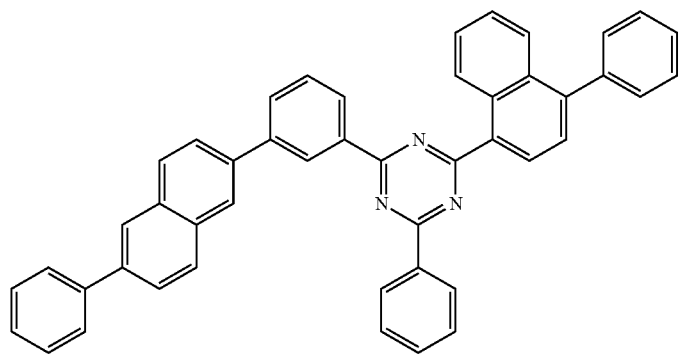
P-14
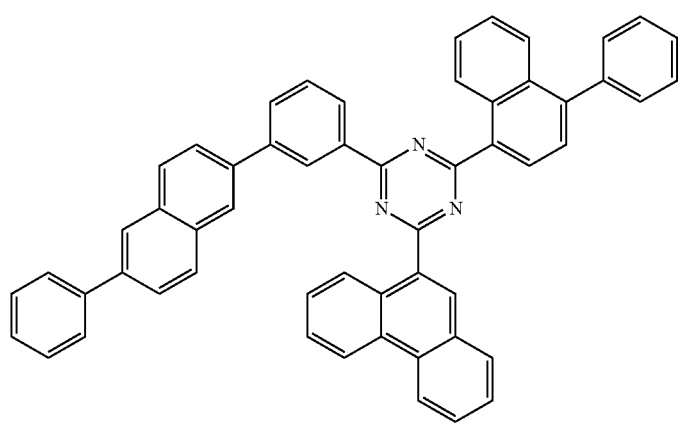
P-15
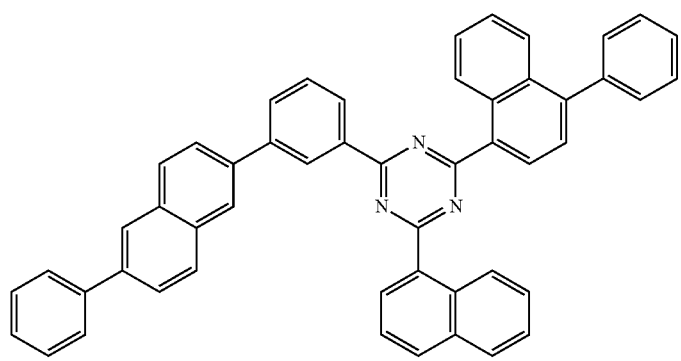

-continued
P-16
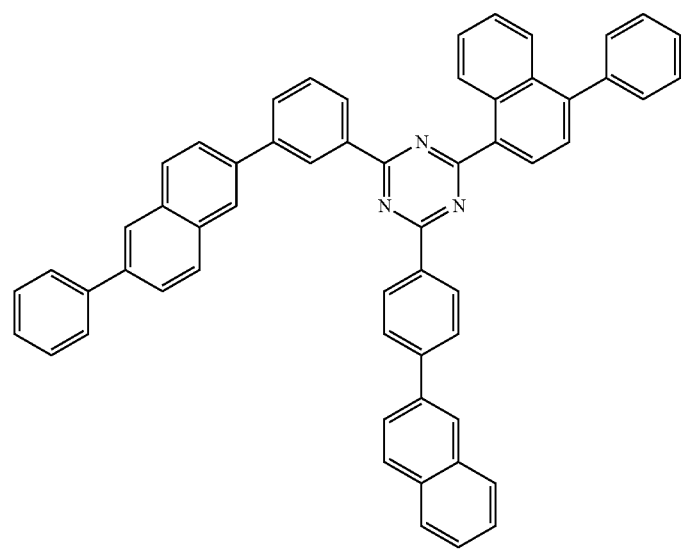
P-17
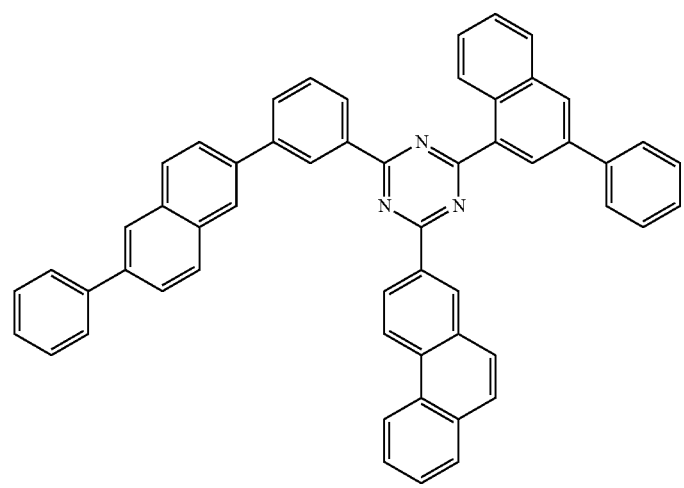
P-18
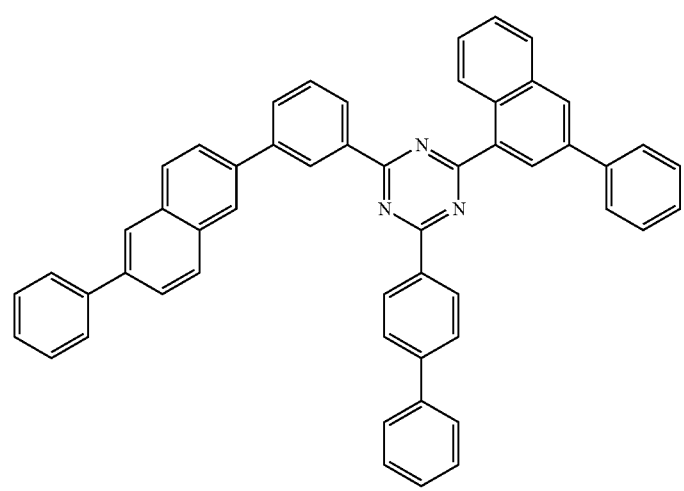

P-19
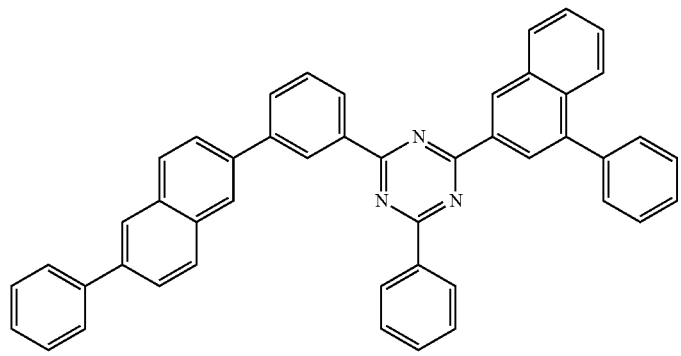
P-20
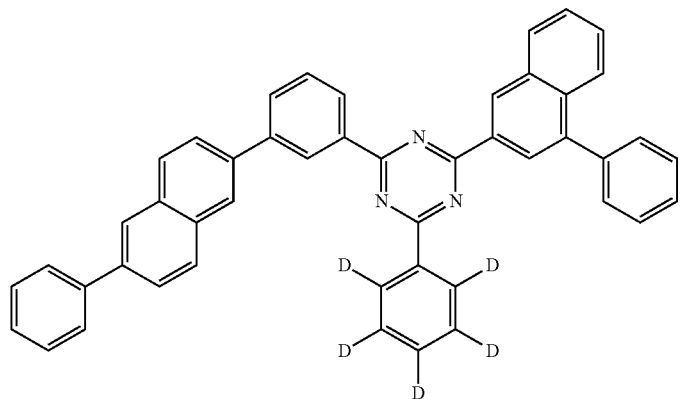
P-21
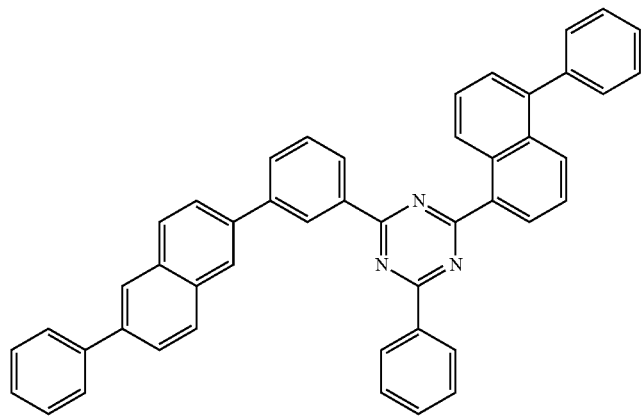
P-22
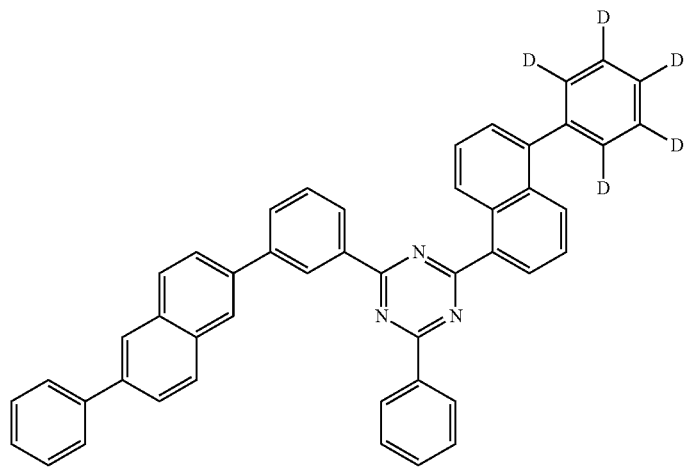

P-23
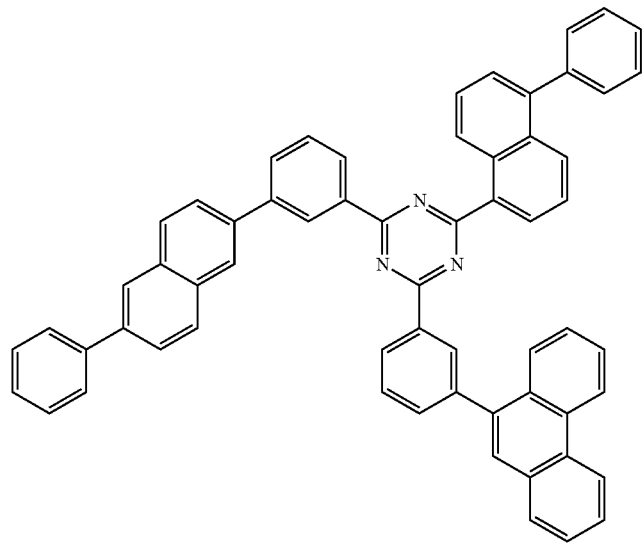
P-24
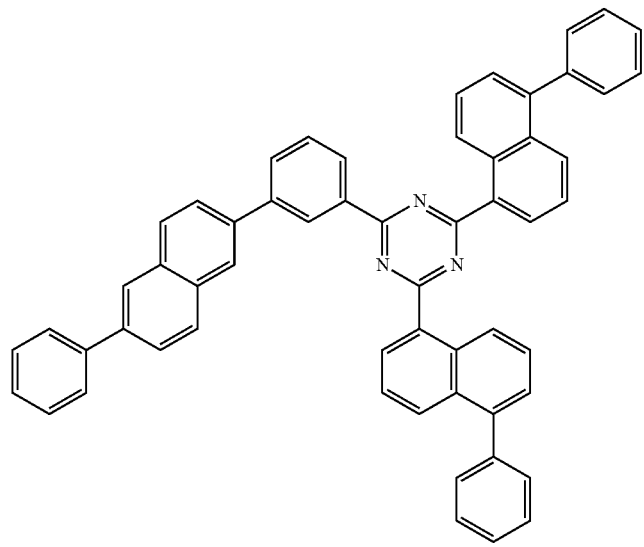
P-25
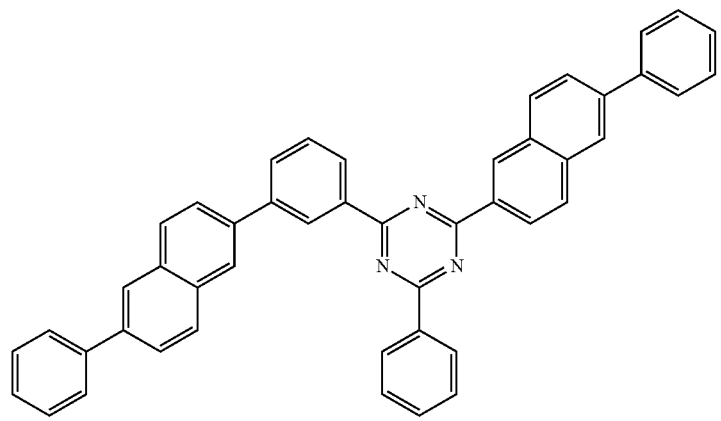

P-26
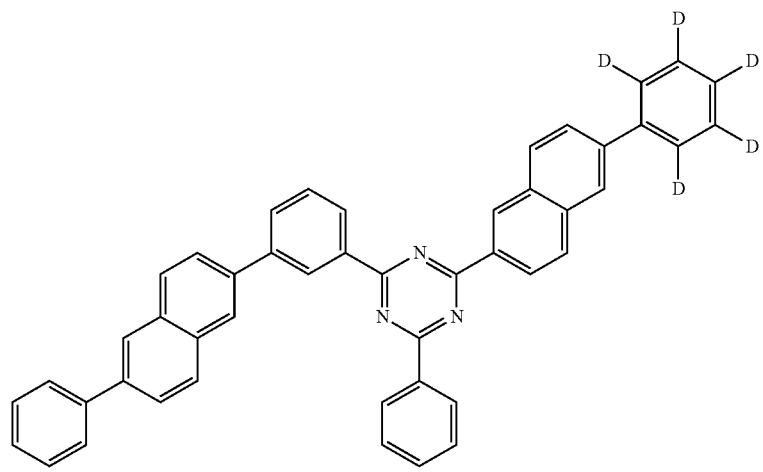
P-27
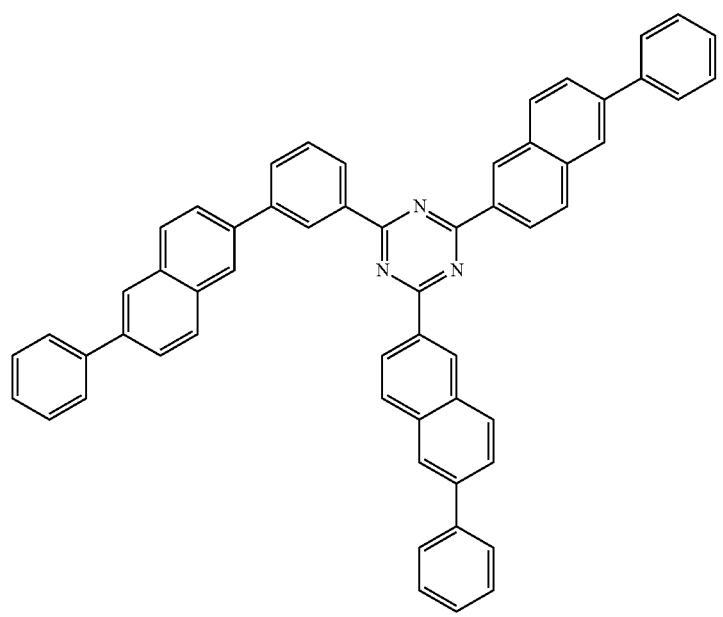
P-28
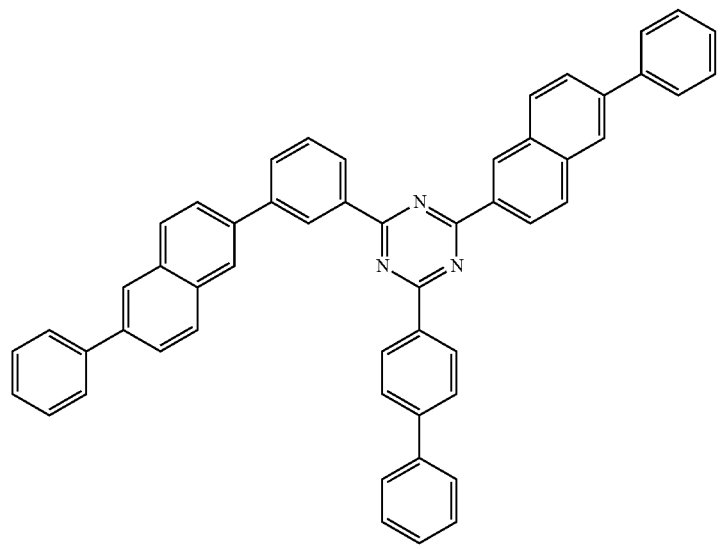

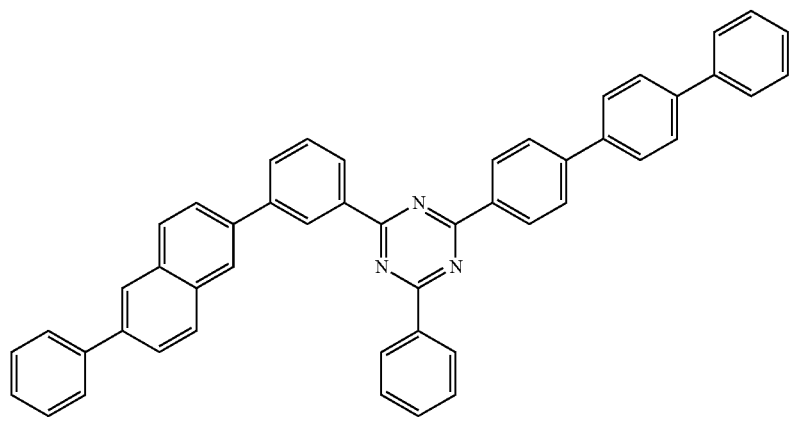
P-29
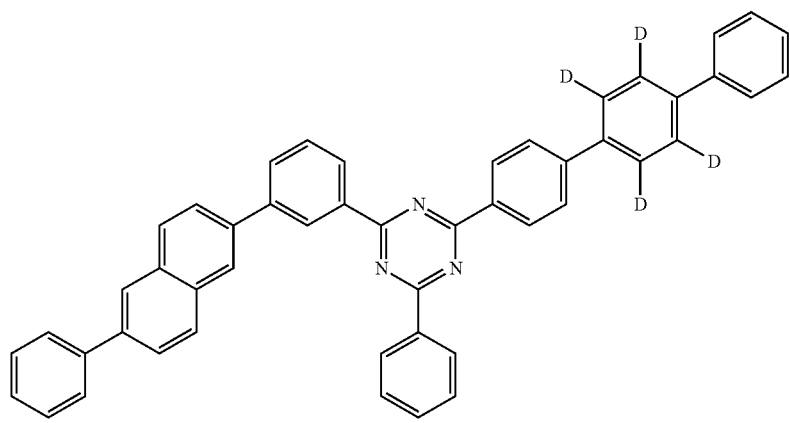
P-30
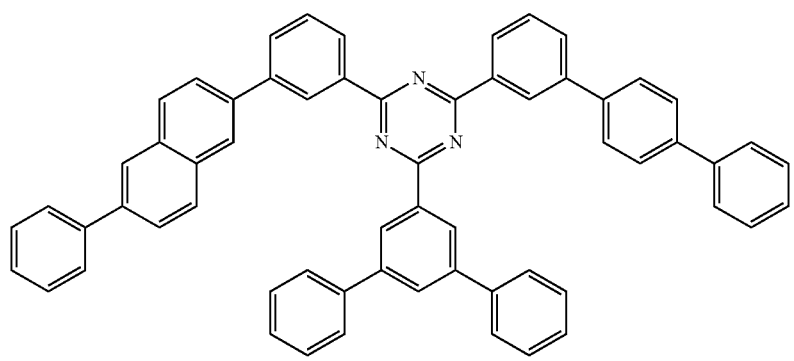
P-31

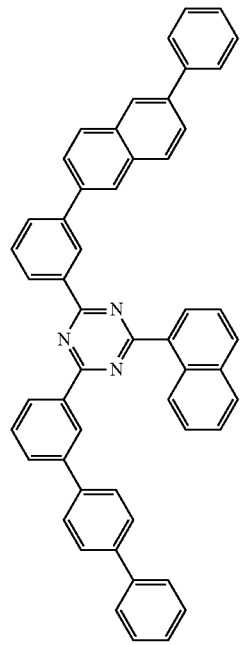
P-32
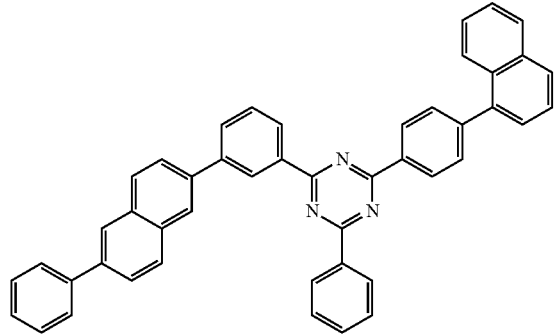
P-33
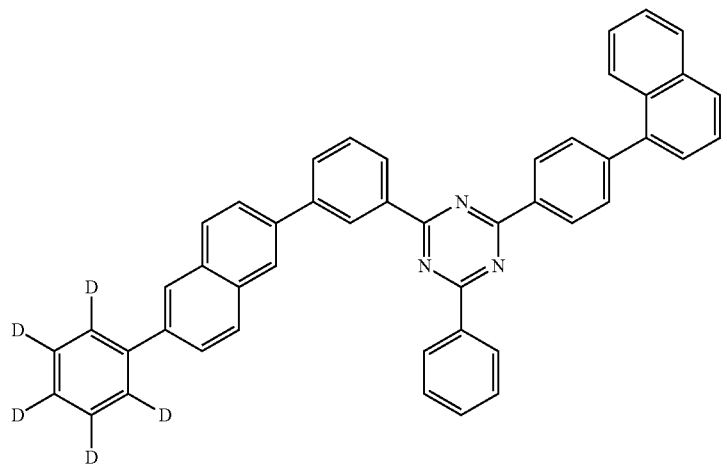
P-34

P-35
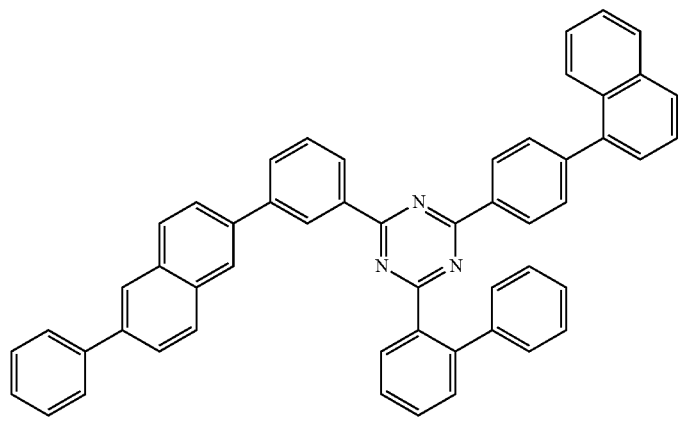
P-36
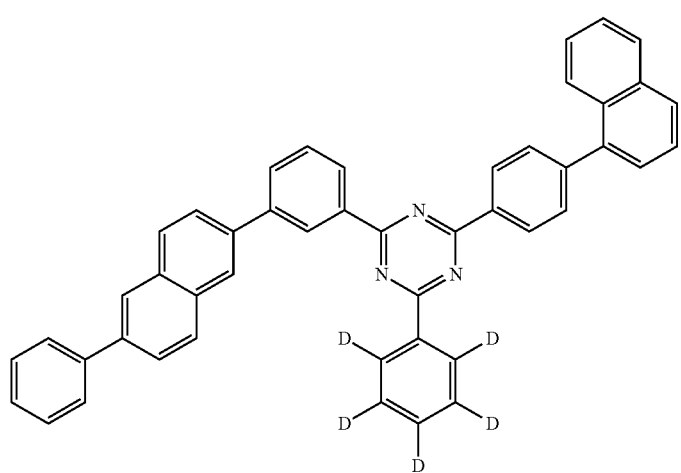
P-37
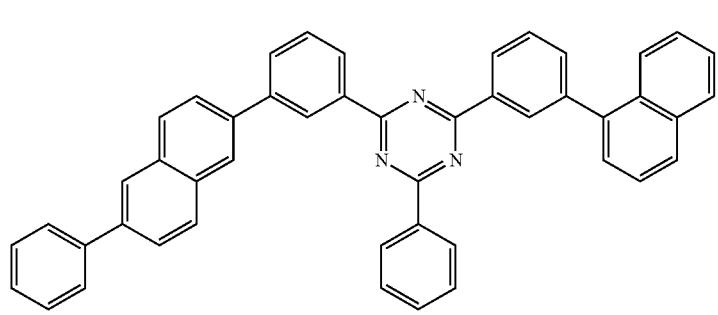
P-38
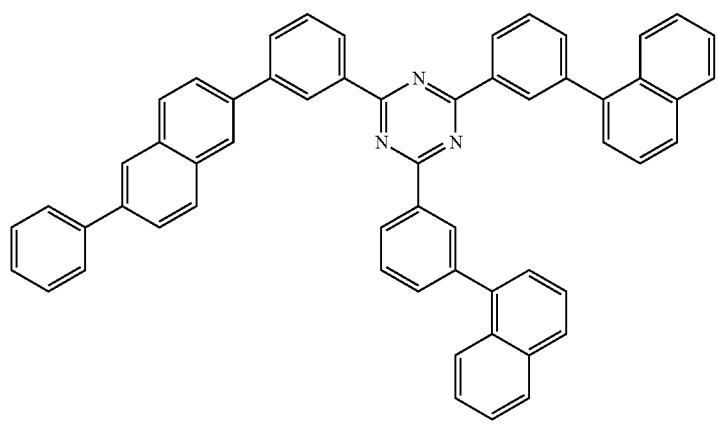

P-39
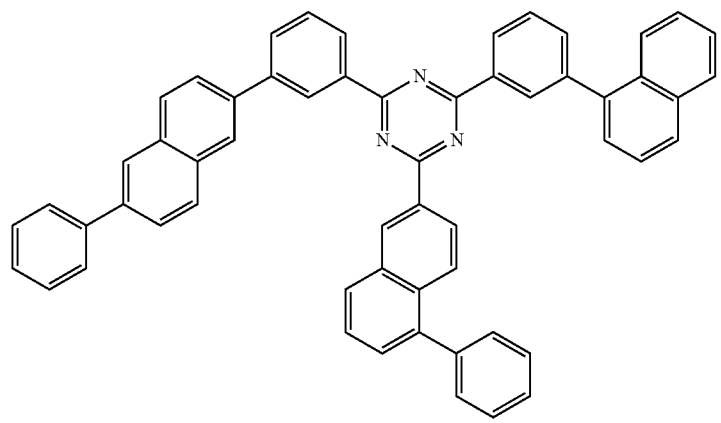
P-40
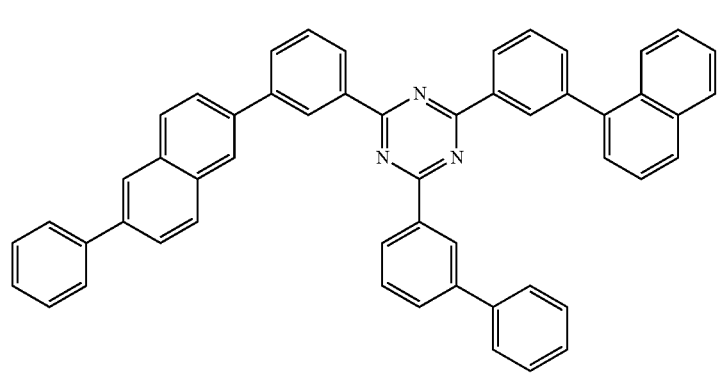
P-41
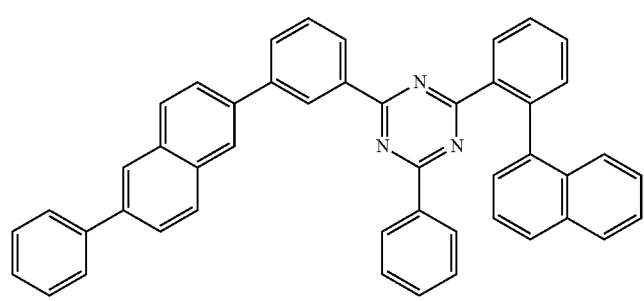
P-42
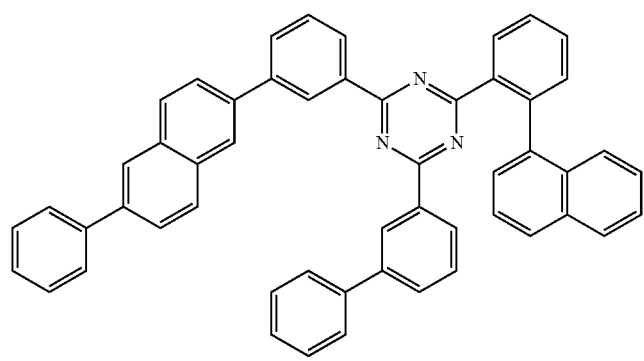

-continued

P-43

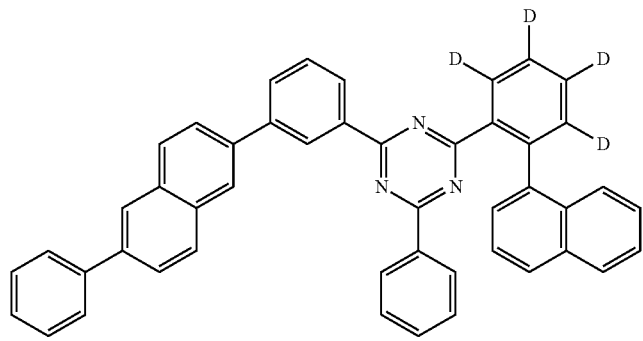

P-44

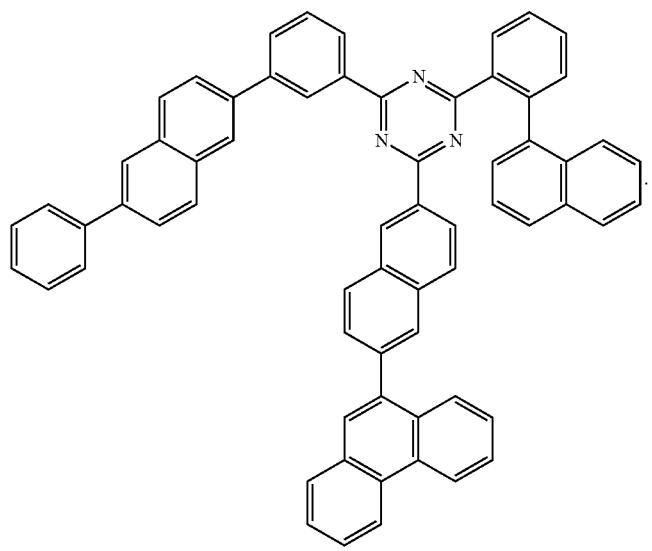

10. An organic electronic element comprising an anode, a cathode, and an organic material layer formed between the anode and the cathode, wherein the organic material layer comprises a single compound or 2 or more compounds represented by Formula 1-1 of claim 1.

11. The organic electronic element of claim 10, wherein the organic material layer comprises at least one of a hole injection layer, a hole transport layer, an emitting-auxiliary layer, an emitting layer, an electron transport auxiliary layer, an electron transport layer, and an electron injection layer.

12. The organic electronic element of claim 10, wherein the organic material layer is an emitting layer.

13. The organic electronic element of claim 10, wherein the organic electronic device further comprises a light efficiency enhancing layer formed on at least one surface of the anode and the cathode, the surface being opposite to the organic material layer.

14. The organic electronic element of claim 10, wherein the organic material layer comprises 2 or more stacks including a hole transport layer, an emitting layer, and an electron transport layer sequentially formed on the anode.

15. The organic electronic element of claim 14, wherein the organic material layer further comprises a charge generation layer formed between the 2 or more stacks.

16. An electronic device comprising: a display device including the organic electronic element of claim 10; and a control unit for driving the display device.

17. The organic electronic element of claim 16, wherein the organic electronic element is any one of an organic electroluminescent device (OLED), an organic solar cell, an organic photo conductor (OPC), an organic transistor (organic TFT), and an element for monochromic or white illumination.

* * * * *